United States Patent
Park et al.

(10) Patent No.: US 9,564,596 B2
(45) Date of Patent: Feb. 7, 2017

(54) HETEROCYCLIC COMPOUND AND ORGANIC LIGHT-EMITTING DEVICE COMPRISING SAME

(71) Applicant: Samsung Display Co., Ltd., Yongin, Gyeonggi-Do (KR)

(72) Inventors: Jun-Ha Park, Yongin (KR); Mi-Eun Jun, Yongin (KR); Eun-Jae Jeong, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 351 days.

(21) Appl. No.: 14/243,800

(22) Filed: Apr. 2, 2014

(65) Prior Publication Data
US 2015/0090965 A1   Apr. 2, 2015

(30) Foreign Application Priority Data
Oct. 2, 2013   (KR) ........................ 10-2013-0118122

(51) Int. Cl.
| | |
|---|---|
| H01L 51/00 | (2006.01) |
| C07D 401/14 | (2006.01) |
| C07D 401/04 | (2006.01) |
| C07D 401/10 | (2006.01) |
| C07D 403/04 | (2006.01) |
| C07D 403/10 | (2006.01) |
| C07D 471/02 | (2006.01) |
| C07D 209/56 | (2006.01) |
| H01L 51/50 | (2006.01) |

(52) U.S. Cl.
CPC ......... *H01L 51/0058* (2013.01); *C07D 209/56* (2013.01); *C07D 401/04* (2013.01); *C07D 401/10* (2013.01); *C07D 401/14* (2013.01); *C07D 403/04* (2013.01); *C07D 403/10* (2013.01); *C07D 471/02* (2013.01); *H01L 51/0072* (2013.01); *H01L 51/006* (2013.01); *H01L 51/0052* (2013.01); *H01L 51/0059* (2013.01); *H01L 51/5072* (2013.01)

(58) Field of Classification Search
None
See application file for complete search history.

(56) References Cited

U.S. PATENT DOCUMENTS

| | | | |
|---|---|---|---|
| 5,645,948 | A | 7/1997 | Shi et al. |
| 2004/0053069 | A1 | 3/2004 | Sotoyama et al. |
| 2004/0137270 | A1 | 7/2004 | Seo et al. |
| 2005/0002857 | A1 | 1/2005 | Pez et al. |
| 2009/0019768 | A1 | 1/2009 | Toseland et al. |
| 2015/0041773 | A1 | 2/2015 | Park et al. |
| 2015/0060787 | A1 | 3/2015 | Park et al. |

FOREIGN PATENT DOCUMENTS

| | | |
|---|---|---|
| JP | 10-017860 | 1/1998 |
| JP | 11-087067 | 3/1999 |
| JP | 2004-071500 A | 3/2004 |
| JP | 4060669 | 12/2007 |
| JP | 2009-029726 A | 2/2009 |
| JP | 2009-123976 A | 6/2009 |
| KR | 10-0525408 | 11/2005 |
| KR | 10-2010-0094261 A | 8/2010 |
| KR | 10-2015-0018229 | 2/2015 |
| KR | 10-2015-0025259 | 3/2015 |

OTHER PUBLICATIONS

Tang, C. W. et al., Organic electroluminescent diodes, Applied Physics Letters, vol. 51, No. 12, Sep. 21, 1987, 4 pgs.
Johansson, N. et al., Solid-State Amplified Spontaneous Emission in Some Spiro-Type Molecules: A New Concept for the Design of Solid-State Lasing Molecules, Advanced Materials, 1998, vol. 10, No. 14, pp. 1136-1141.

(Continued)

*Primary Examiner* — J. L. Yang
(74) *Attorney, Agent, or Firm* — Lewis Roca Rothgerber Christie LLP

(57) ABSTRACT

A compound represented by Formula 1 or 2, and an organic light-emitting device including the same are disclosed.

Formula 1

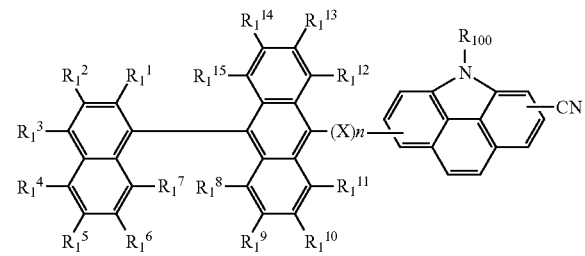

Formula 2

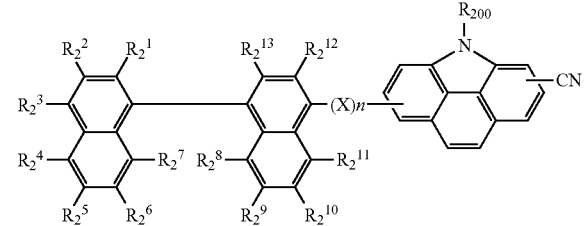

Formulae 1 and 2 are defined as in the specification.

20 Claims, 1 Drawing Sheet

(56) References Cited

OTHER PUBLICATIONS

Adachi, C. et al., Confinement of charge carriers and molecular excitons within 5nm thick emitter layer in organic electroluminescent devices with a double heterostructure, Applied Physics Letters, vol. 57, (6), Aug. 6, 1990, 4 pgs.
Sakamoto, Y. et al., Synthesis, Characterization, and Electron-Transport Property of Perfluorinated Phenylene Dendrimers, Journal American Chemical Society, vol. 122, No. 8, 2000, 2 pgs.
Tao, Y.T. et al., Sharp green electroluminescence from 1H-pyrazolo[3,4-b]quinoline-based light-emitting diodes, Applied Physics Letters, vol. 77, No. 11, Sep. 11, 2000, 4 pgs.
Yamaguchi, S. et al., Diphenylamino-Substituted 2,5-Diarylsiloles for Single-Layer Organic Electroluminescent Devices, Chemistry Letters 2001, 2 pgs.
2009 Fall Assembly and Symposium. vol. 34, No. 2, Oct. 8, 2009, one page.

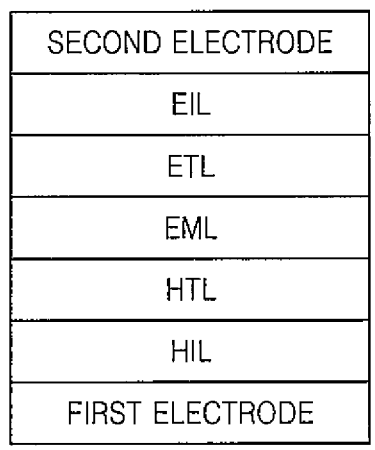

HETEROCYCLIC COMPOUND AND ORGANIC LIGHT-EMITTING DEVICE COMPRISING SAME

CROSS-REFERENCE TO RELATED APPLICATION

This application claims priority to and the benefit of Korean Patent Application No. 10-2013-0118122, filed on Oct. 2, 2013, in the Korean Intellectual Property Office, the disclosure of which is incorporated herein in its entirety by reference.

BACKGROUND

1. Field

The following description relates to a heterocyclic compound and an organic light-emitting device including the same.

2. Description of the Related Art

Organic light-emitting devices, which are self-emitting devices, have wide viewing angles, excellent contrast, quick response, high brightness, excellent driving voltage characteristics, and the ability to provide multicolored images.

A general organic light-emitting device has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds.

An operating principle of an organic light-emitting device having the above-described structure is as follows.

When a voltage is applied between the anode and the cathode, holes injected from the anode move to the EML via the HTL, and electrons injected from the cathode move to the EML via the ETL. Carriers such as the holes and electrons recombine in the EML to generate excitons. When the excitons drop from an excited state to a ground state, light is emitted.

SUMMARY

Aspects of embodiments of the present invention are directed toward a compound for an organic light-emitting device and an organic light-emitting device including the same. Such an organic light-emitting device may have high efficiency, low driving voltage, high brightness, and long lifespan.

Additional aspects will be set forth in part in the description which follows and, in part, will be apparent from the description, or may be learned by practice of the presented embodiments.

According to one or more embodiments of the present invention, a compound is represented by Formula 1 or 2 below:

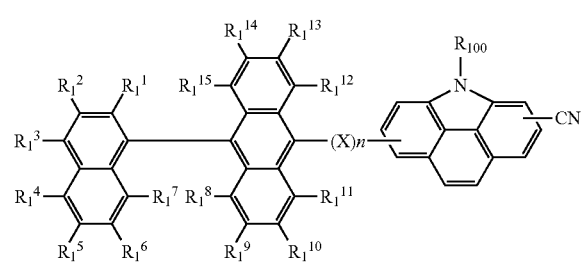

Formula 1

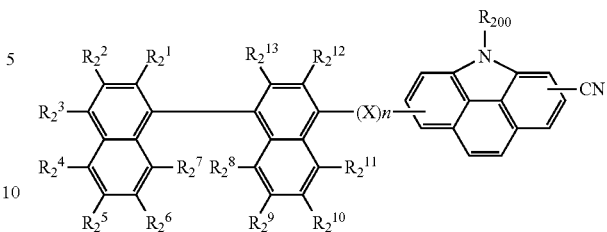

Formula 2

In Formulae 1 and 2, $R_1^1$-$R_1^{15}$, $R_2^1$-$R_2^{13}$, $R_{100}$ and $R_{200}$ are each independently a hydrogen atom, a deuterium atom, a halogen atom, a nitro group, a cyano group, a substituted or unsubstituted $C_1$-$C_{60}$ alkyl group, a substituted or unsubstituted $C_1$-$C_{60}$ alkenyl group, a substituted or unsubstituted $C_3$-$C_{20}$ cycloalkyl group, a substituted or unsubstituted $C_6$-$C_{60}$ aryl group, a substituted or unsubstituted $C_2$-$C_{60}$ heteroaryl group, or a substituted or unsubstituted $C_6$-$C_{60}$ condensed polycyclic group; X is a bivalent linking group selected from the group consisting of a substituted or unsubstituted $C_6$-$C_{40}$ arylene group, a substituted or unsubstituted $C_2$-$C_{60}$ heteroarylene group, or a substituted or unsubstituted $C_6$-$C_{60}$ condensed polycyclic group; and n is an integer from 0 to 5.

According to one or more embodiments of the present invention, an organic light-emitting device includes a first electrode, a second electrode, and an organic layer between the first electrode and the second electrode, wherein the organic layer comprises the compound described above, According to one or more embodiments of the present invention, a flat panel display apparatus includes a thin-film transistor (TFT) including a source electrode and a drain electrode; and the organic light-emitting device, wherein the first electrode of the organic light-emitting device is electrically connected to the source electrode or the drain electrode of the thin-film transistor.

BRIEF DESCRIPTION OF THE DRAWINGS

These and/or other aspects will become apparent and more readily appreciated from the following description of the embodiments, taken in conjunction with the accompanying drawing in which:

The drawing is a schematic cross-sectional view of an organic light-emitting device according to an embodiment of the present invention.

DETAILED DESCRIPTION

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list. Further, the use of "may" when describing embodiments of the present invention refers to "one or more embodiments of the present invention."

A compound according to an embodiment of the present invention is represented by Formula 1 or Formula 2 below:

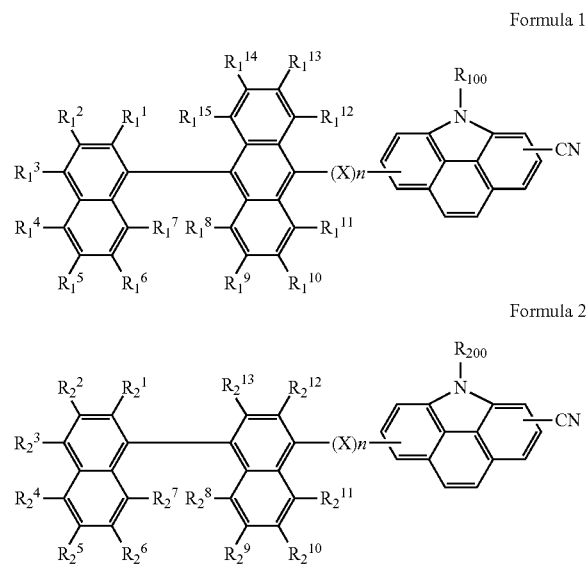

Formula 1

Formula 2

In Formulae 1 and 2, $R_1^1$-$R_1^{15}$, $R_2^1$-$R_2^{13}$, $R_{100}$ and $R_{200}$ are each independently a hydrogen atom, a deuterium atom, a halogen atom, a nitro group, a cyano group, a substituted or unsubstituted $C_1$-$C_{60}$ alkyl group, a substituted or unsubstituted $C_1$-$C_{60}$ alkenyl group, a substituted or unsubstituted $C_3$-$C_{20}$ cycloalkyl group, a substituted or unsubstituted $C_6$-$C_{60}$ aryl group, a substituted or unsubstituted $C_2$-$C_{60}$ heteroaryl group, or a substituted or unsubstituted $C_6$-$C_{60}$ condensed polycyclic group; X is a bivalent linking group selected from the group consisting of a substituted or unsubstituted $C_6$-$C_{40}$ arylene group, a substituted or unsubstituted $C_2$-$C_{60}$ heteroarylene group, or a substituted or unsubstituted $C_6$-$C_{60}$ condensed polycyclic group; and n is an integer from 0 to 5.

In Formulae 1 and 2, the benzocarbazole group has a heterocyclic structure which forms a firm structure when bound to anthracene, thereby increasing the thermal stability of the compound described above. In addition, when a substituent is bound to position 9 of the benzocarbazole group, the benzocarbazole group is not located in the same plane as that of the substituent. Thus, the benzocarbazole group does not have an electron-donating ability to the substituent. On the other hand, since both benzene rings of the benzocarbazole group are located in the same plane, the benzocarbazole group has an electron-donating ability. Thus, according to an embodiment of the present invention, electronic interaction may be expected by a bond between anthracene and the benzocarbazole group via positions 1-4 of the benzocarbazole group rather than position 9 of the benzocarbazole group. In addition, when anthracene is bound to positions 1-4 of the benzocarbazole group, symmetry of the structure is lower than a structure in which the bond is formed via position 9 of the benzocarbazole group. Accordingly, an amorphous portion (or property) increases, thereby improving the stability of a thin film formed during the manufacture of a device.

Furthermore, since a radical is easily formed via position 6 of the benzocarbazole group, electronic stability may be improved by substitution with —CN at position 6, and electrons may stably flow in a device due to a dipole moment maintained in a direction from anthracene to the benzocarbazole group.

When a molecule having such a structure is used (utilized) in an electron transport layer, intramolecular balance between electrons and holes may be improved and durability against electrons and holes may also be improved. Thus, the compound has high thermal resistance against Joule heating generated in an organic layer, between organic layers, or between an organic layer and a metallic electrode when light emission occurs, and has high durability in high-temperature environments. An organic light-emitting device including the compound represented by Formula 1 or Formula 2 according to an embodiment of the present invention as an electron-transporting material may have high durability during storage and operation and high efficiency.

Substituents of the compounds of Formulae 1 and 2 will now be described in more detail.

According to an embodiment, in Formulae 1 and 2, $R_1^1$, $R_1^2$, $R_1^4$-$R_1^{15}$ and $R_2^1$, $R_2^2$, $R_2^4$-$R_2^{13}$ may be each independently a hydrogen atom or a deuterium atom.

According to another embodiment, $R_{100}$ of Formula 1 and $R_{200}$ of Formula 2 may be each independently a substituted or unsubstituted $C_6$-$C_{60}$ aryl group or a substituted or unsubstituted $C_2$-$C_{60}$ heteroaryl group.

According to another embodiment of the present invention, $R_{100}$ of Formula 1 and $R_{200}$ of Formula 2 may be each independently represented by Formulae 2a to 2g below.

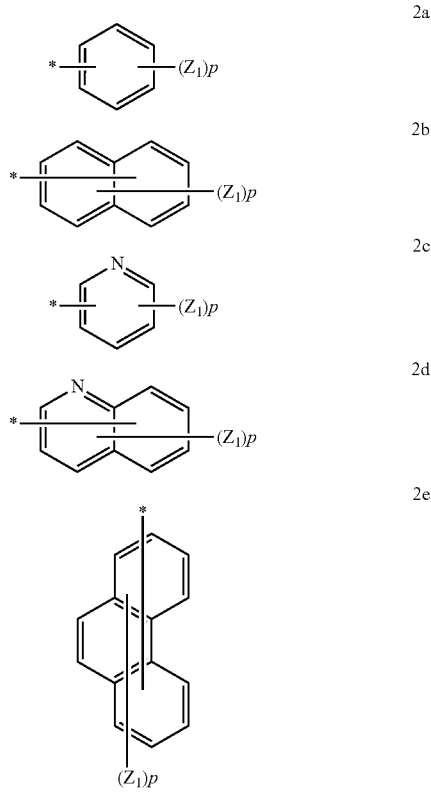

2a

2b

2c

2d

2e

-continued

2f
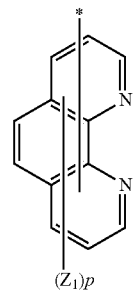

2g
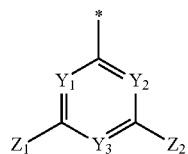

In Formulae 2a to 2g, $Z_1$ and $Z_2$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen atom, a cyano group, a nitro group, a hydroxyl group, or a carboxyl group, wherein when there are a plurality of $Z_1$s, they (i.e., the plurality of $Z_1$s) may be the same or different; $Y_1$ to $Y_3$ are each independently CH or N; p is an integer from 1 to 7; and * is a binding site.

According to another embodiment of the present invention, X of Formula 1 may be represented by Formulae 3a to 3c below.

3a
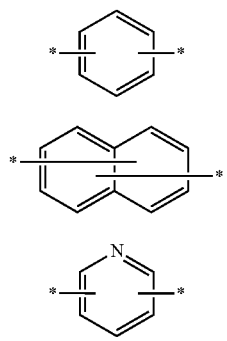

3b

3c

In Formulae 3a to 3c, * is a binding site.

According to another embodiment of the present invention, $R_1^3$ of Formula 1 may be —CN or may be represented by Formulae 4a to 4e below.

4a
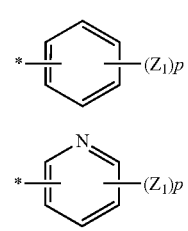

4b

-continued

4c
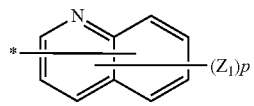

4d
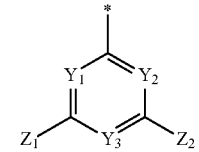

4e
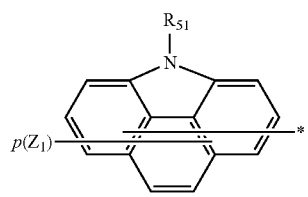

In Formulae 4a to 4e, $Z_1$, $Z_2$, and $R_{51}$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen atom, a cyano group, a nitro group, a hydroxyl group, or a carboxyl group, wherein when there are a plurality of $Z_1$s, they (i.e., the plurality of $Z_1$s) may be the same or different; $Y_1$ to $Y_3$ are each independently CH or N; p is an integer from 1 to 7; and * is a binding site.

According to another embodiment of the present invention, $R_2^3$ of Formula 2 may be —CN or may be represented by Formulae 5a to 5c below.

5a
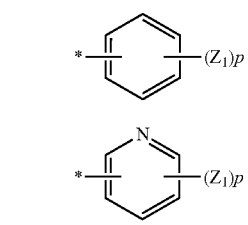

5b

5c
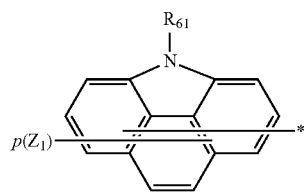

In Formulae 5a to 5c, $Z_1$, and $R_{61}$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen atom, a cyano group, a nitro group, a hydroxyl group, or a carboxyl group, wherein when there are a plurality of $Z_1$s, they (i.e., the plurality of $Z_1$s) may be the same or different; p is an integer from 1 to 7; and * is a binding site.

According to another embodiment of the present invention, n may be an integer from 0 to 2.

Hereinafter, substituents used (utilized) herein will be described in more detail. (The number of carbon atoms in the substituents are presented only for illustrative purposes and do not limit the characteristics of the substituents, and substituents undefined herein may be understood as commonly used (utilized) in the art.)

The unsubstituted $C_1$-$C_{60}$ alkyl group may be linear or branched. Examples of the alkyl group may include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group may be substituted with a deuterium atom, a halogen atom, a hydroxyl group, a nitro group, a cyano group, an amino group, an amidino group, hydrazine, hydrazone, a carboxyl (carboxylic acid) group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_2$-$C_{16}$ heteroaryl group.

The unsubstituted $C_2$-$C_{60}$ alkenyl group refers to a hydrocarbon chain having at least one carbon-carbon double bond within or at a terminal of the unsubstituted alkyl group. Examples of the $C_2$-$C_{60}$ alkenyl group include ethenyl, propenyl, and butenyl. At least one hydrogen atom of the alkenyl group may be substituted with the same substituent groups as described above in connection with the alkyl group.

The unsubstituted $C_2$-$C_{60}$ alkynyl group refers to a hydrocarbon chain having at least one carbon-carbon triple bond within or at a terminal of the alkyl group. Examples of the unsubstituted $C_2$-$C_{60}$ alkynyl group include acetylene, propylene, phenylacetylene, naphthylacetylene, isopropylacetylene, t-butylacetylene, and diphenylacetylene. At least one hydrogen atom of the alkynyl group may be substituted with the same substituent groups as described above in connection with the alkyl group.

The unsubstituted $C_3$-$C_{60}$ cycloalkyl group refers to a $C_3$-$C_{60}$ cyclic alkyl group. At least one hydrogen atom of the cycloalkyl group may be substituted with the same substituent group described above in connection with the $C_1$-$C_{60}$ alkyl group.

The unsubstituted $C_1$-$C_{60}$ alkoxy group is a group having a structure of —OA wherein A is an unsubstituted $C_1$-$C_{60}$ alkyl group as described above. Examples of the $C_1$-$C_{60}$ alkoxy group include methoxy, ethoxy, propoxy, isopropyloxy, butoxy, and pentoxy. At least one hydrogen atom of the alkoxy group may be substituted with the same substituent groups as described above in connection with the alkyl group.

The unsubstituted $C_6$-$C_{60}$ aryl group used (utilized) herein refers to a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom of the aryl group may be substituted with the same substituent groups described with reference to the $C_1$-$C_{60}$ alkyl group.

Examples of the substituted or unsubstituted $C_6$-$C_{60}$ aryl group include a phenyl group, a $C_1$-$C_{10}$ alkylphenyl group (for example, ethylphenyl group), a biphenyl group, a $C_1$-$C_{10}$ alkylbiphenyl group, a $C_1$-$C_{10}$ alkoxybiphenyl group, an o-, m-, and p-toryl group, an o-, m-, and p-cumenyl group, a mesityl group, a phenoxyphenyl group, an ($\alpha,\alpha$-dimethylbenzene)phenyl group, an (N,N'-dimethyl) aminophenyl group, an (N,N'-diphenyl)aminophenyl group, a pentalenyl group, an indenyl group, a naphthyl group, a $C_1$-$C_{10}$ alkylnaphthyl group (for example, methylnaphthyl group), a $C_1$-$C_{10}$ alkoxynaphthyl group (for example, methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrycenyl group, a picenyl group, a perylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted $C_2$-$C_{60}$ heteroaryl group includes one, two, three, or four hetero atoms selected from N, O, P and S. At least two rings thereof may be fused to each other or linked to each other by a single bond. Examples of the unsubstituted $C_2$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, and a dibenzothiophene group. At least one hydrogen atom in the heteroaryl group may be substituted with the same substituent groups described with reference to the $C_1$-$C_{60}$ alkyl group.

The unsubstituted $C_6$-$C_{60}$ aryloxy group used (utilized) herein is a group represented by —$OA_1$. Here, $A_1$ is a $C_6$-$C_{60}$ aryl group. Examples of the aryloxy group include a phenoxy group. At least one hydrogen atom of the aryloxy group may be substituted with the same substituent groups described with reference to the $C_1$-$C_{60}$ alkyl group.

The unsubstituted $C_6$-$C_{60}$ arylthio group used (utilized) herein is a group represented by —$SA_1$. Here, $A_1$ is a $C_6$-$C_{60}$ aryl group. Examples of the arylthio group include a benzenethio group and a naphthylthio group. At least one hydrogen atom of the arylthio group may be substituted with the same substituent groups described with reference to the $C_1$-$C_{60}$ alkyl group.

The unsubstituted $C_6$-$C_{60}$ condensed polycyclic group is a substituent including at least two rings in which at least one aromatic ring and/or at least one non-aromatic ring are fused to each other or a substituent including an unsaturated ring without having a conjugation structure. The condensed polycyclic group is distinguished from the aryl group or heteroaryl group since the condensed polycyclic group does not have a single orientation.

The compound represented by Formula 1 according to an embodiment of the present invention may be any one of the Compounds 1 to 97 below, but is not limited thereto.

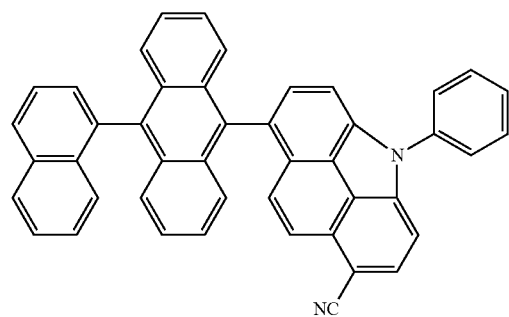
1
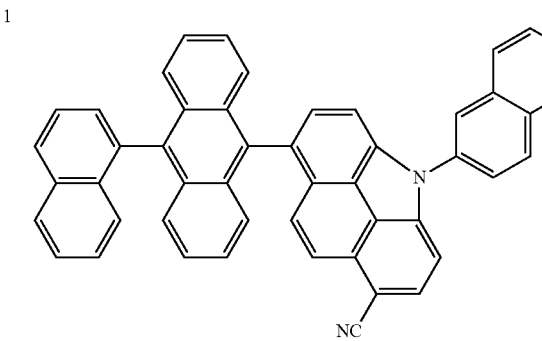
2
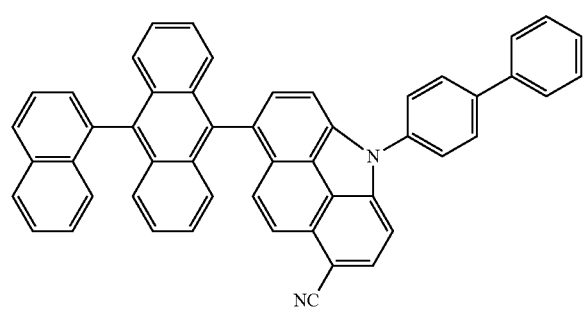
3
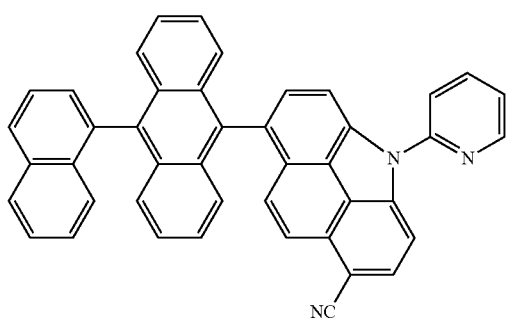
4
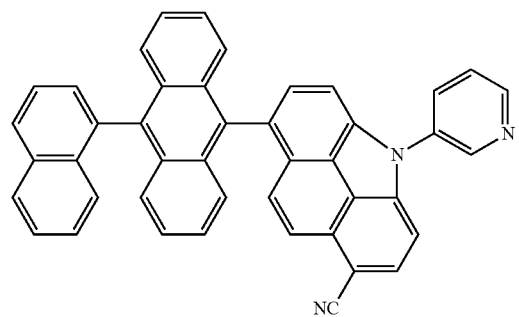
5
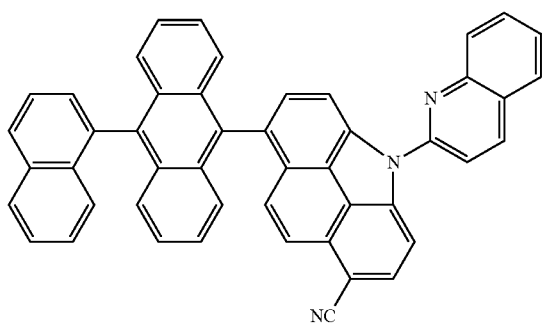
6
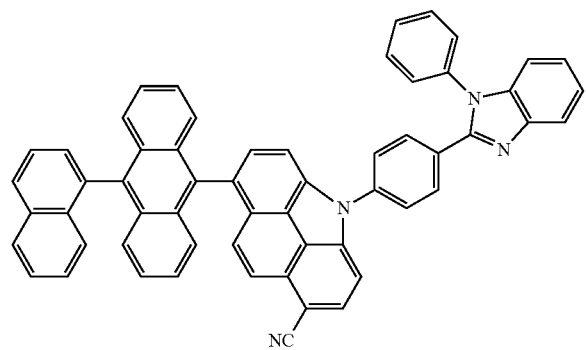
7
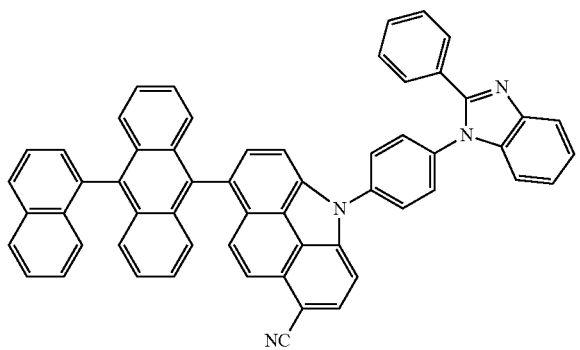
8

-continued
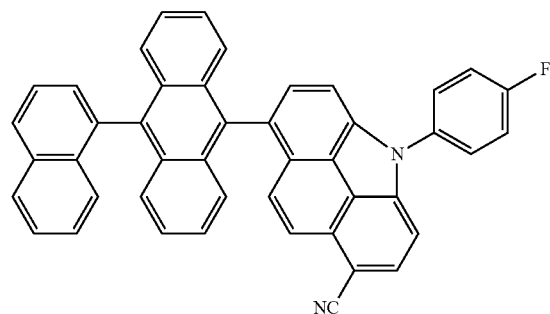
9
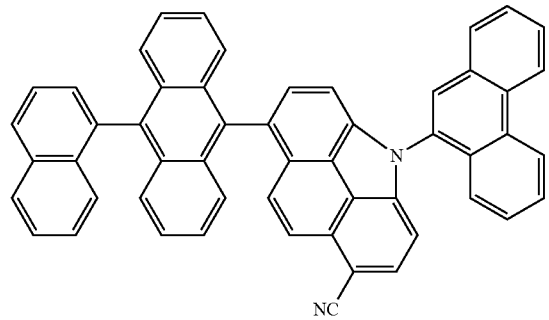
10
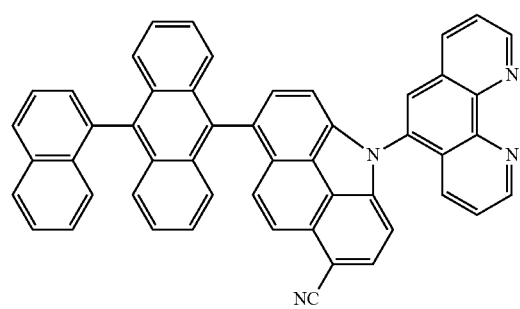
11
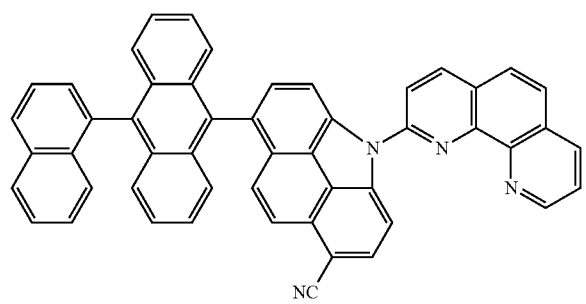
12
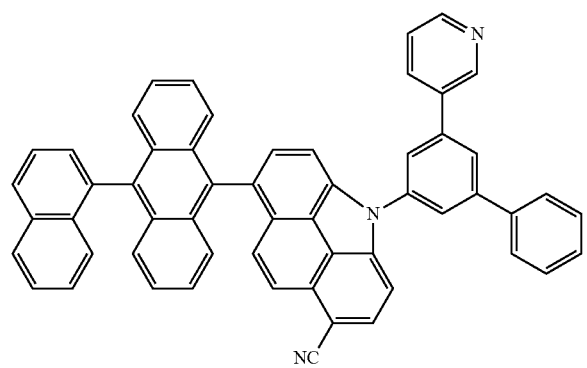
13
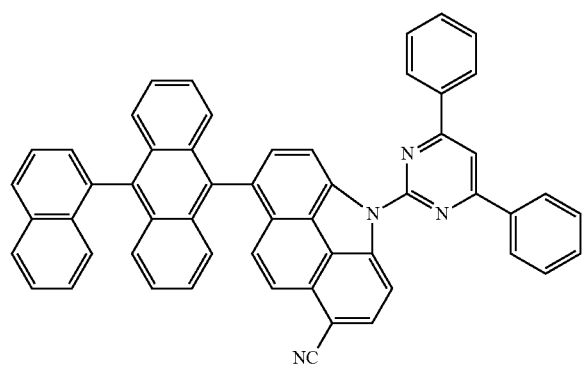
14
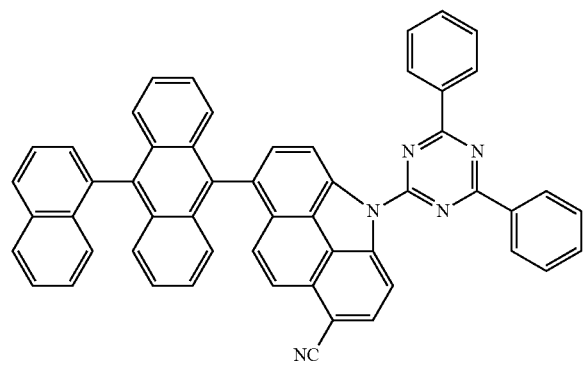
15
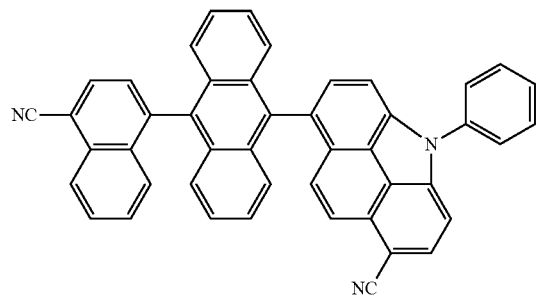
16

-continued
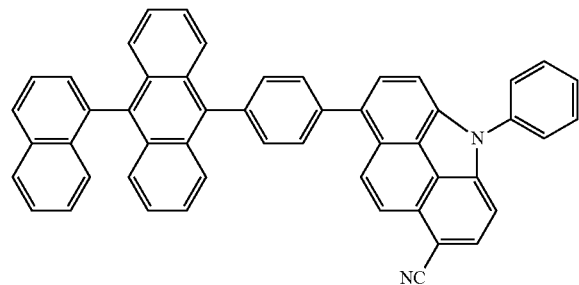
17
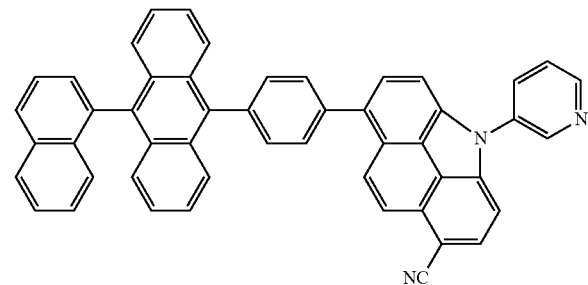
18
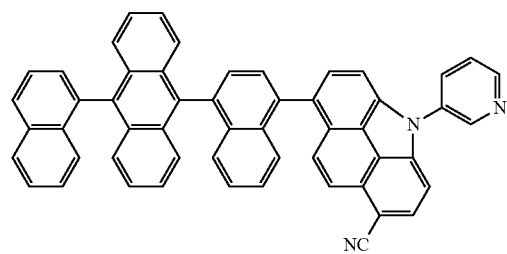
19
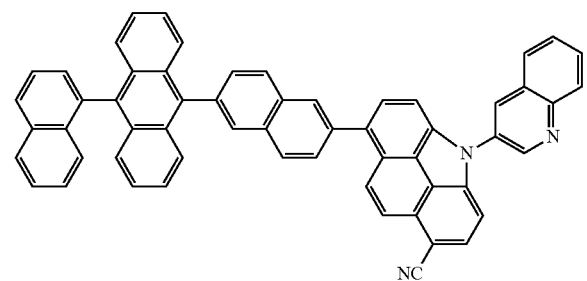
20
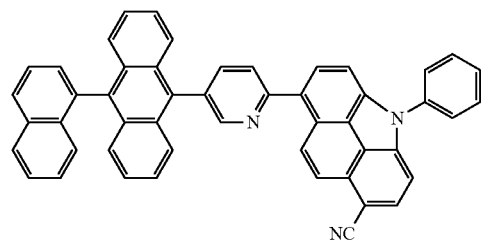
21
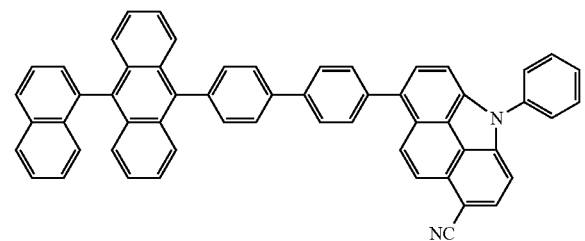
22
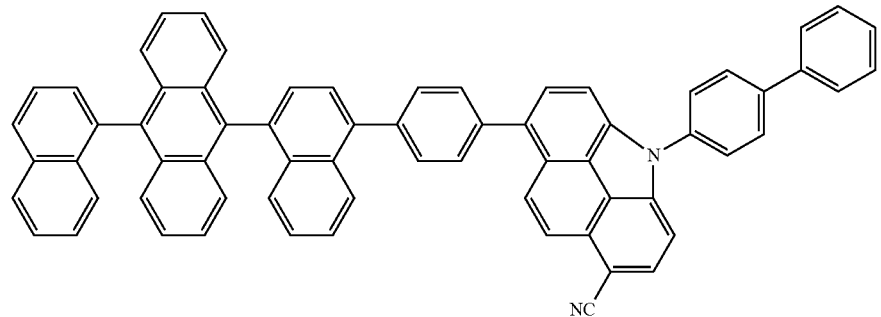
23
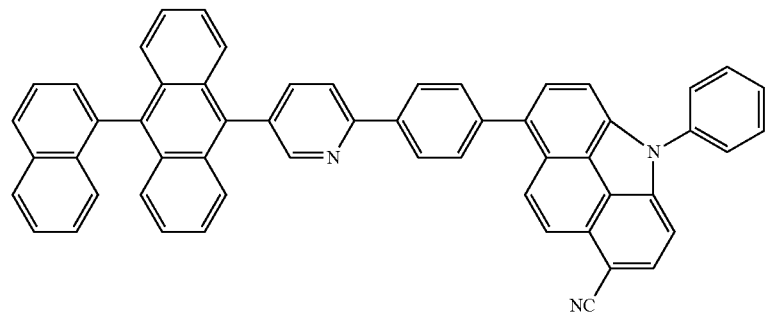
24

-continued
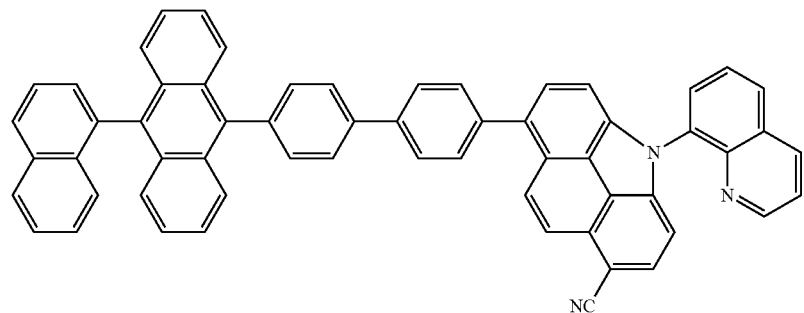
25
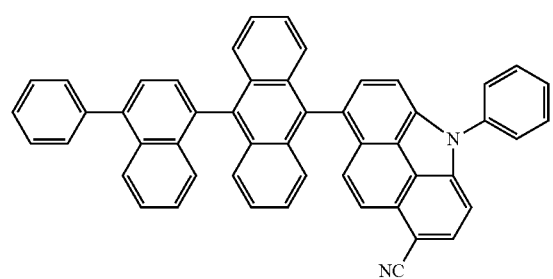
26
27
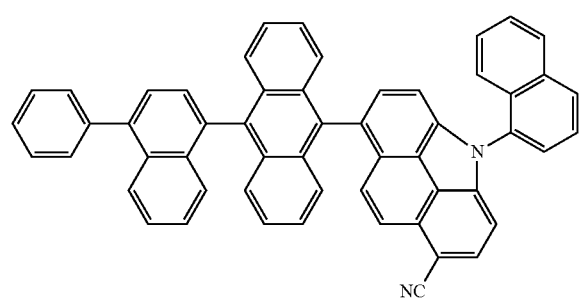
28
29
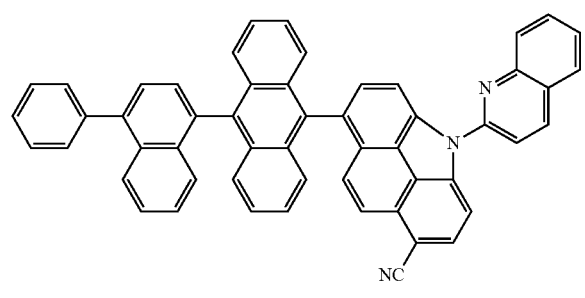
30
31
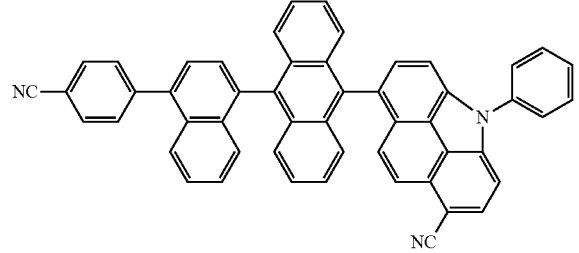
32
33

-continued
34
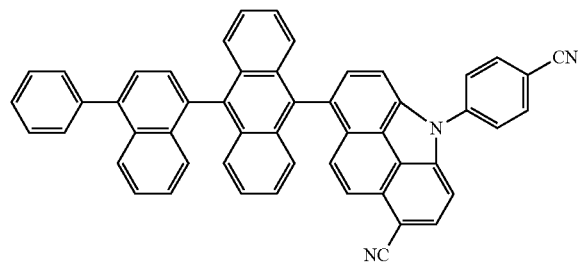
35
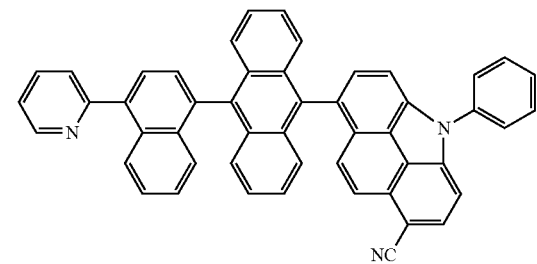
36
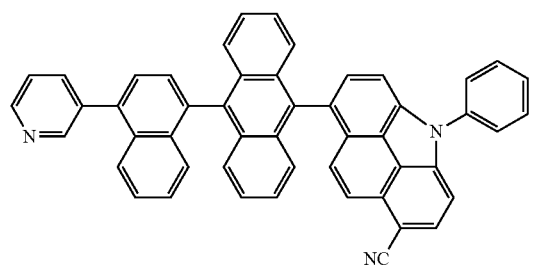
37
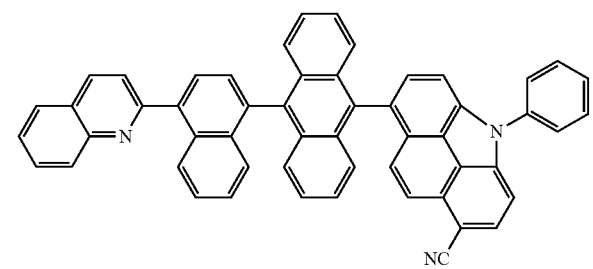
38
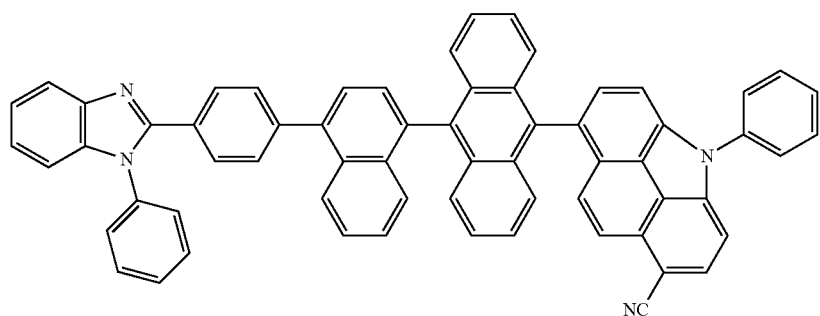
39
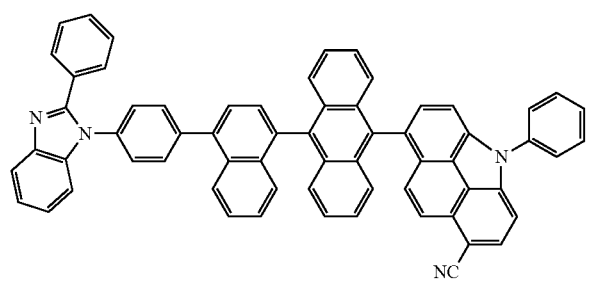
40
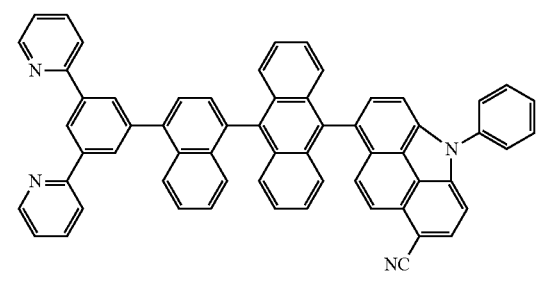
41
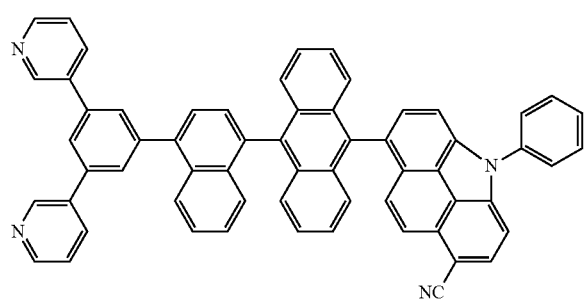
42
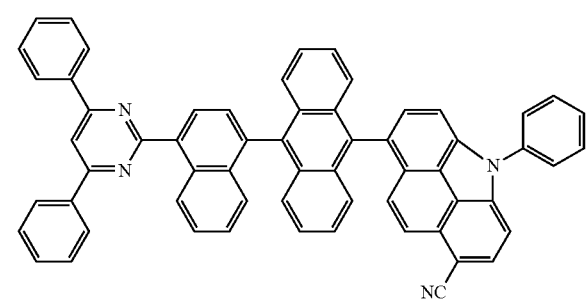

-continued
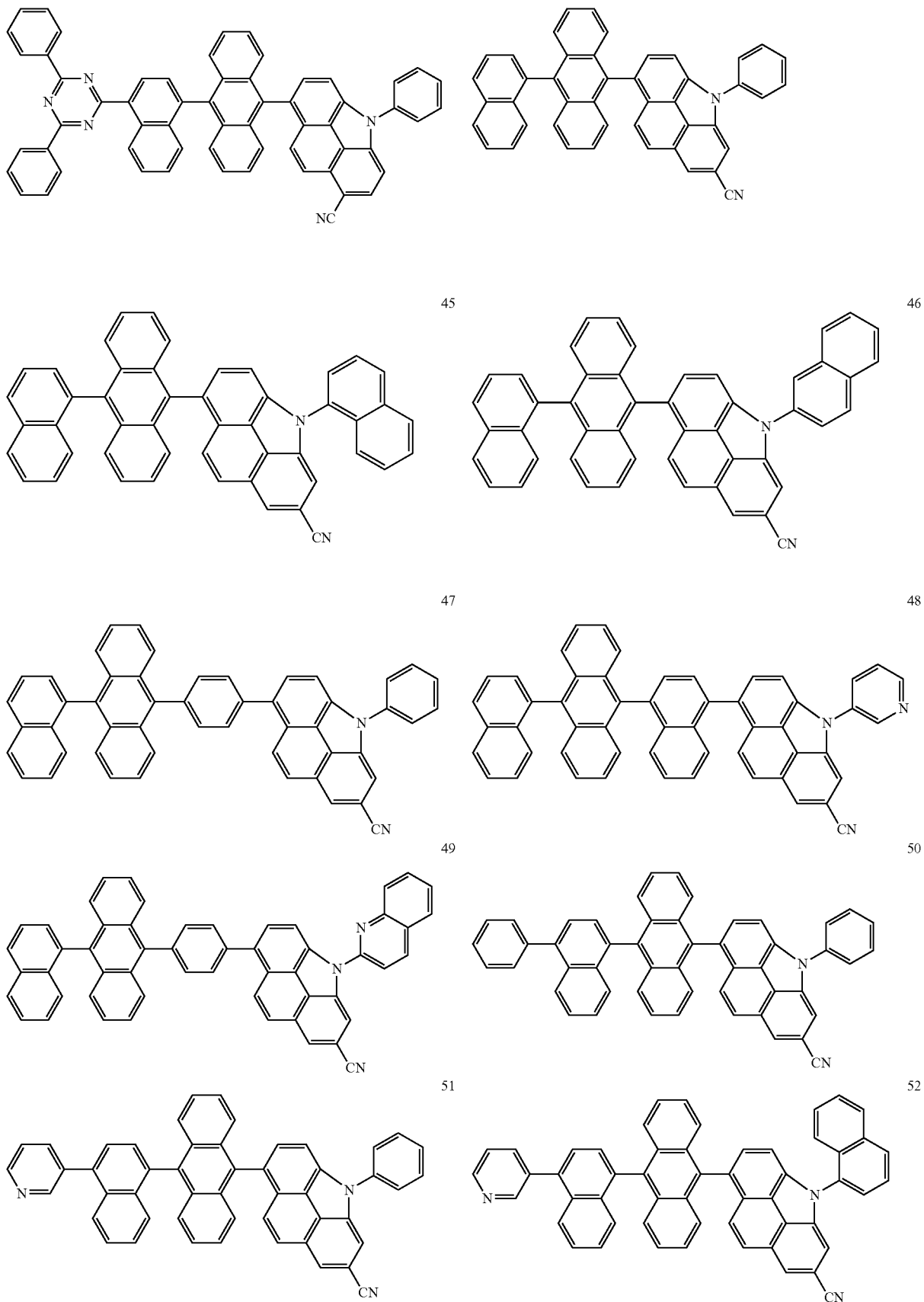

-continued
53
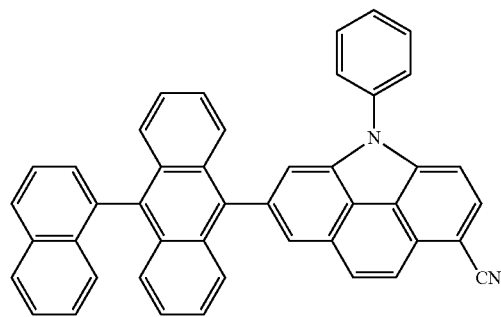
54
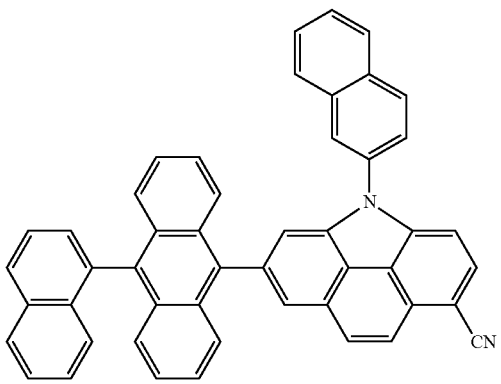
55
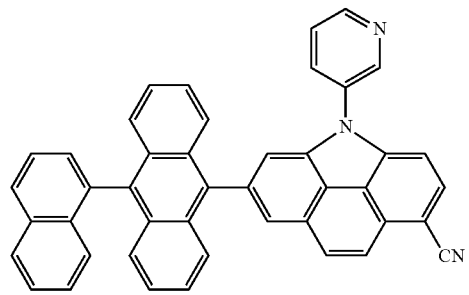
56
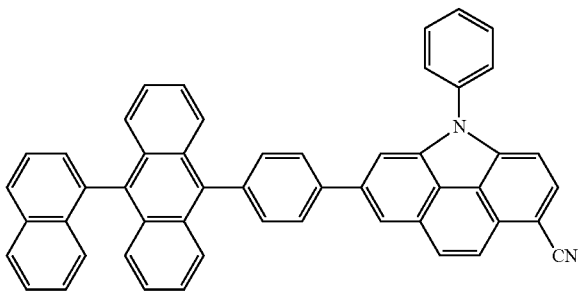
57
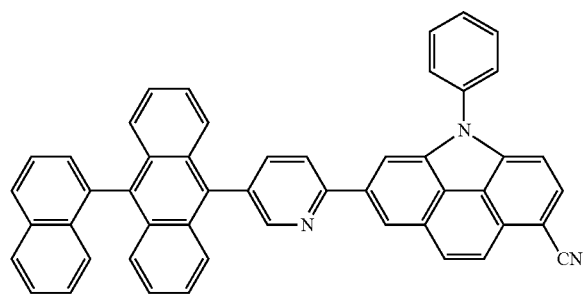
58
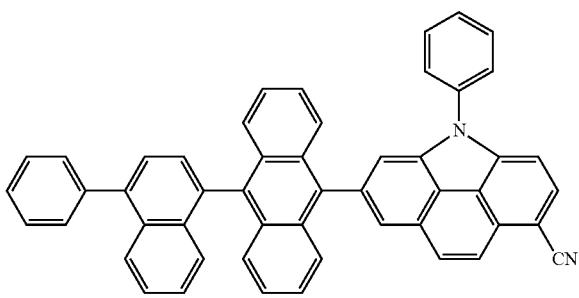
59
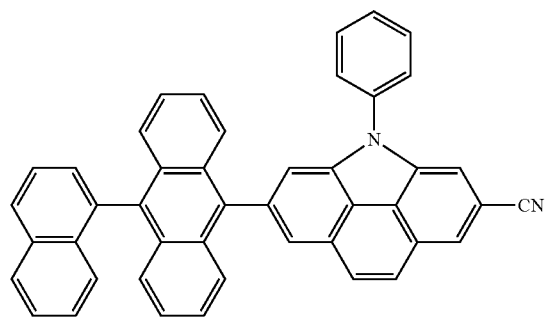
60
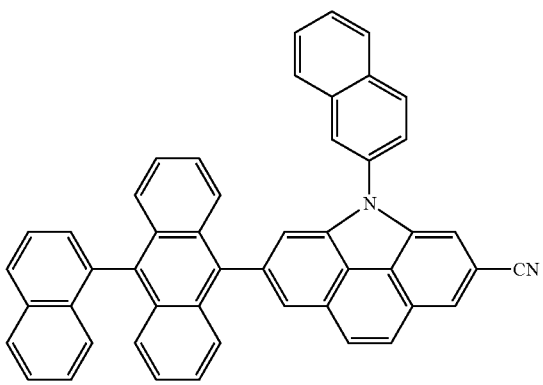

-continued
61
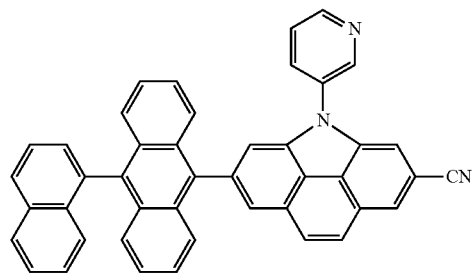
62
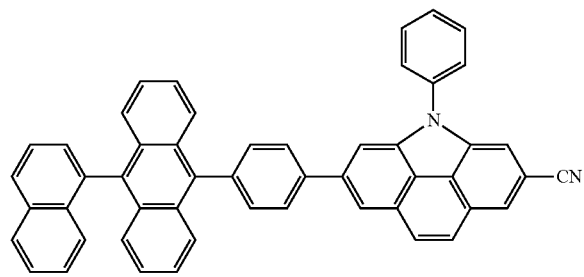
63
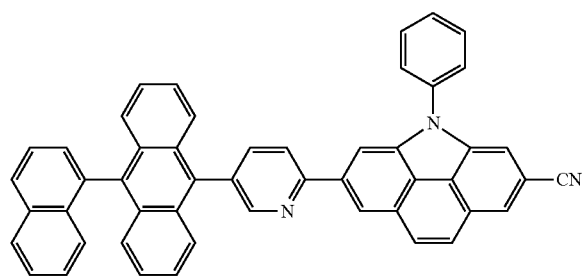
64
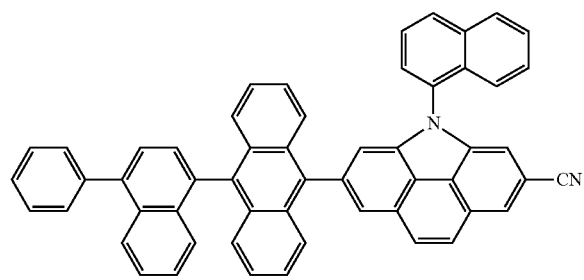
65
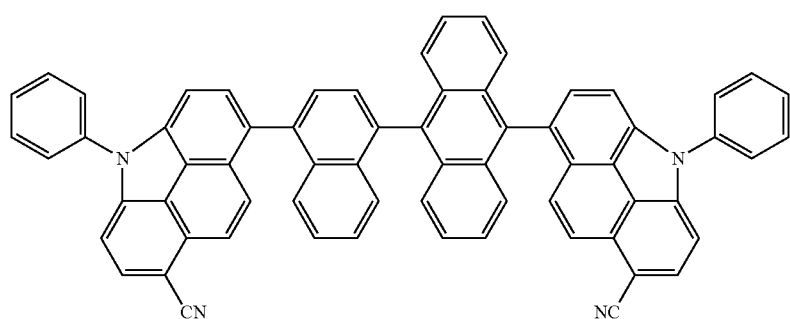
66
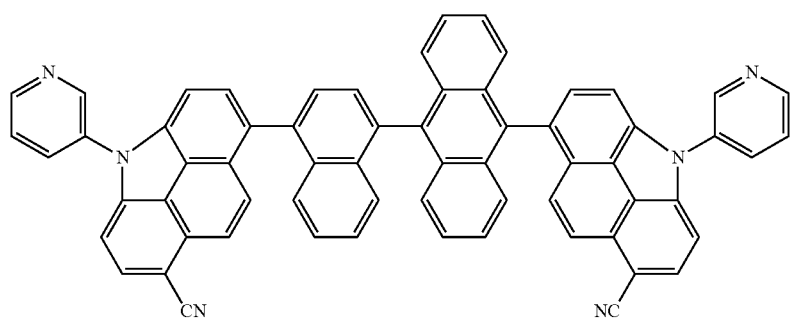
67
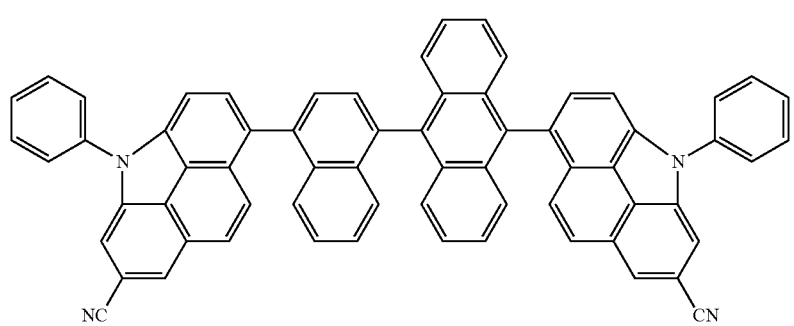

-continued
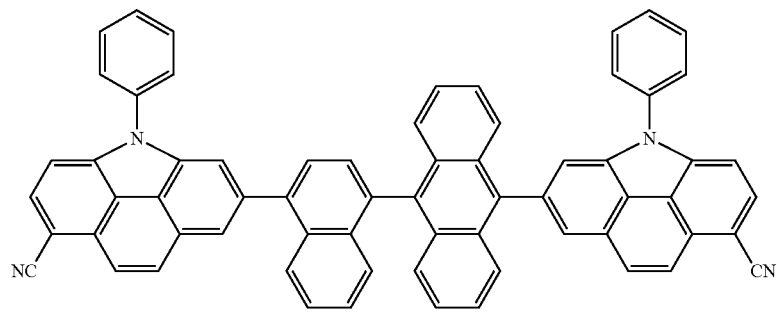
68
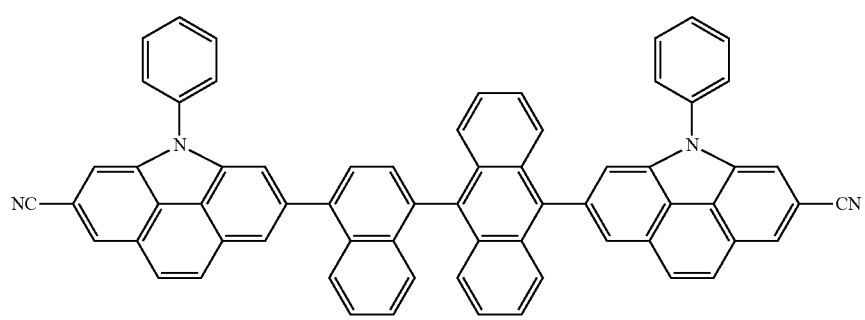
69
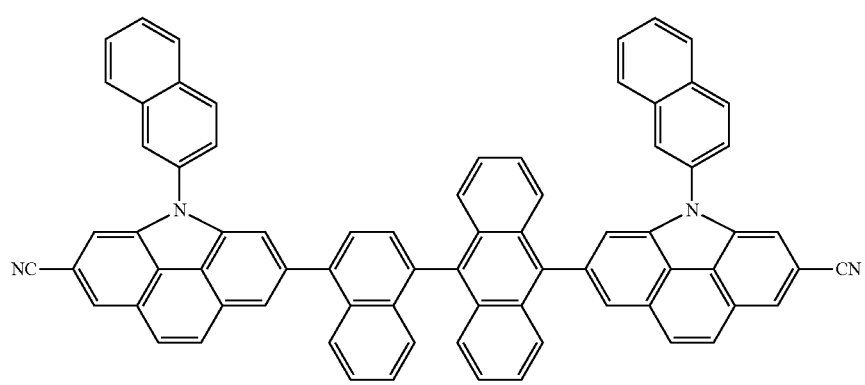
70
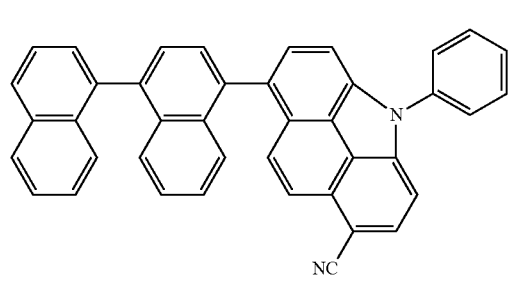
71
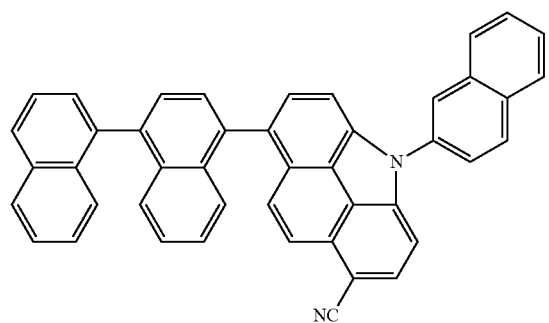
72

-continued
73
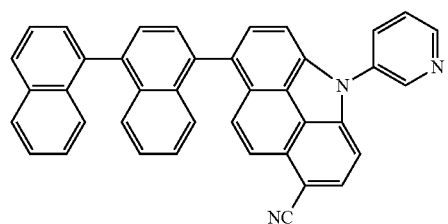
74
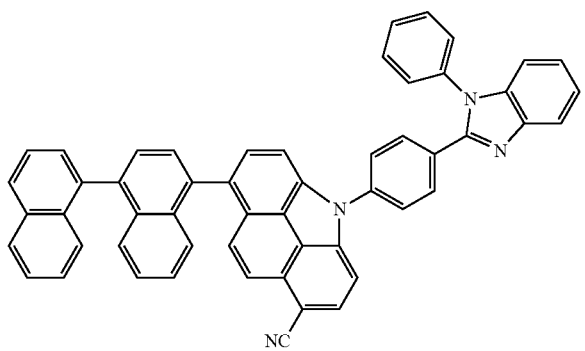
75
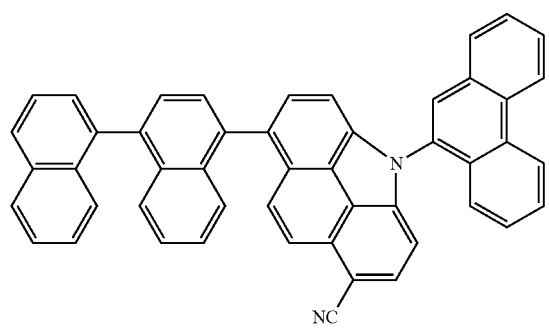
76
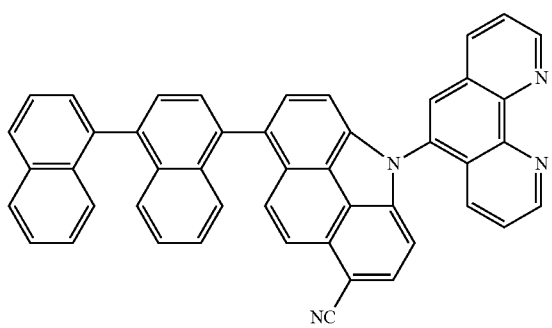
77
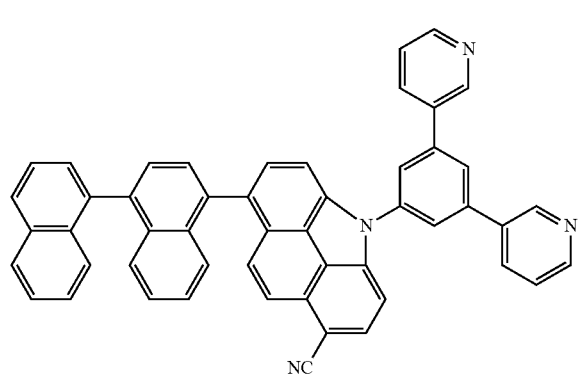
78
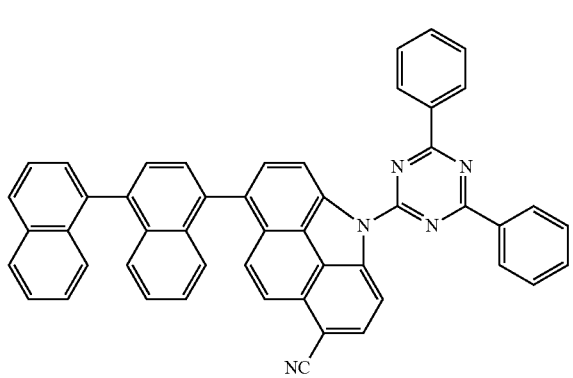
79
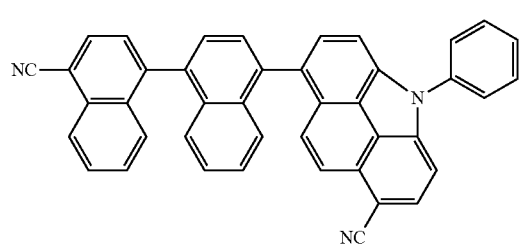
80
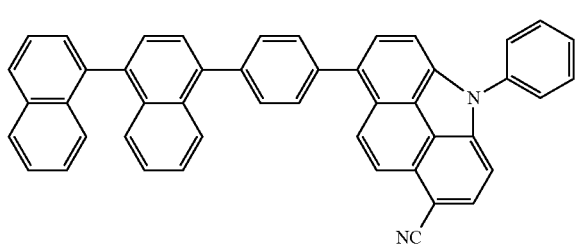
81
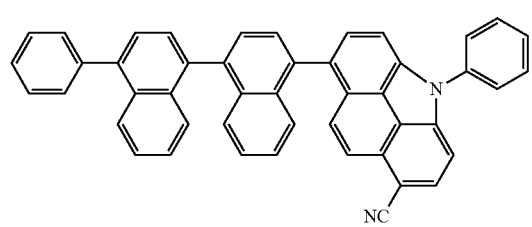
82
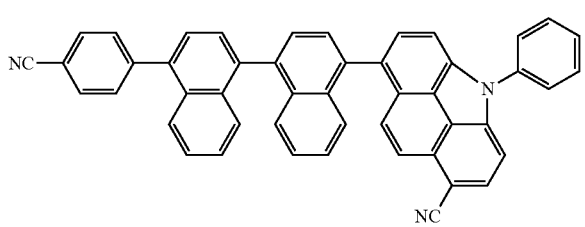

-continued
83
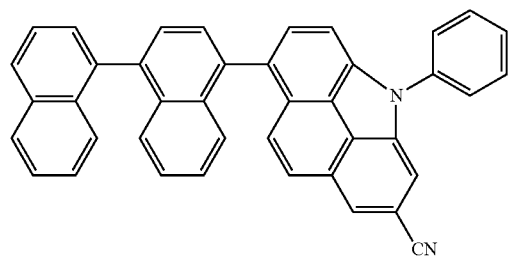
84
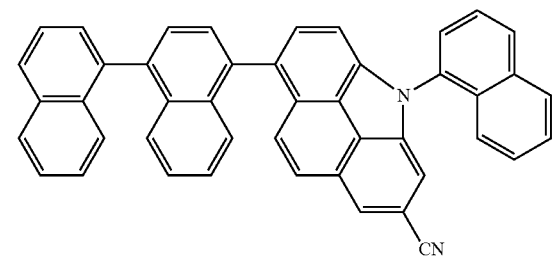
85
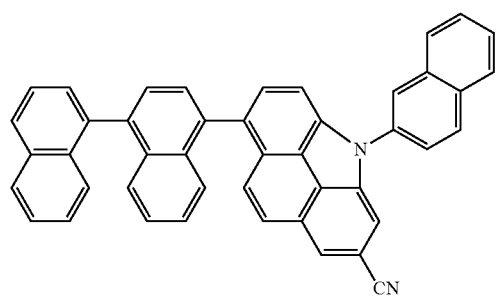
86
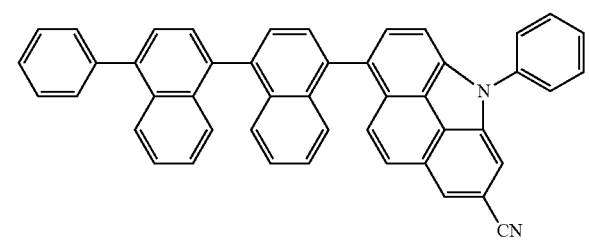
87
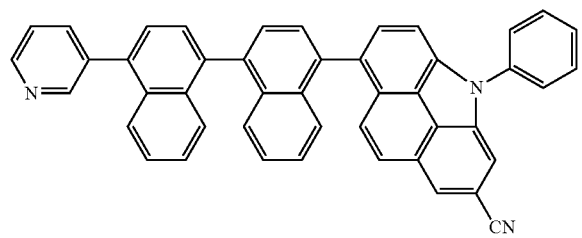
88
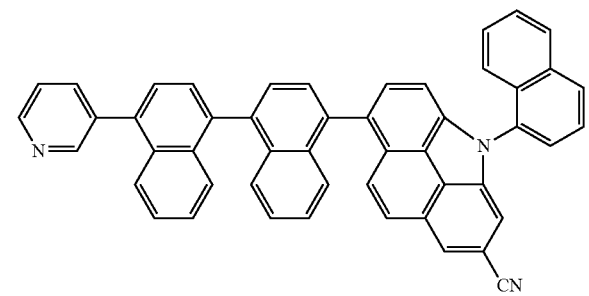
89
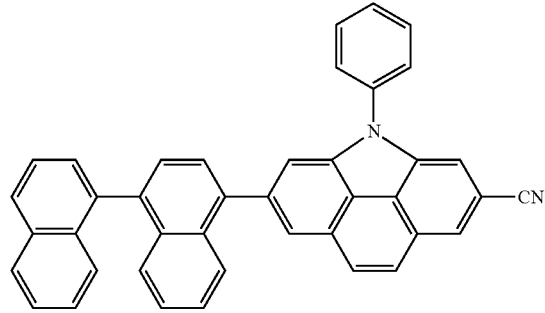
90
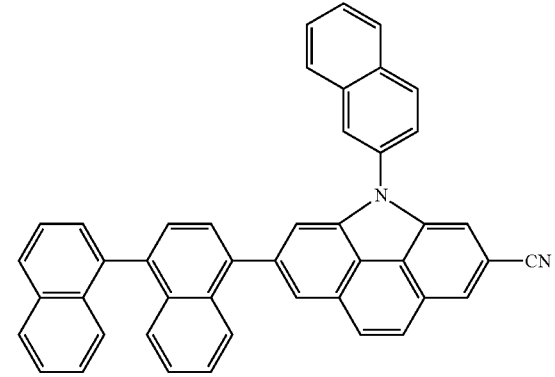
91
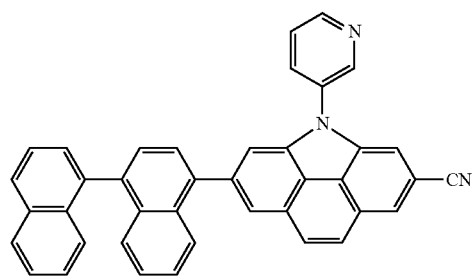
92
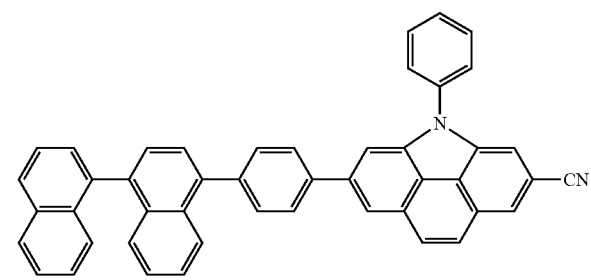

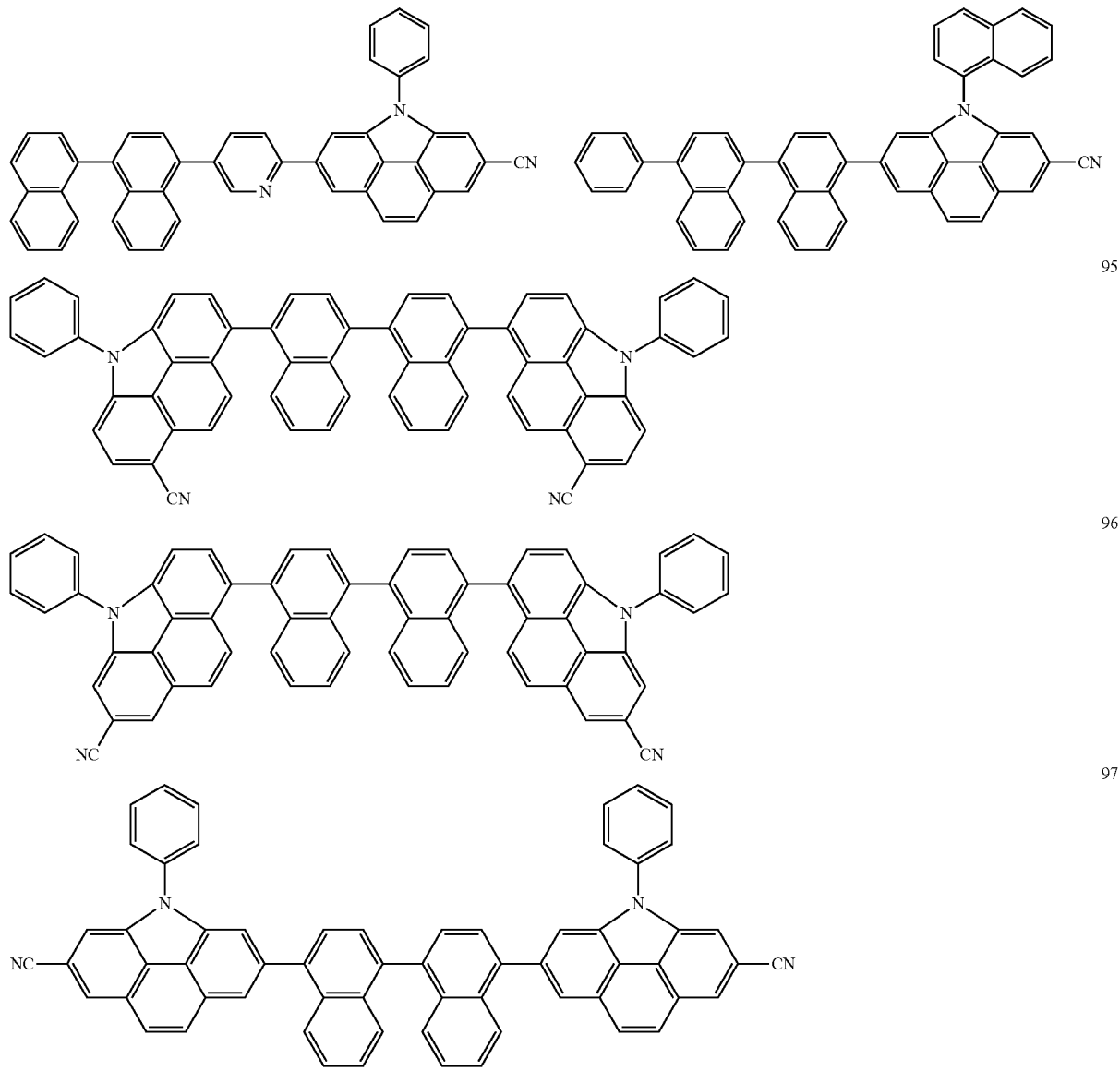

According to another embodiment of the present invention, an organic light-emitting device includes a first electrode, a second electrode, and an organic layer interposed between the first electrode and the second electrode. The organic layer includes the compound represented by Formula 1 or Formula 2 described above.

The organic layer may include at least one layer selected from the group consisting of a hole injection layer (HIL), a hole transport layer (HTL), a functional layer having both hole injecting and hole transporting capabilities (H-functional layer), a buffer layer, an electron blocking layer (EBL), an emission layer (EML), a hole blocking layer (HBL), an electron transport layer (ETL), an electron injection layer (EIL), and a functional layer having both electron injecting and electron transporting capabilities (E-functional layer).

For example, the organic layer may be an EML, for example, a blue EML.

According to an embodiment, the organic layer may include an EML, and an EIL, an ETL, an E-functional layer, an HIL, an HTL, or an H-functional layer, and the EML may include an anthracene-based compound, an arylamine-based compound, or a styryl-based compound.

According to another embodiment, the organic layer may include an EML, and an EIL, an ETL, an E-functional layer, an HIL, an HTL, or an H-functional layer. The EML may include a red emission layer, a green emission layer, a blue emission layer, and a white emission layer, and one of the red, green, blue, and white layers of the EML may include a phosphorescent compound. The HIL, HTL, or H-functional layer may include a charge-generating material. Here, the charge-generating material may be a p-dopant, and the p-dopant may be a quinone derivative, a metal oxide, or a cyano group-containing compound.

According to another embodiment, the organic layer may include an ETL, and the ETL may include an electron-transporting organic compound and a metal complex. The metal complex may be a Li complex.

The term "organic layer" used (utilized) herein refers to a single layer and/or multiple layers interposed between the first and second electrodes of the organic light-emitting device.

The drawing is a schematic cross-sectional view of an organic light-emitting device according to an embodiment of the present invention. Hereinafter, an organic light-emitting device and a method of fabricating the organic light-emitting device will be described with reference to the drawing.

A substrate, which may be any suitable substrate that is commonly used (utilized) in organic light-emitting devices, may be a glass substrate or a transparent plastic substrate with excellent mechanical strength, thermal stability, transparency, surface smoothness, ease of handling, and waterproofness.

The first electrode may be formed on the substrate by depositing or sputtering a material that is used (utilized) to form the first electrode. When the first electrode constitutes an anode, the material used (utilized) to form the first electrode may be a high work function material so as to facilitate hole injection. The first electrode may be a reflective electrode or a transmissive electrode. Transparent and conductive materials such as indium tin oxide (ITO), indium zinc oxide (IZO), tin oxide ($SnO_2$), or zinc oxide (ZnO) may be used (utilized) to form the first electrode. The first electrode may also be formed as a reflective electrode using (utilizing) magnesium (Mg), aluminum (Al), aluminum-lithium (Al—Li), calcium (Ca), magnesium-indium (Mg—In), magnesium-silver (Mg—Ag), or the like.

The first electrode may have a single-layered or multi-layered structure. For example, the first electrode may have a triple-layered structure of ITO/Ag/ITO, without being limited thereto.

An organic layer may be disposed on the first electrode.

The organic layer may include an HIL, an HTL, a buffer layer, an EML, an ETL, and an EIL.

The HIL may be formed on the first electrode by vacuum deposition, spin coating, casting, Langmuir-Blodgett (LB) deposition, or the like.

When the HIL is formed using (utilizing) vacuum deposition, deposition conditions may vary according to a compound used (utilized) to form the HIL, and the structure and thermal characteristics of the HIL to be formed. For example, the deposition conditions may include a deposition temperature of 100 to 500° C., a vacuum pressure of $10^{-8}$ to $10^{-3}$ torr, and a deposition rate of about 0.01 to about 100 Å/sec, without being limited thereto.

When the HIL is formed using (utilizing) spin coating, coating conditions may vary according to a compound that is used (utilized) to form the HIL, and the structure and thermal characteristics of the HIL to be formed. For example, the coating conditions may include a coating speed of about 2000 rpm to about 5000 rpm, and a thermal treatment temperature, for removing a solvent after coating, of about 80° C. to about 200° C., without being limited thereto.

The HIL may be formed of any suitable hole injecting material. Examples of the hole injecting material include N,N'-diphenyl-N,N'-bis-[4-(phenyl-m-tolyl-amino)-phenyl]-biphenyl-4,4'-diamine (DNTPD), a phthalocyanine compound (such as copperphthalocyanine), 4,4',4"-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline/poly(4-styrenesulfonate) (PANI/PSS), without being limited thereto.

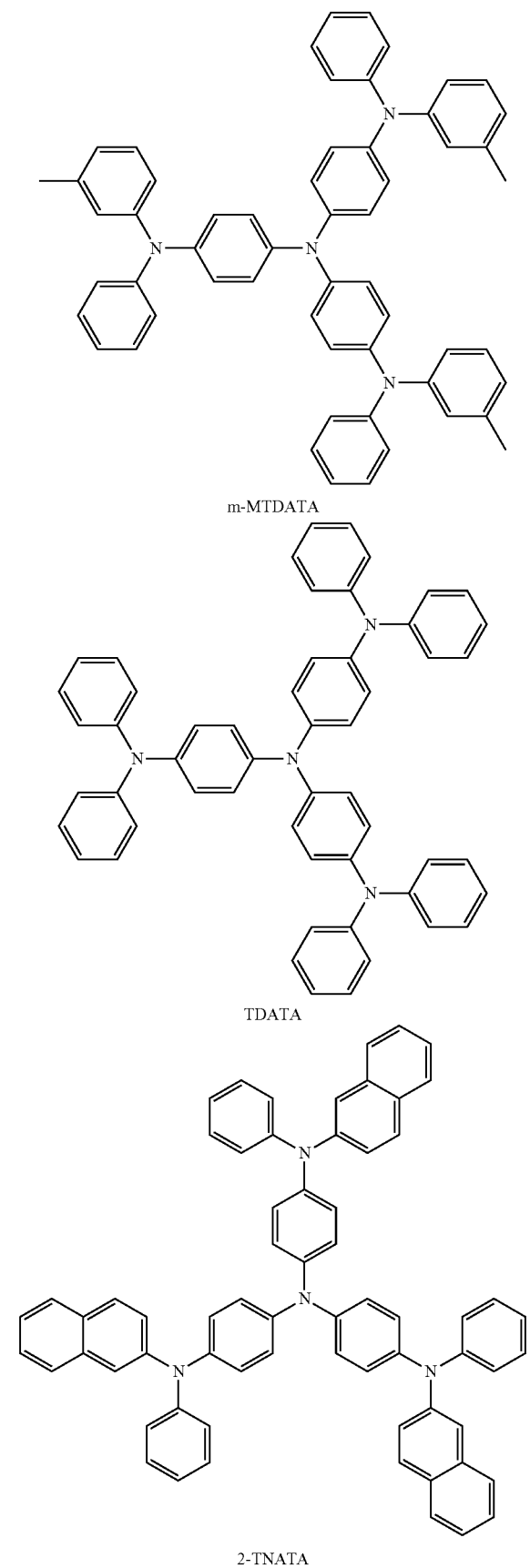

m-MTDATA

TDATA

2-TNATA

The thickness of the HIL may be about 100 to about 10,000 Å, for example, about 100 to about 1,000 Å. In one embodiment, when the thickness of the HIL is within this range, the HIL has an excellent hole injecting ability without a substantial increase in driving voltage.

Then, the HTL may be formed on the HIL by using (utilizing) vacuum deposition, spin coating, casting, LB deposition, or the like. When the HTL is formed by vacuum deposition or spin coating, the conditions for deposition and coating may be similar to those for the formation of the HIL, although the conditions for the deposition and coating may vary according to the material that is used (utilized) to form the HTL.

The HTL may be formed of any suitable hole transporting material. Examples of the suitable hole transporting material include a carbazole derivative (such as N-phenylcarbazole or polyvinyl carbazole), N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine (NPB), without being limited thereto.

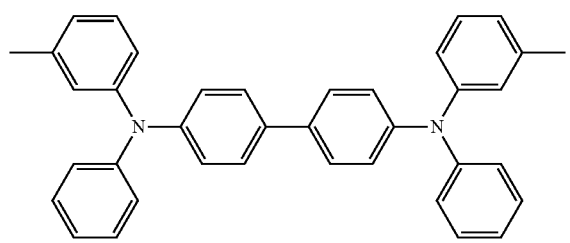

TPD

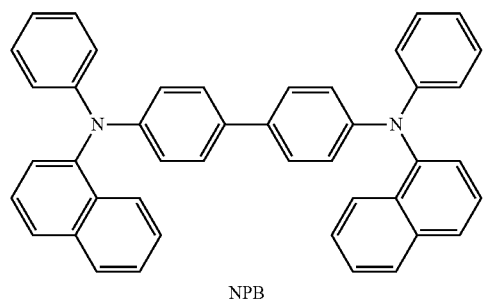

NPB

The thickness of the HTL may be in a range of about 50 to about 2,000 Å, for example, about 100 to about 1,500 Å. In one embodiment, when the thickness of the HTL is within this range, the HTL has an excellent hole transporting ability without a substantial increase in driving voltage.

The H-functional layer may include at least one of the hole injecting materials and the hole transporting materials as described above, and the thickness of the H-functional layer may be in the range of about 50 Å to about 10,000 Å, for example, about 100 Å to about 1,000 Å. In one embodiment, when the thickness of the H-functional layer is within this range, the H-functional layer has excellent hole injecting and transporting abilities without a substantial increase in driving voltage.

Here, at least one of the HIL, HTL, and the H-functional layer may include at least one of the compounds represented by Formulae 300 and 350 below.

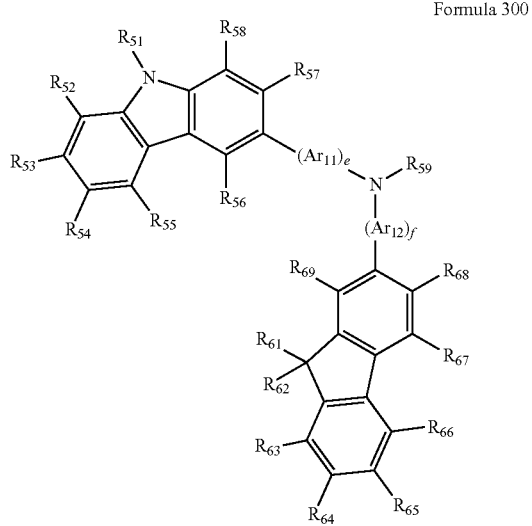

Formula 300

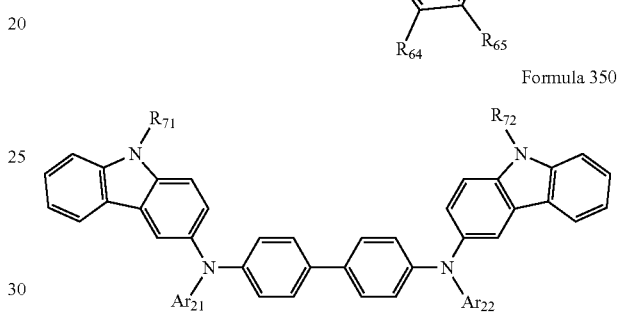

Formula 350

In Formulae 300 and 350, $Ar_{11}$, $Ar_{12}$, $Ar_{21}$, and $Ar_{22}$ are each independently a substituted or unsubstituted $C_6$-$C_{60}$ arylene group.

In Formula 300, e and f may be each independently an integer from 0 to 5, for example, 0, 1, or 2. For example, e may be 1, and f may be 0, without being limited thereto.

In Formulae 300 and 350, $R_{51}$ to $R_{58}$, $R_{61}$ to $R_{69}$, $R_{71}$ and $R_{72}$ may be each independently a hydrogen atom, a deuterium atom, a halogen atom, a hydroxyl group, a cyano group, a nitro group, an amino group, an amidino group, hydrazine, hydrazone, a carboxyl (carboxylic acid) group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, or a substituted or unsubstituted $C_6$-$C_{60}$ arylthio group. For example, $R_{51}$ to $R_{58}$, $R_{61}$ to $R_{69}$, $R_{71}$ and $R_{72}$ may be each independently: a hydrogen atom; a deuterium atom; a halogen atom; a hydroxyl group; a cyano group; a nitro group; an amino group; an amidino group; hydrazine; hydrazone; a carboxyl (carboxylic acid) group or a salt thereof; a sulfonic acid group or a salt thereof; a phosphoric acid or a salt thereof; a $C_1$-$C_{10}$ alkyl group, e.g., a methyl group, an ethyl group, a propyl group, a butyl group, a pentyl group, or a hexyl group; a $C_1$-$C_{10}$ alkoxy group, e.g., a methoxy group, an ethoxy group, a propoxy group, a butoxy group, or a pentoxy group; a $C_1$-$C_{10}$ alkyl group or a $C_1$-$C_{10}$ alkoxy group, each substituted with at least one of a deuterium atom, a halogen atom, a hydroxyl group, a cyano group, a nitro group, an amino group, an amidino group, hydrazine, hydrazone, a carboxyl (carboxylic acid) group or a salt thereof, a sulfonic acid group or a salt thereof, and a phosphoric acid or a salt thereof; a phenyl group; a naphthyl group; an anthryl group; a fluorenyl group; a pyrenyl group; or a phenyl group, a naphthyl group, an anthryl group, a fluorenyl group, or a pyrenyl group, each substituted with at least one of a deuterium atom, a halogen atom, a hydroxyl group, a cyano group, a nitro group, an amino group, an amidino group, hydrazine, hydrazone, a carboxyl (carboxylic acid) group or a salt thereof, a sulfonic acid group or a salt thereof, a phosphoric acid or a salt thereof, a $C_1$-$C_{10}$ alkyl group, and a $C_1$-$C_{10}$ alkoxy group.

In Formula 300, $R_{59}$ may be: a phenyl group; a naphthyl group; an anthryl group; a biphenyl group; a pyridyl group; or a phenyl group, a naphthyl group, an anthryl group, a biphenyl group, or a pyridyl group, each substituted with at least one selected from the group consisting of a deuterium atom, a halogen atom, a hydroxyl group, a cyano group, a nitro group, an amino group, an amidino group, hydrazine, hydrazone, a carboxyl (carboxylic acid) group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

According to an embodiment of the present invention, the compound of Formula 300 may be represented by Formula 300A below, without being limited thereto.

Formula 300A

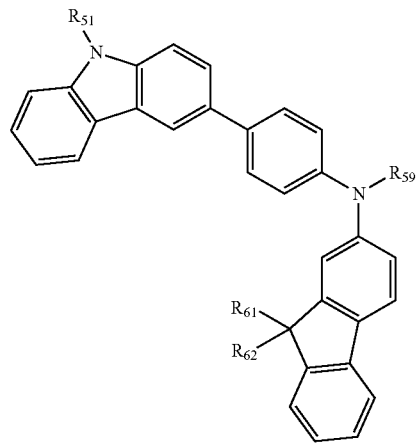

In Formula 300A, $R_{51}$, $R_{61}$, $R_{62}$, and $R_{59}$ are defined as described above.

For example, at least one of the HIL, the HTL, and the H-functional layer may include at least one of Compounds 301 to 320 below, but is not limited thereto:

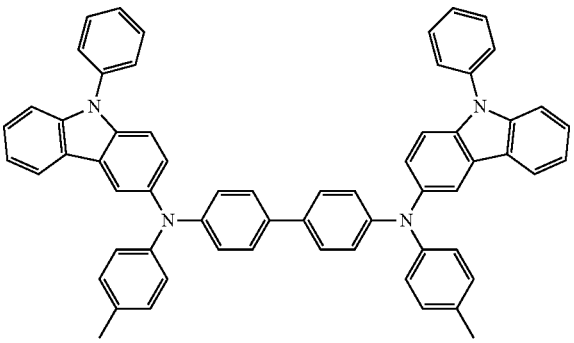

302

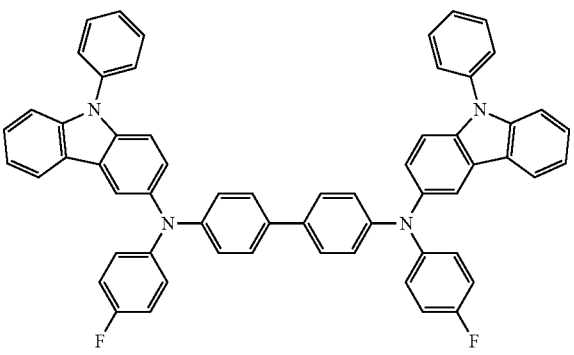

303

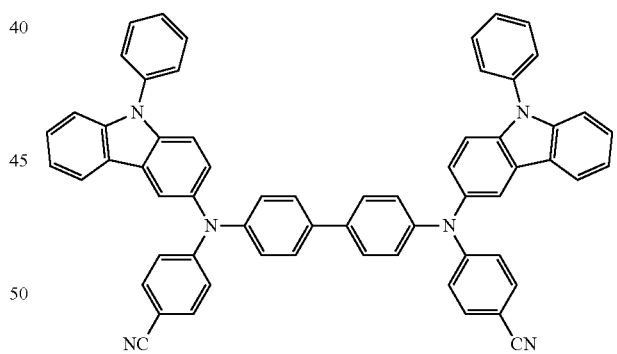

304

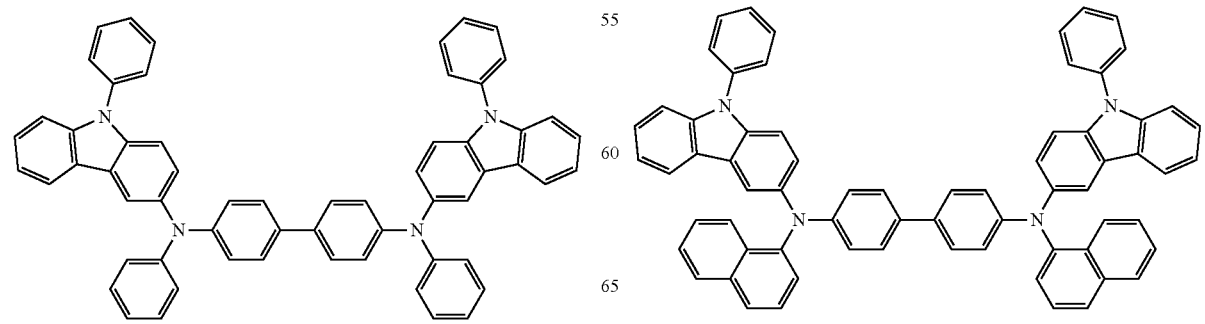

306
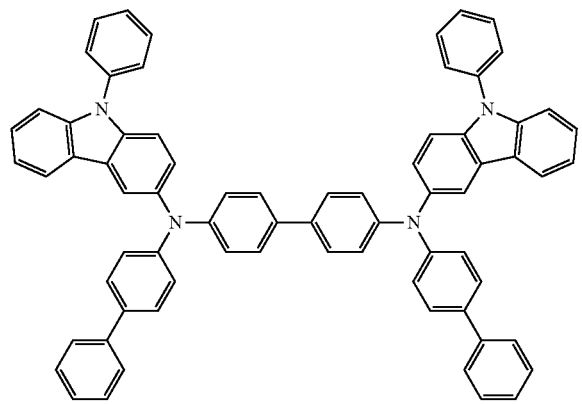
307
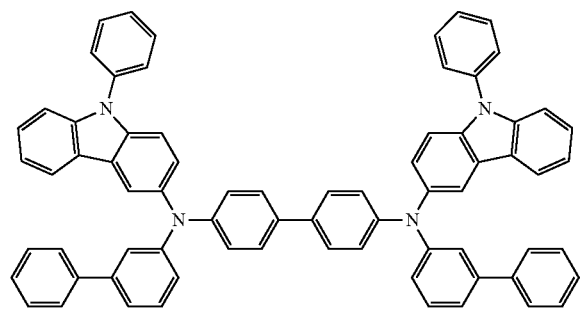
308
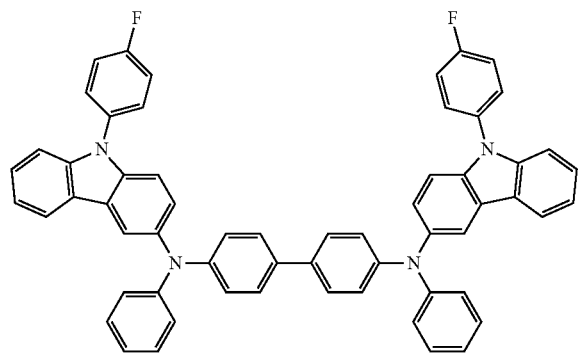
309
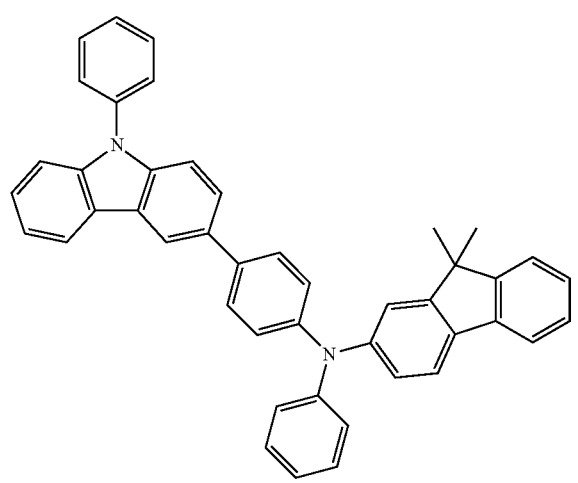
310
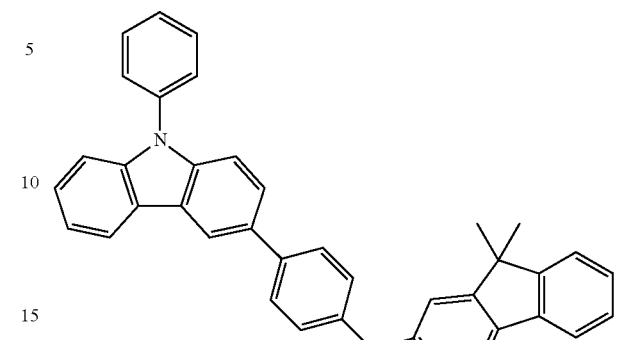
311
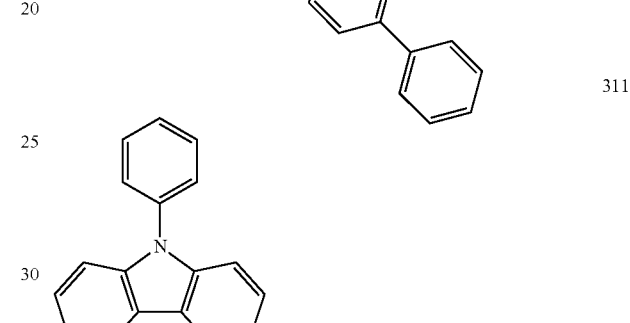
312
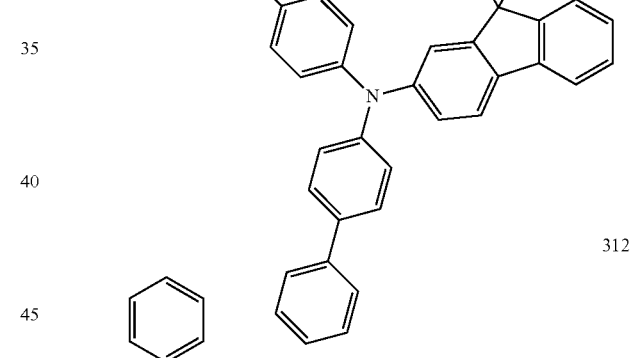
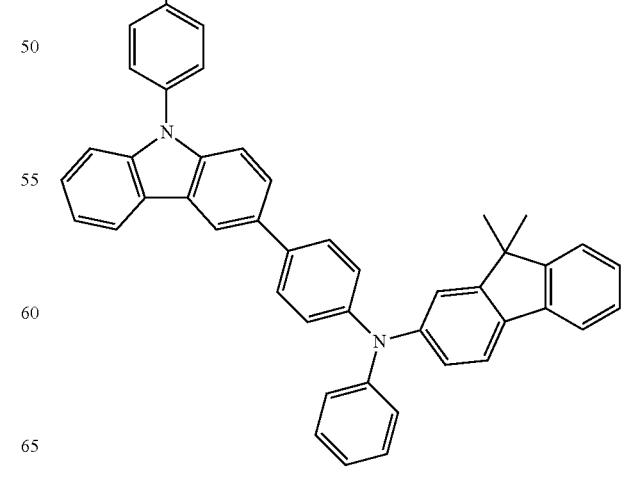

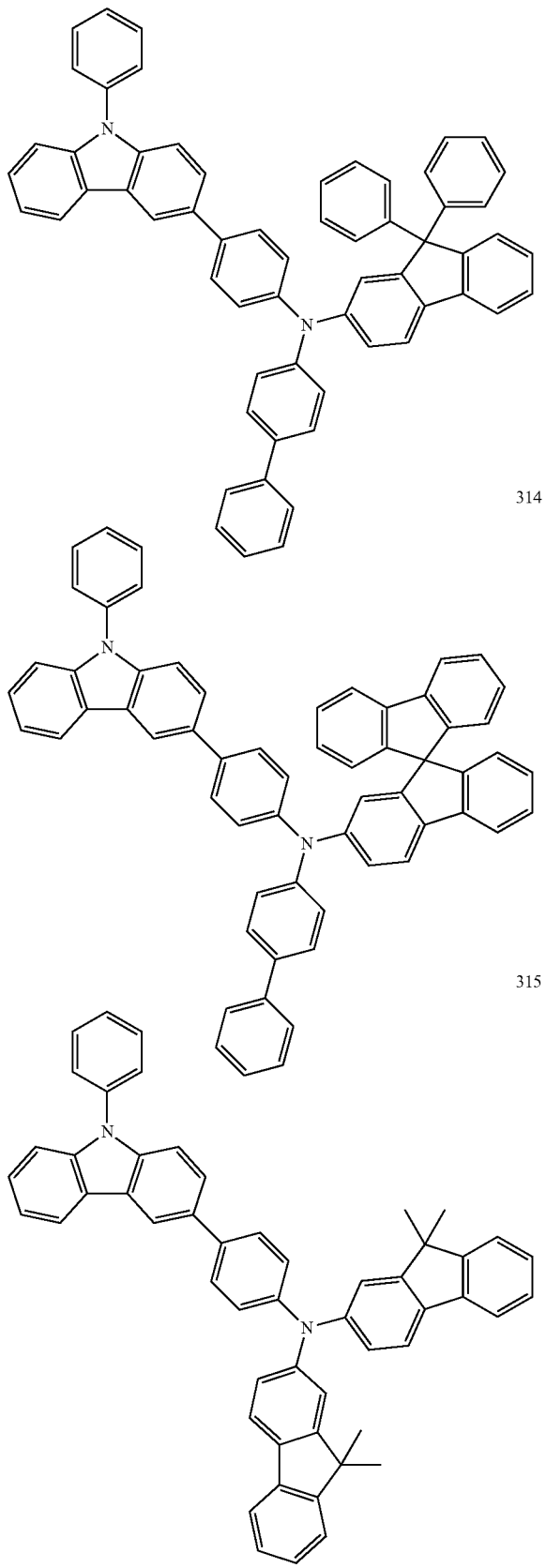
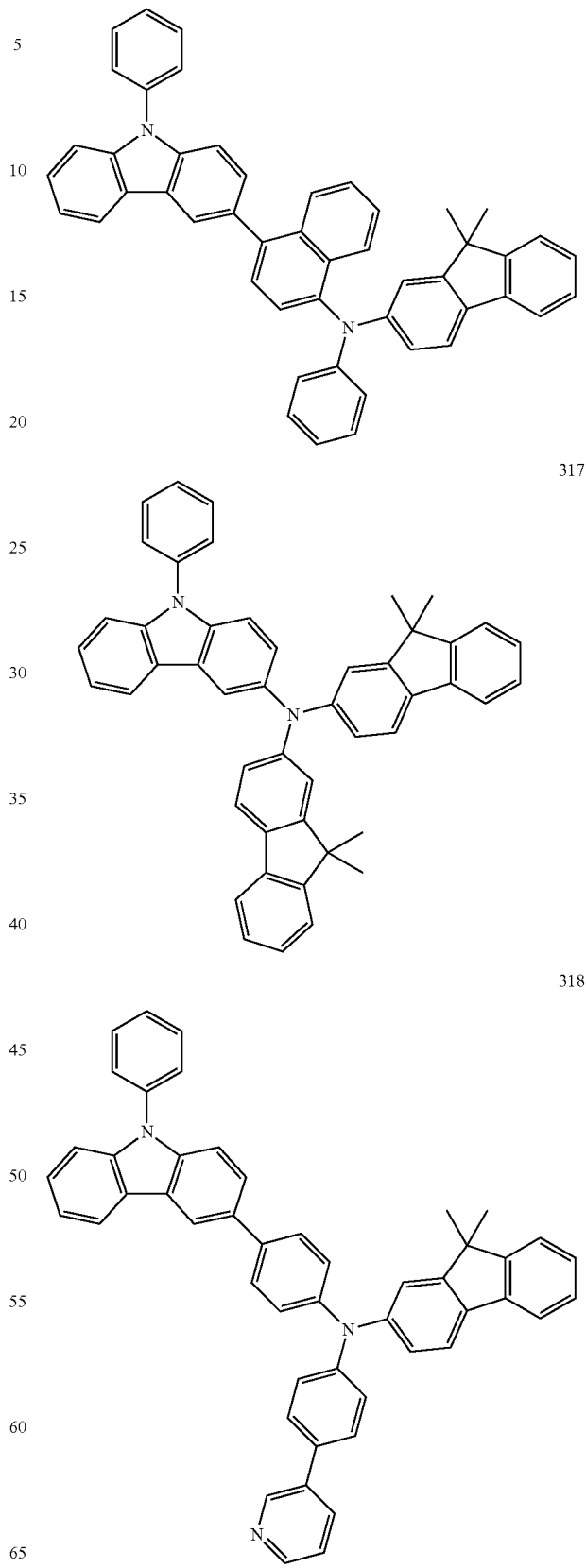

-continued

319

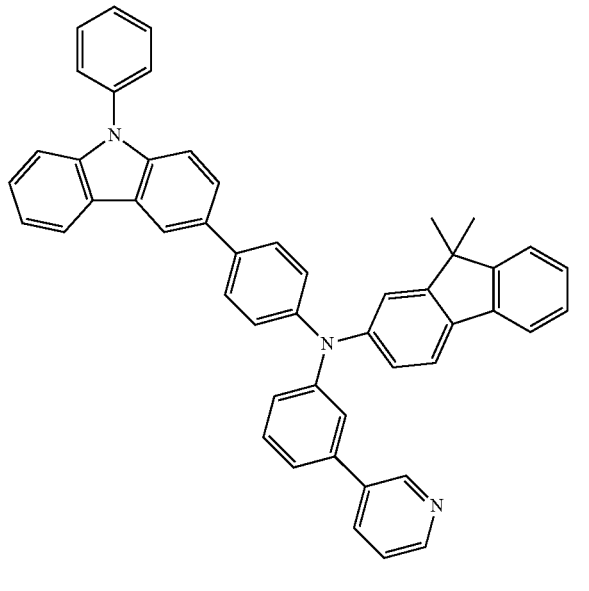

320

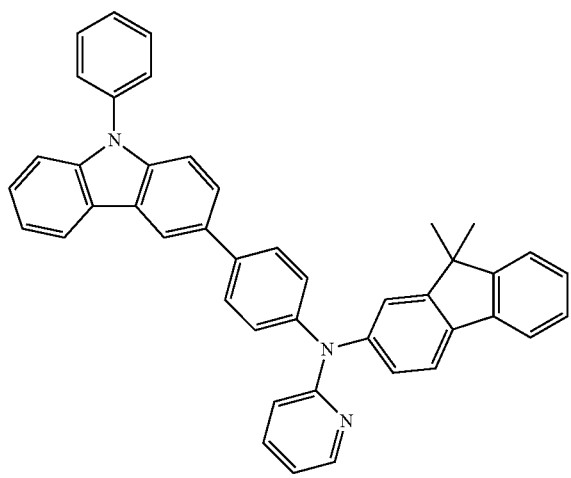

At least one of the HIL, the HTL, and the H-functional layer may further include a charge-generating material in addition to the suitable hole injecting materials, the suitable hole transporting materials, and/or the materials having both hole injecting and hole transporting capabilities in order to improve conductivity of the layer.

The charge-generating material may be a p-dopant. The p-dopant may be a quinone derivative, a metal oxide, or a cyano group-containing compound, but is not limited thereto. Examples of the p-dopant include: a quinine derivative (such as tetracyanoquinonedimethane (TCNQ) or 2,3,5,6-tetrafluoro-tetracyano-1,4-benzoquinonedimethane (F4-TCNQ)); a metal oxide (such as tungsten oxide or molybdenum oxide); and a cyano group-containing compound (such as Compound 200 below), without being limited thereto.

Compound 200

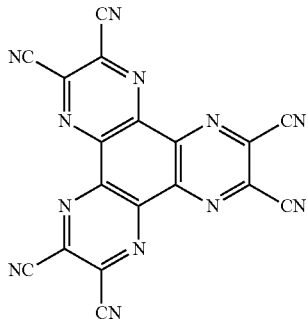

F4-TCNQ

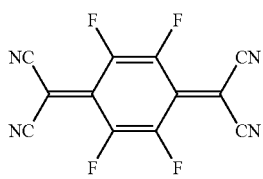

If the HIL, the HTL, or the H-functional layer further includes the charge-generating material, the charge-generating material may be homogeneously or non-homogeneously dispersed in the HIL, the HTL, or the H-functional layer, or a variety of modifications may be possible.

A buffer layer may be interposed between the EML and at least one of the HIL, the HTL, and the H-functional layer. The buffer layer may increase efficiency by compensating an optical resonant distance according to a wavelength of light emitted from the EML. The buffer layer may include suitable hole injecting materials and suitable hole transporting materials. The buffer layer may also include a material that is the same as one of the materials contained in the HIL, the HTL, and the H-functional layer disposed under the buffer layer.

The EML may be formed on the HTL, the H-functional layer, or the buffer layer by vacuum deposition, spin coating, casting, LB deposition, or the like. When the EML is formed by using (utilizing) vacuum deposition or spin coating, the deposition and coating conditions may be similar to those used (utilized) to form the HIL, although the deposition and coating conditions may vary according to a compound that is used (utilized) to form the EML.

The EML may be formed using (utilizing) various suitable hosts and dopants. The dopant for forming the EML may include suitable fluorescent dopants or phosphorescent dopants.

For example, examples of suitable host materials may include Alq$_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl)anthracene (TBADN), E3, distyrylarylene (DSA), dmCBP (refer to the following formula), and Compounds 501 to 509 below, but is not limited thereto.

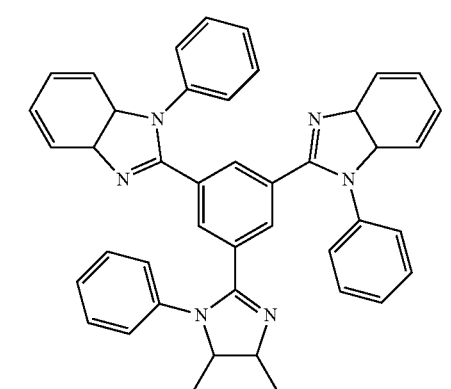
TPBI
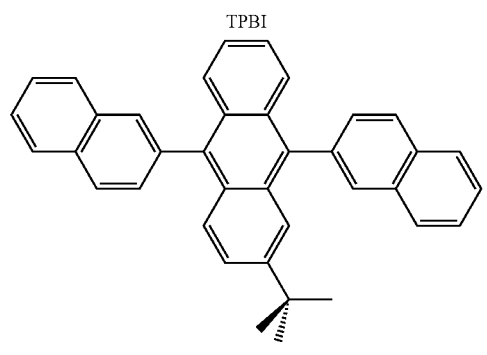
TBADN
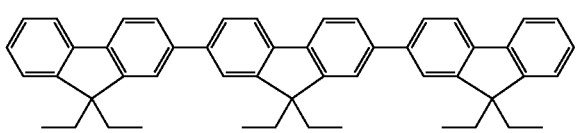
E3
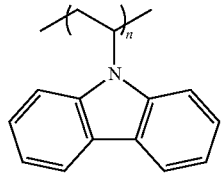
PVK
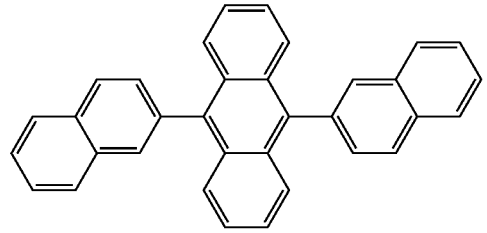
ADN
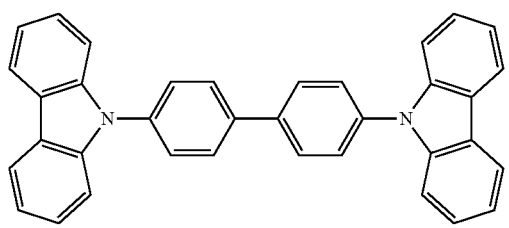
CBP
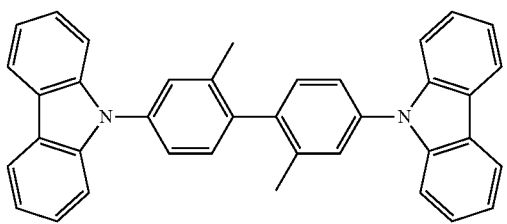
dmCBP
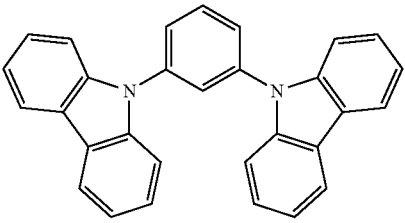
501
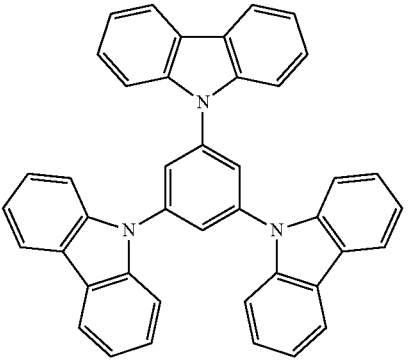
502
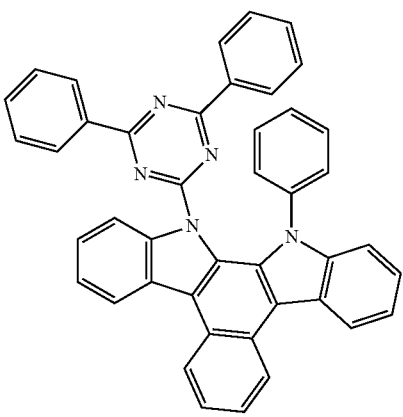
503

504

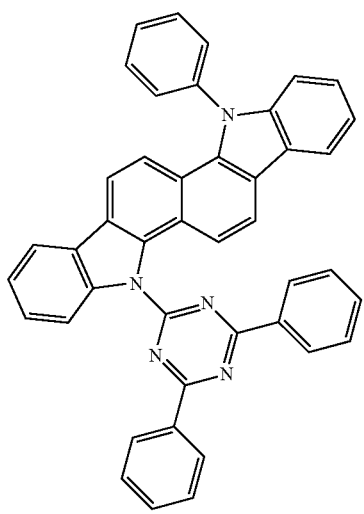

505

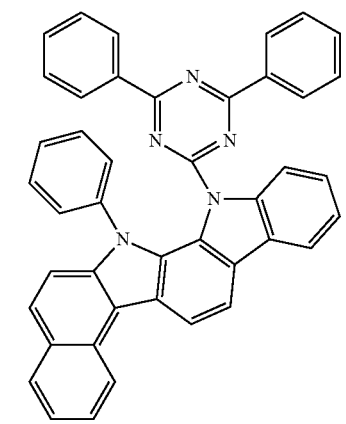

506

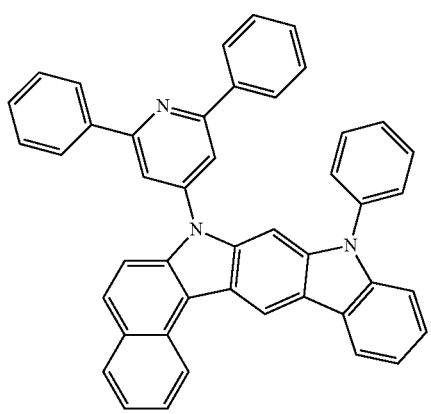

507

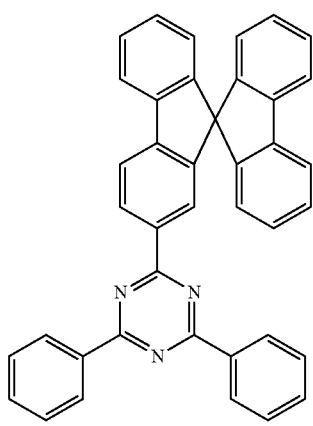

508

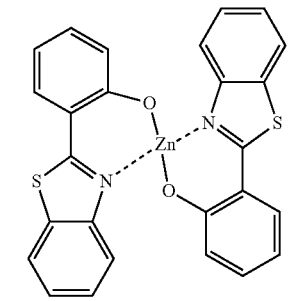

509

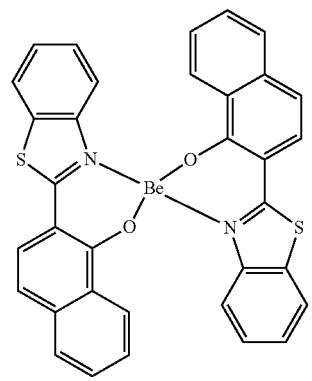

Alternatively, the host may be an anthracene-based compound represented by Formula 400 below.

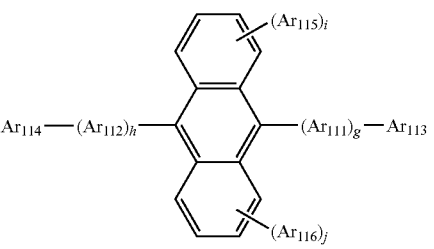

Formula 400

In Formula 400, $Ar_{111}$ and $Ar_{112}$ are each independently a substituted or unsubstituted $C_6$-$C_{60}$ arylene group; $Ar_{113}$ to $Ar_{116}$ are each independently a substituted or unsubstituted $C_1$-$C_{10}$ alkyl group or a substituted or unsubstituted $C_6$-$C_{60}$ aryl group; and g, h, i and j are each independently an integer from 0 to 4.

For example, in Formula 400, $Ar_{111}$ and $Ar_{112}$ may be each independently: a phenylene group, a naphthylene group, a phenanthrenylene group, or a pyrenylene group; or a phenylene group, a naphthylene group, a phenathrenylene group, a fluorenyl group, or a pyrenylene group, each substituted with at least one selected from the group consisting of a phenyl group, a naphthyl group, and an anthryl group, but are not limited thereto.

In Formula 400, g, h, i, and j are each independently 0, 1, or 2.

In Formula 400, $Ar_{113}$ to $Ar_{116}$ may be each independently selected from the group consisting of: a $C_1$-$C_{10}$ alkyl group substituted with at least one selected from the group consisting of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, or a fluorenyl group, each substituted with at least one selected from the group consisting of a deuterium atom, a halogen atom, a hydroxyl group, a cyano group, a nitro group, an amino group, an amidino group, hydrazine, hydrazone, a carboxyl (carboxylic acid) group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{50}$ alkoxy group, a phenyl group, a naphthyl group, an anthryl group, a pyrenyl group, a phenanthrenyl group, and a fluorenyl group; and

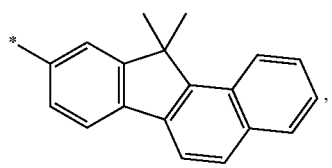 [SMILES: *c1ccc2c(c1)C(C)(C)c1c-2ccc2ccccc12]

without being limited thereto.

For example, the anthracene-based compound represented by Formula 400 may be one of the following compounds, but is not limited thereto.

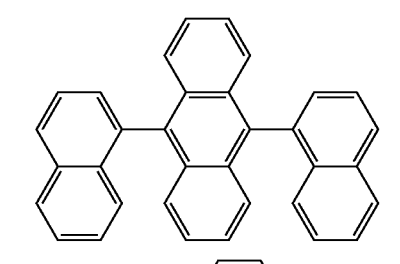

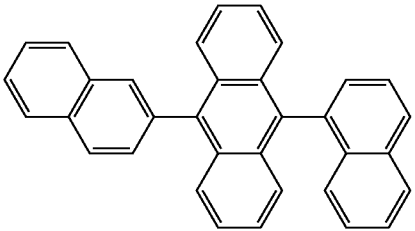

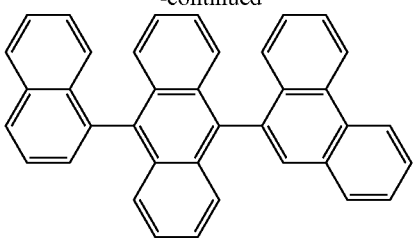

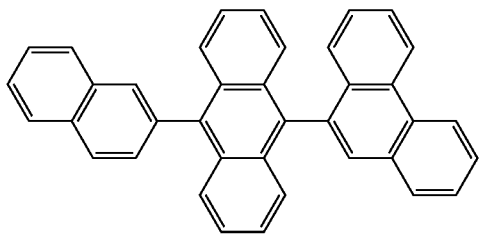

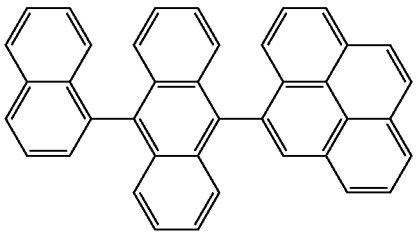

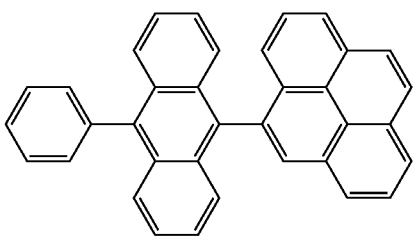

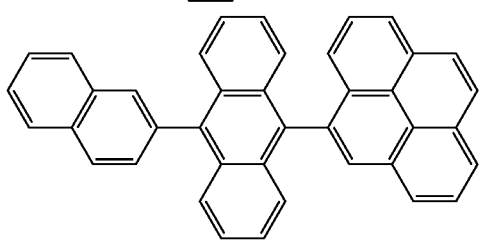

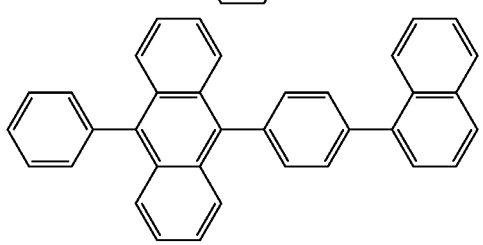

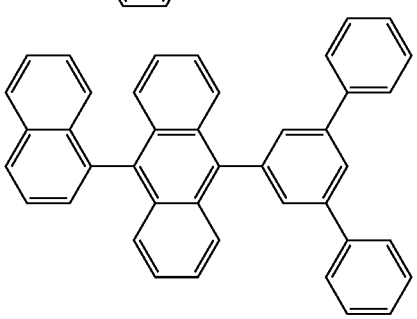

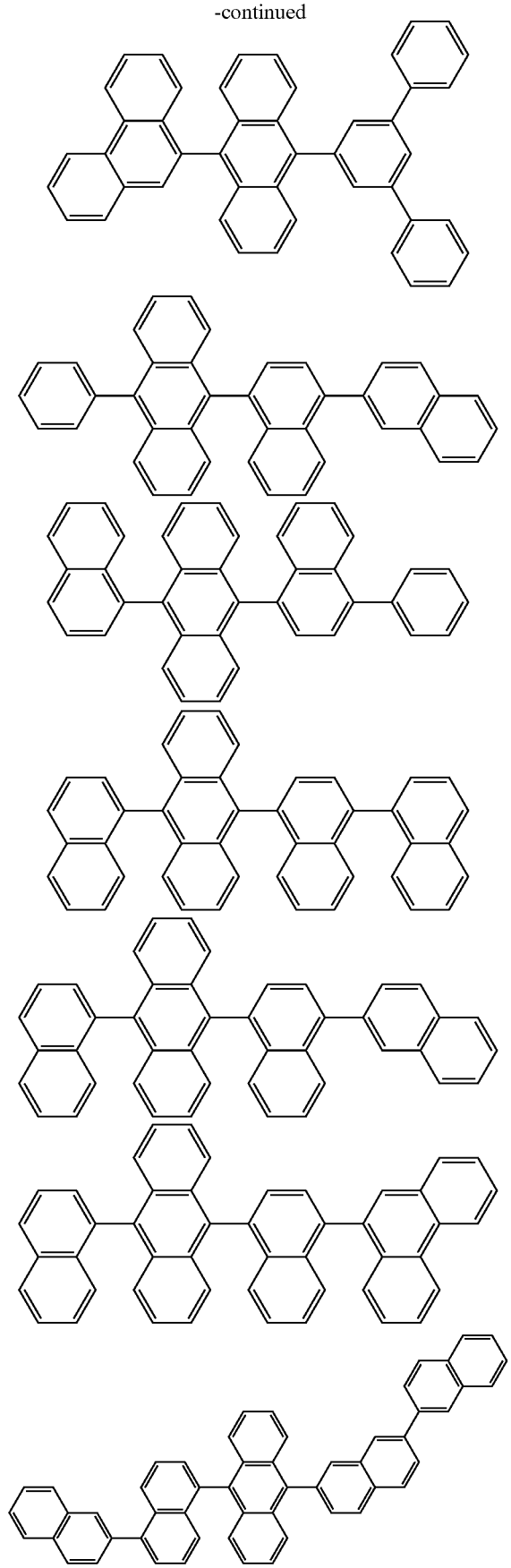
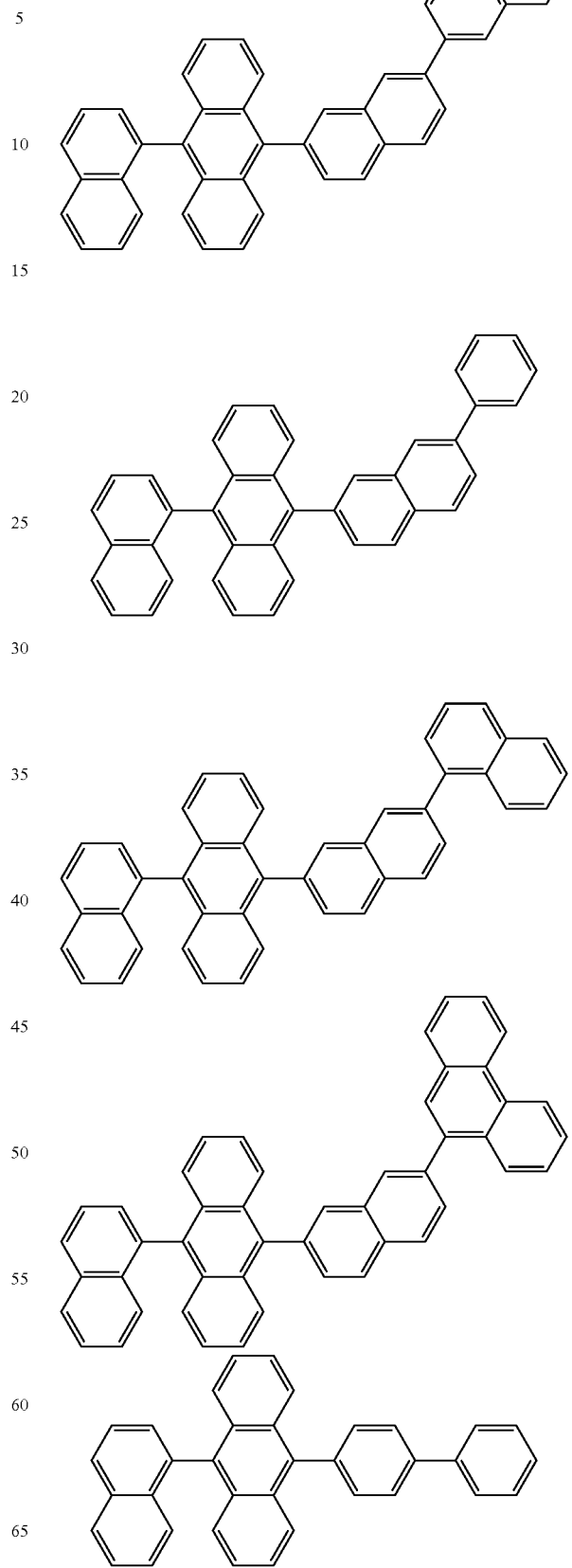

-continued
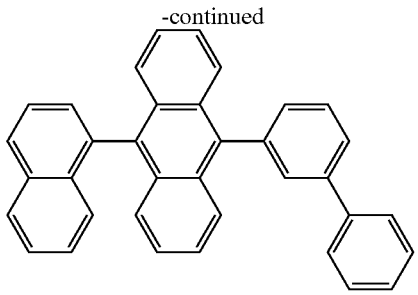
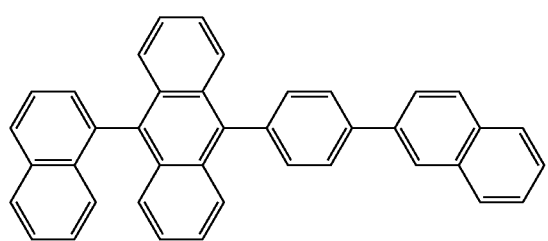
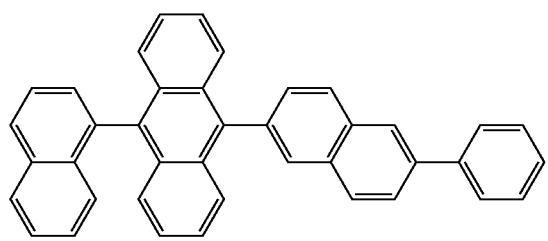
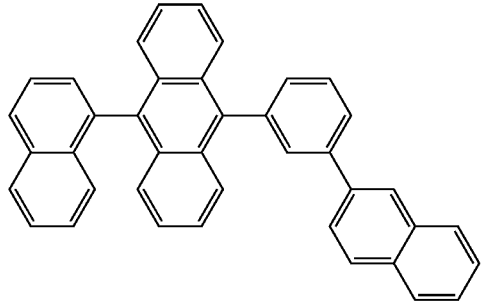
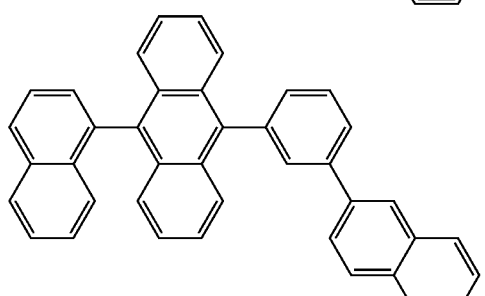
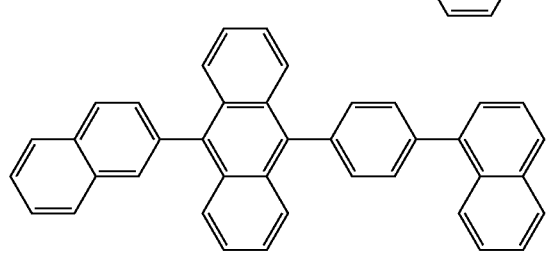
-continued
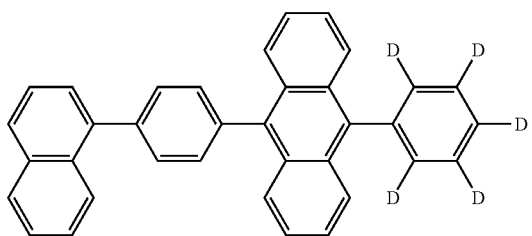
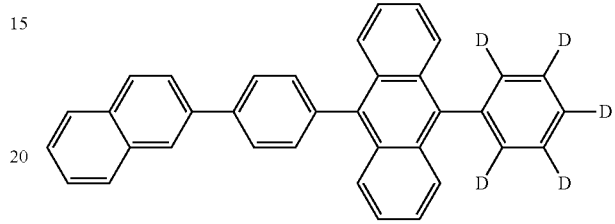
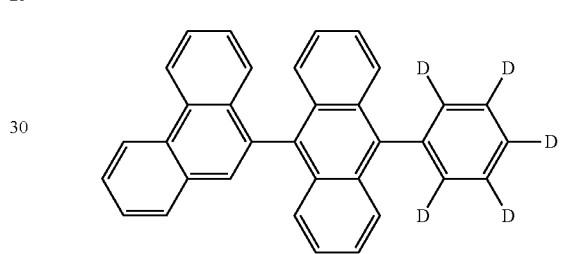
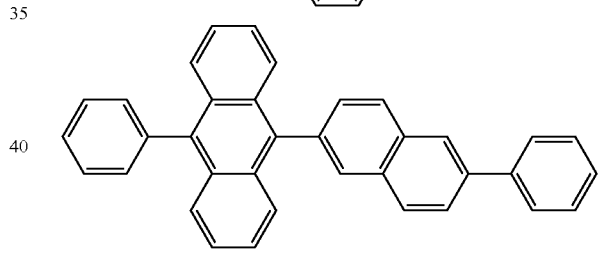
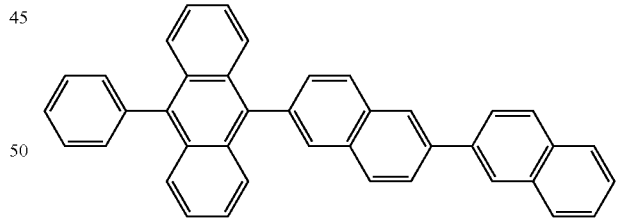
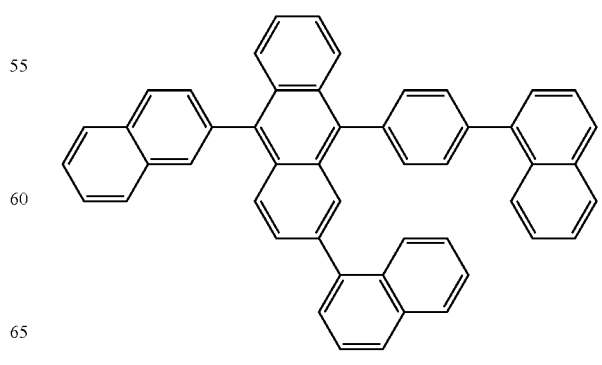

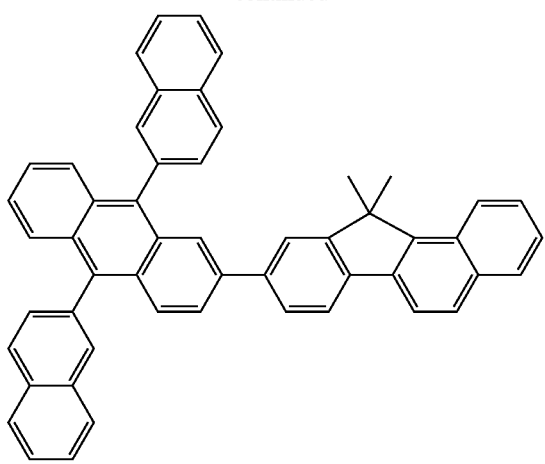
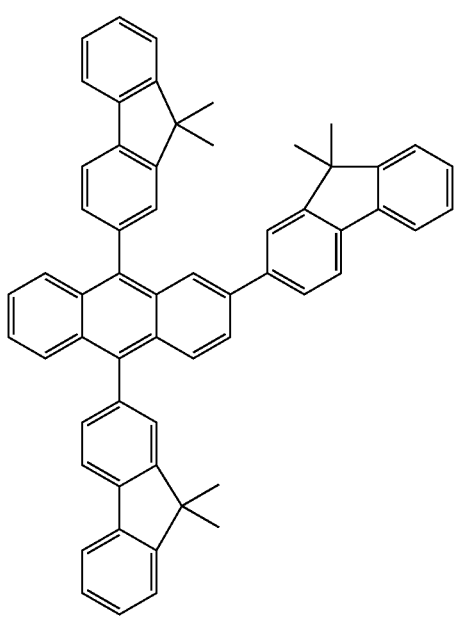
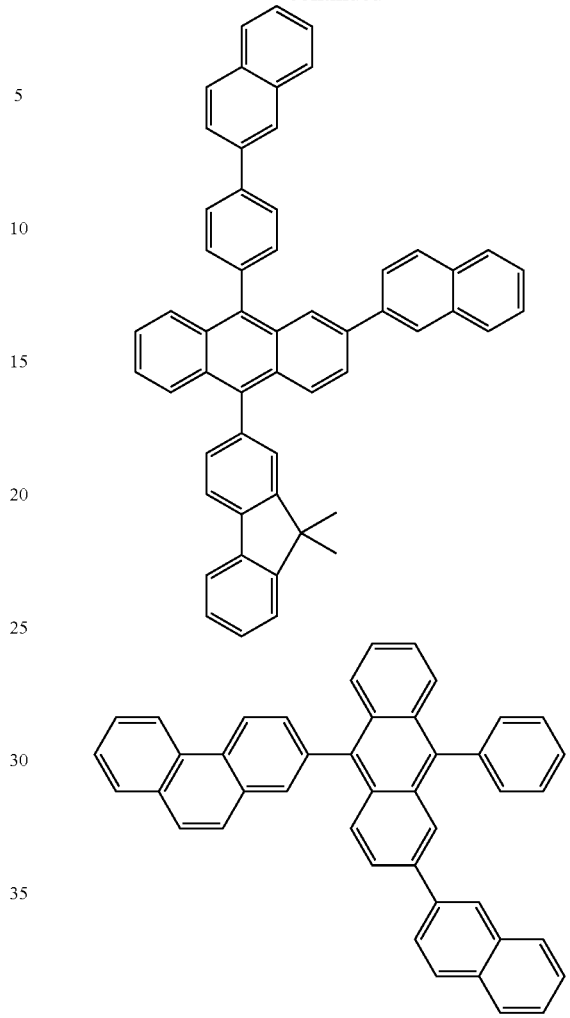

Alternatively, as the host, an anthracene-based compound represented by Formula 401 below may be used (utilized).

Formula 401

$$\text{[structure with Ar}_{122}, \text{Ar}_{123}, (\text{Ar}_{124})_l, (\text{Ar}_{125})_k, \text{Ar}_{126}, \text{Ar}_{127}\text{]}$$

In Formula 401, $Ar_{122}$ to $Ar_{125}$ are defined as described above with reference to $Ar_{113}$ of Formula 400.

In Formula 401, $Ar_{126}$ and $Ar_{127}$ may be each independently a $C_1$-$C_{10}$ alkyl group, such as a methyl group, an ethyl group, or a propyl group.

In Formula 401, k and l may be each independently an integer from 0 to 4. For example, k and l may be 0, 1, or 2, respectively.

For example, the anthracene-based compound represented by Formula 401 may be one of the following compounds, but is not limited thereto.

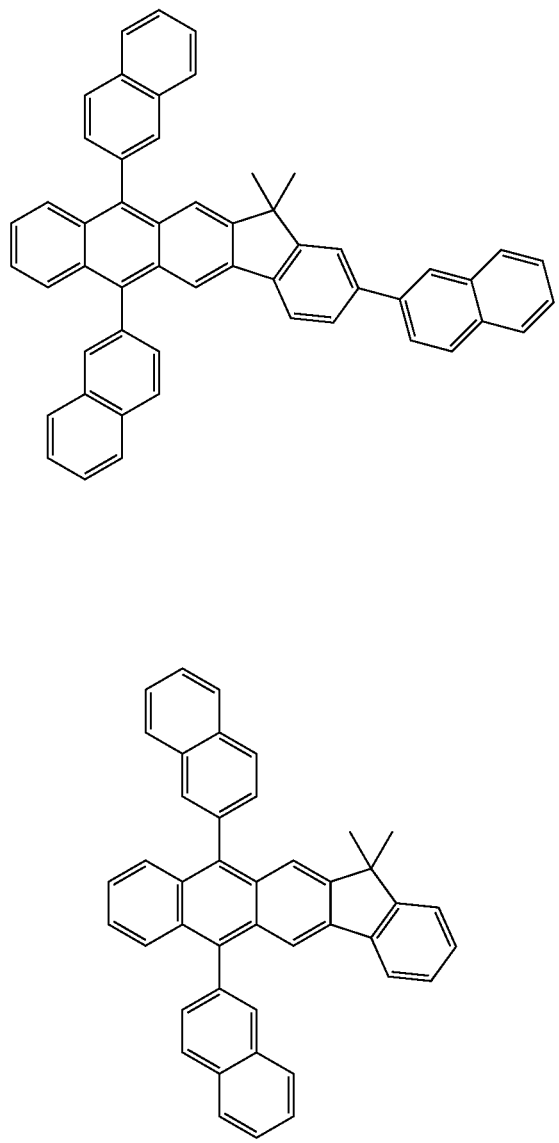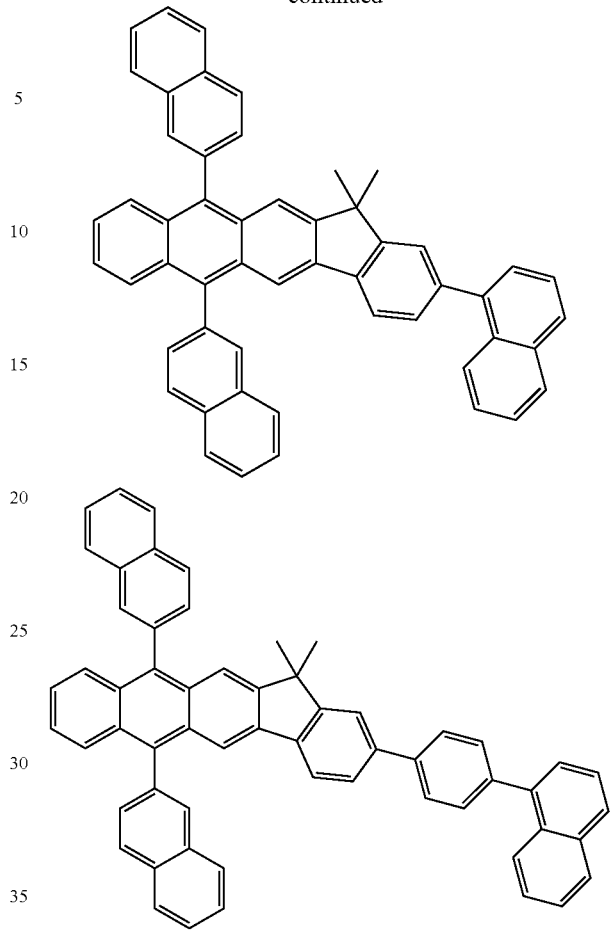
If the organic light-emitting device is a full-color organic light-emitting device, the EML may be patterned into a red EML, a green EML, and a blue EML.
Here, at least one of the red, green, and blue EMLs may include the following dopant (ppy=phenylpyridine).
For example, the following compounds may be used (utilized) as a blue dopant, without being limited thereto.
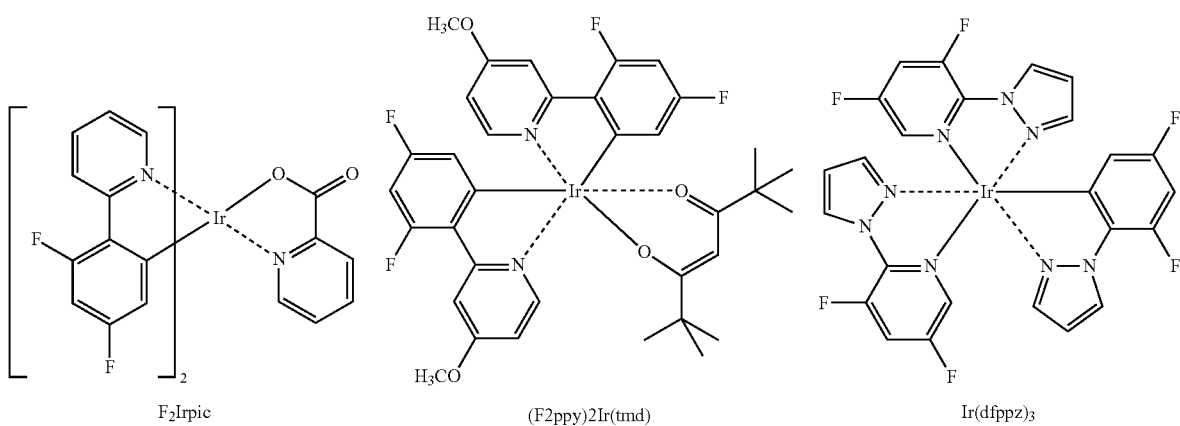

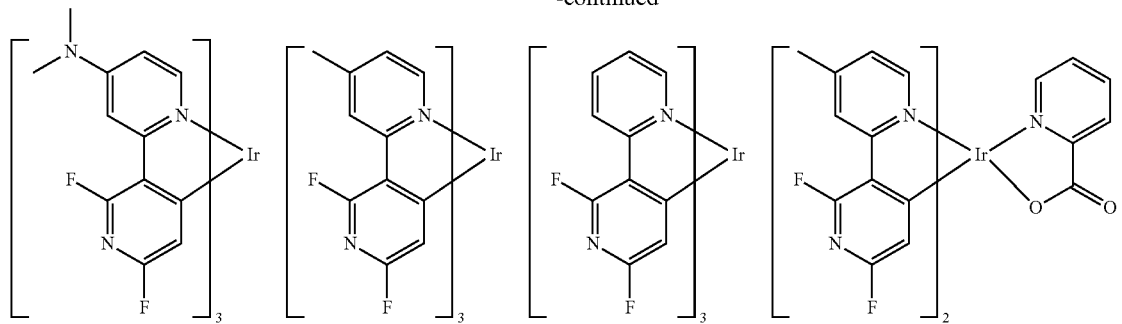
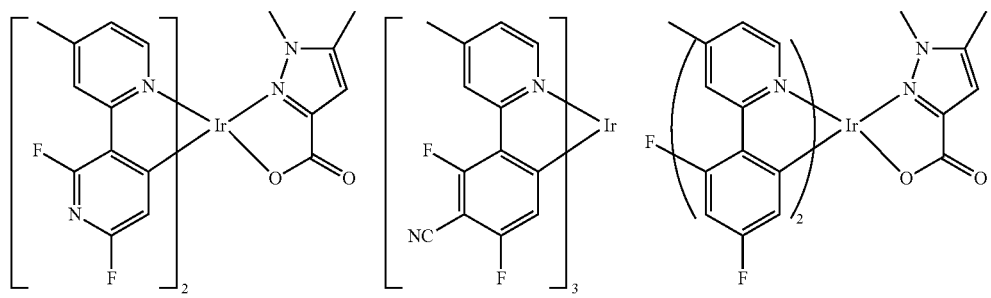
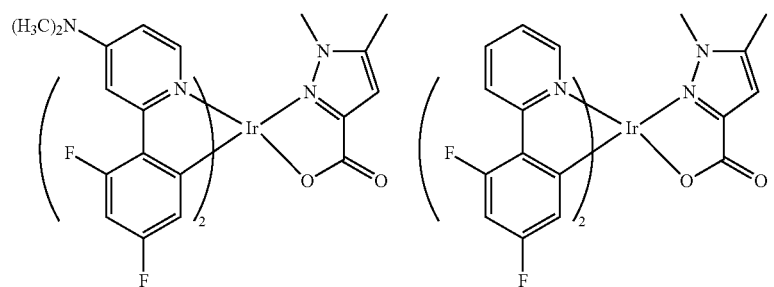
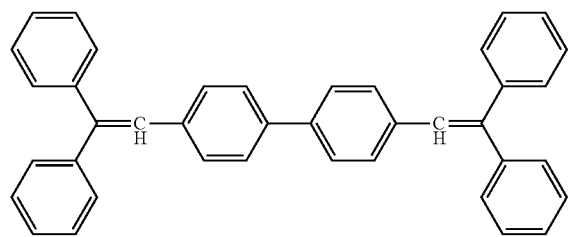
DPVBi

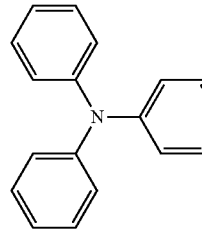
DPAVBi
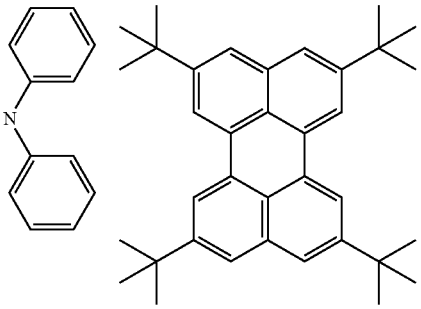
TBPe
For example, the following compounds may be used (utilized) as a red dopant, without being limited thereto.
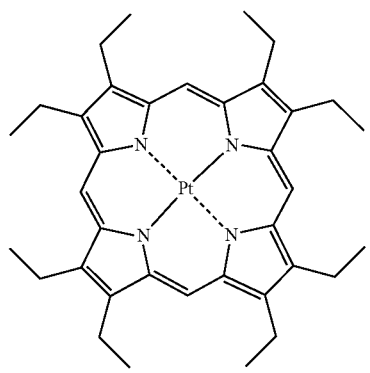
PtOEP
-continued
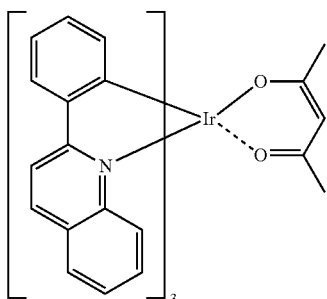
Ir(pq)₂(acac)
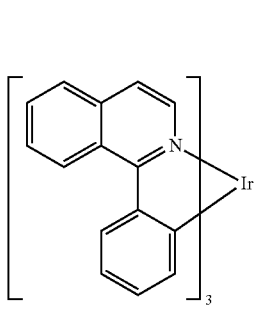
Ir(piq)₃
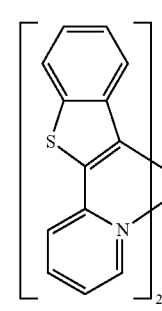
Btp₂Ir(acac)
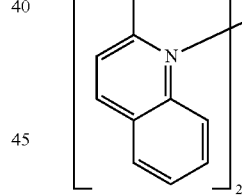
Ir(2-phq)₃
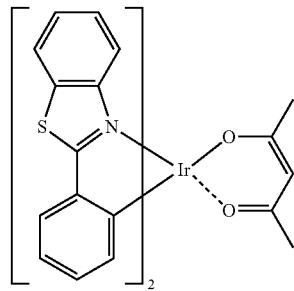
Ir(BT)₂(acac)
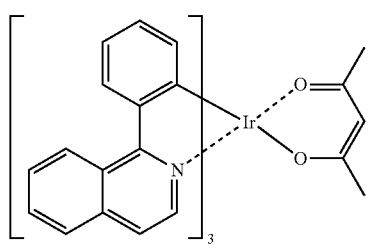
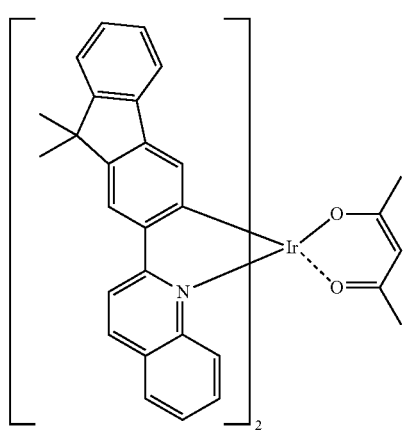
Ir(flq)₂(acac)

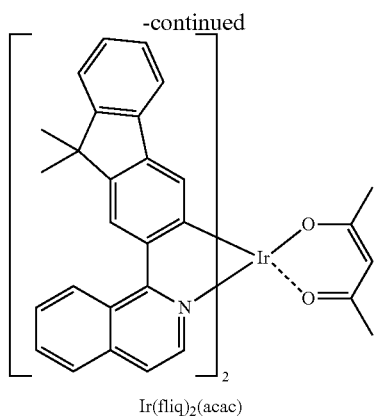
Ir(fliq)₂(acac)
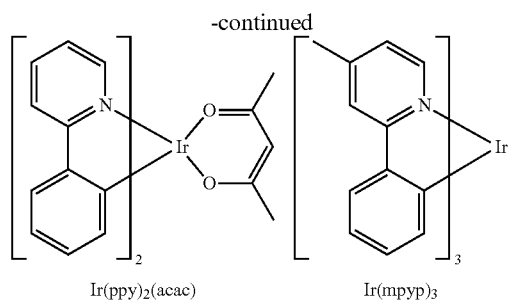
Ir(ppy)₂(acac)  Ir(mpyp)₃
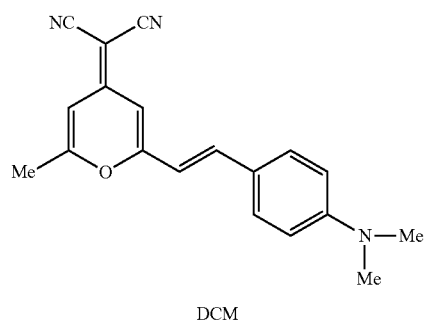
DCM
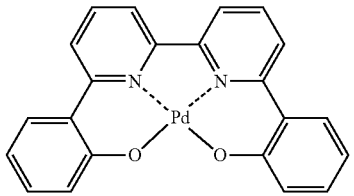
C545T
Here, the dopant used (utilized) in the EML may be a Pd-complex or a Pt-complex, such as those represented by the following chemical structures D1 to D50, without being limited thereto.
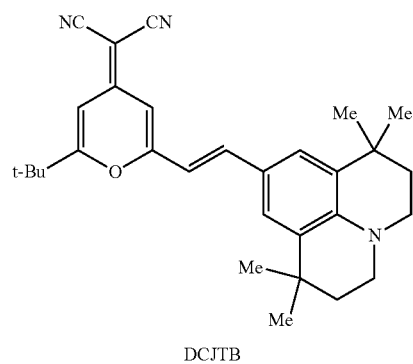
DCJTB
For example, the following compounds may be used (utilized) as a green dopant, without being limited thereto.
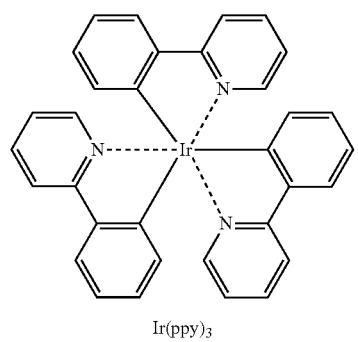
Ir(ppy)₃
D1
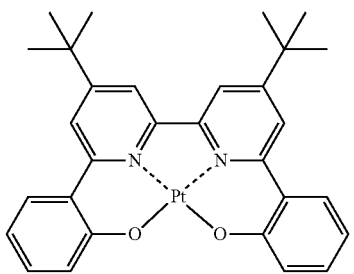
D2
D3
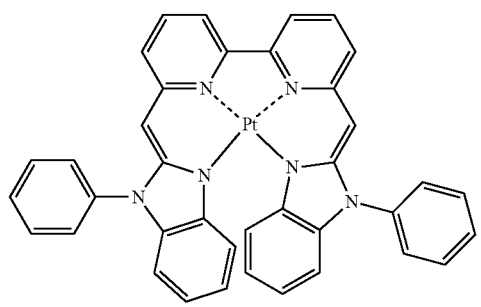

-continued
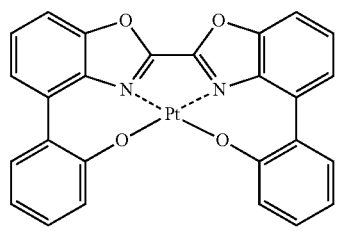
D4
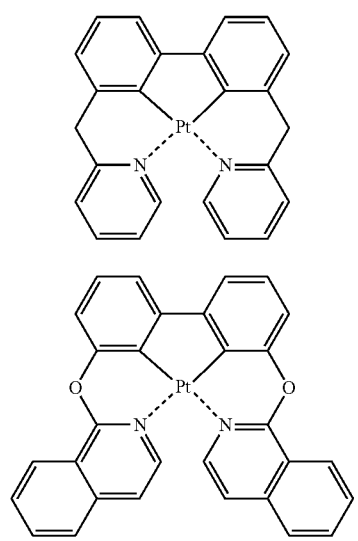
D5
D6
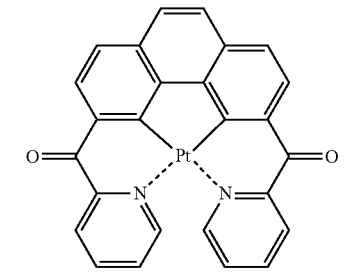
D7
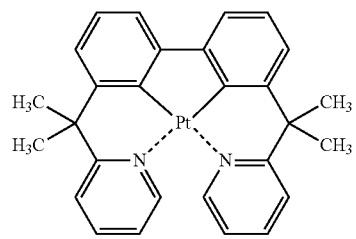
D8
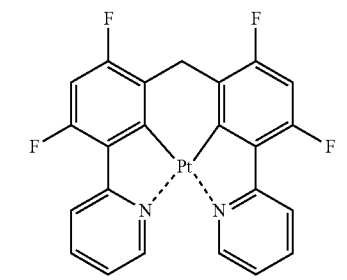
D9
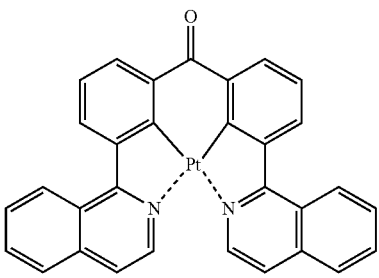
D10
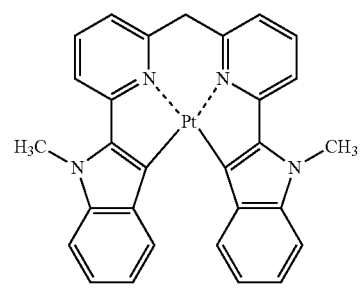
D11
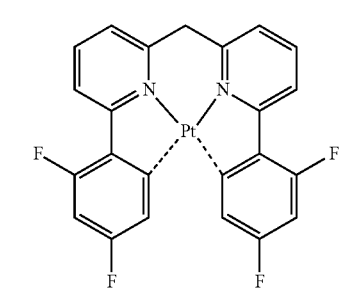
D12
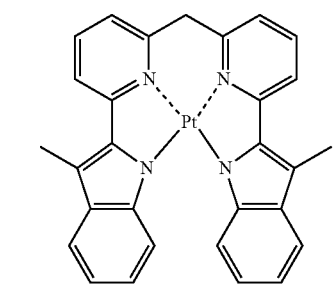
D13
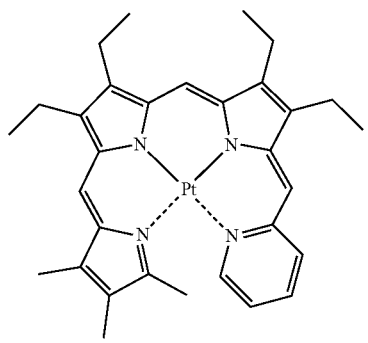
D14

-continued
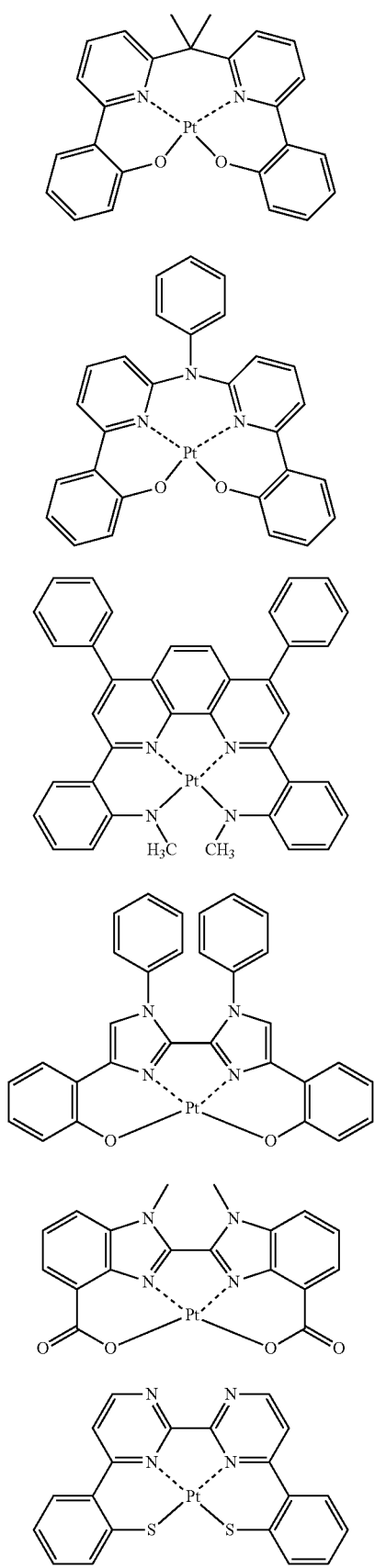
D15
D16
D17
D18
D19
D20
-continued
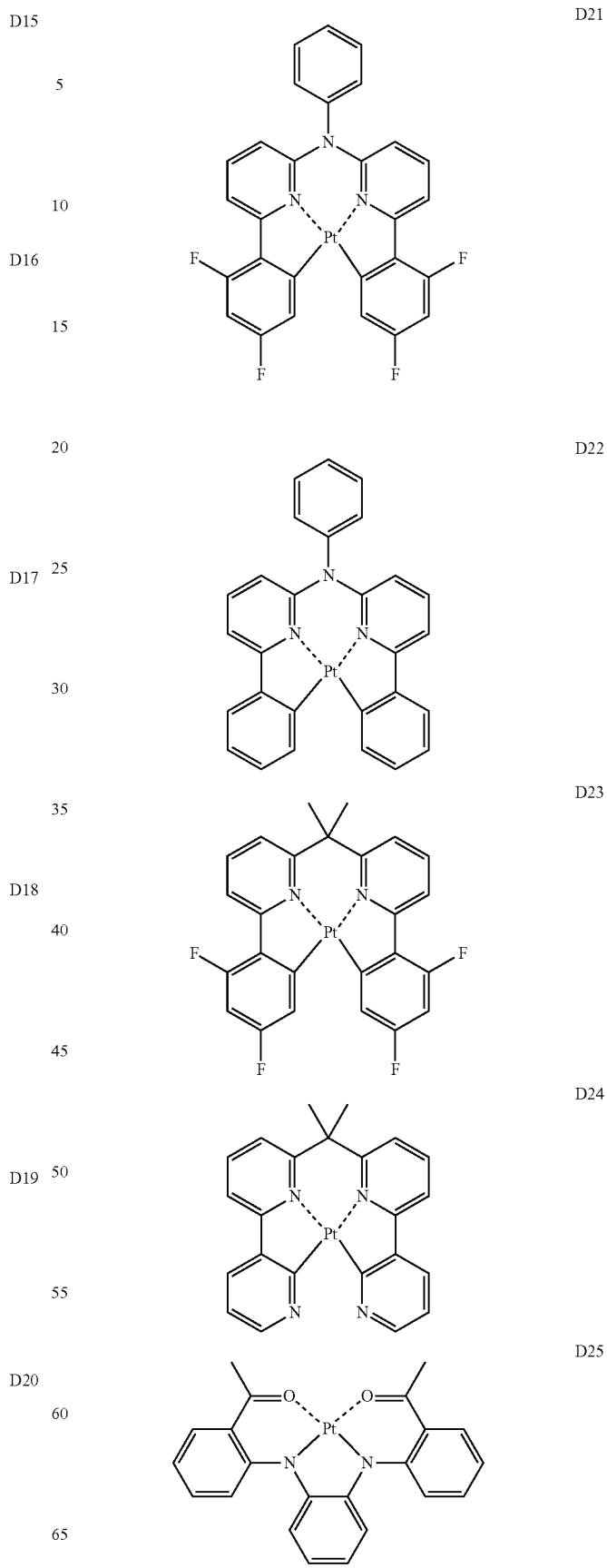
D21
D22
D23
D24
D25

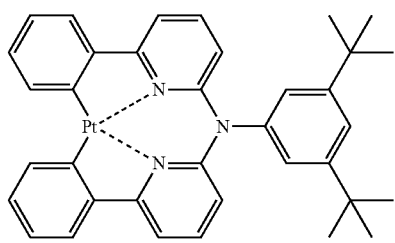
D26
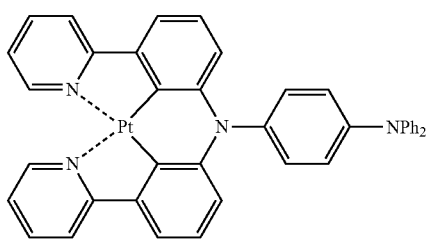
D32
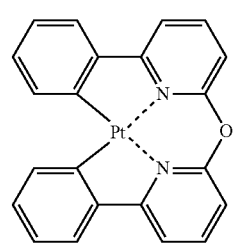
D27
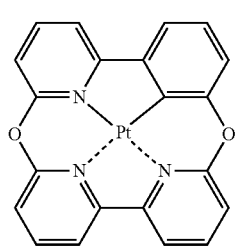
D33
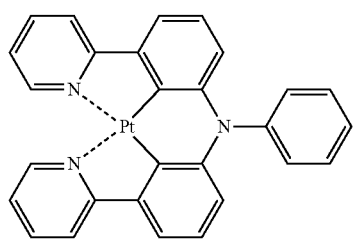
D28
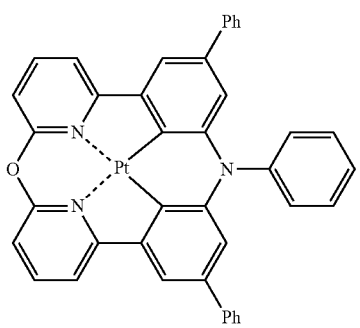
D34
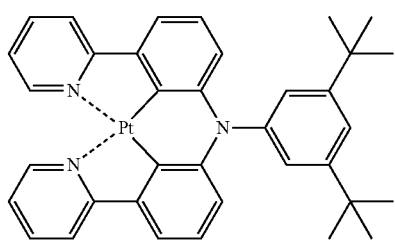
D29
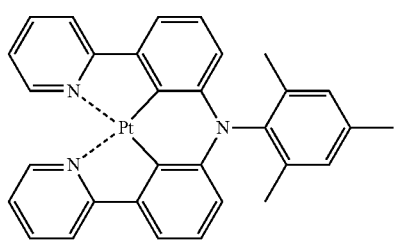
D30
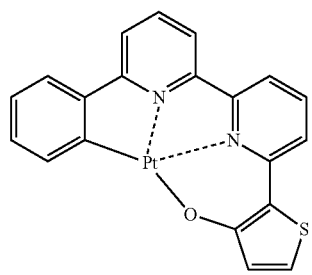
D35
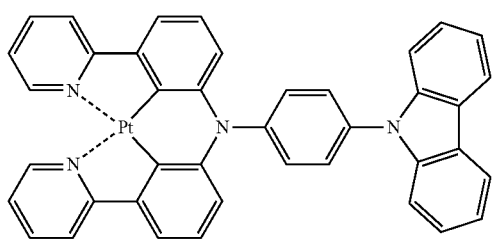
D31
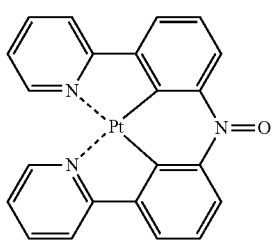
D36

-continued
D37
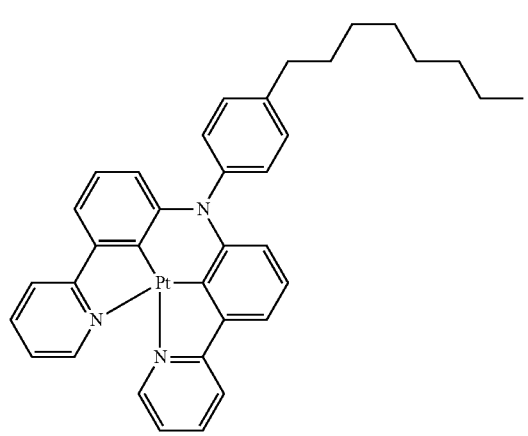
D38
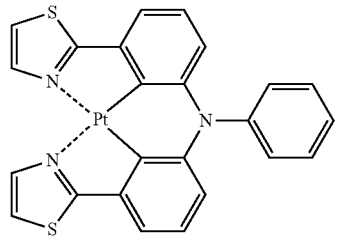
D39
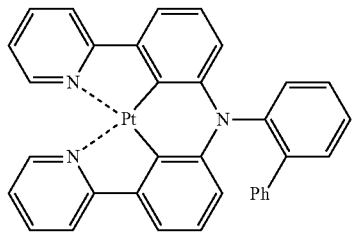
D40
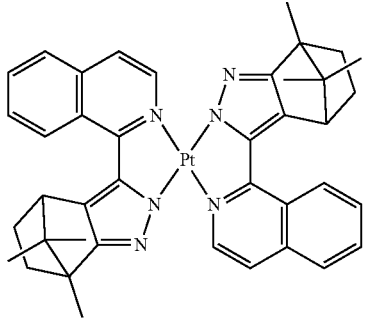
D41
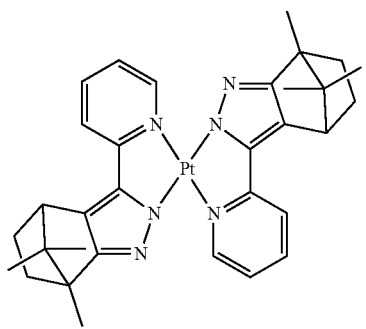
-continued
D42
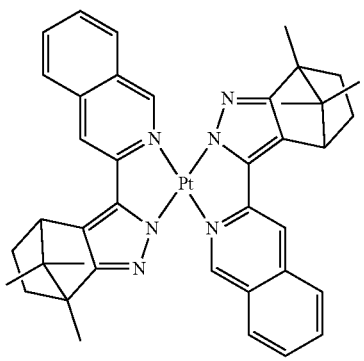
D43
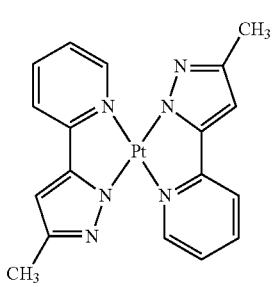
D44
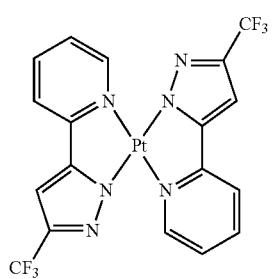
D45
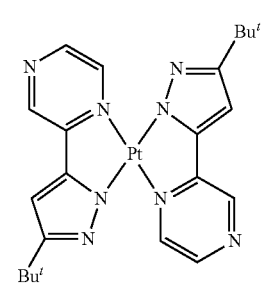
D46
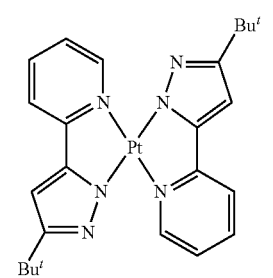

-continued

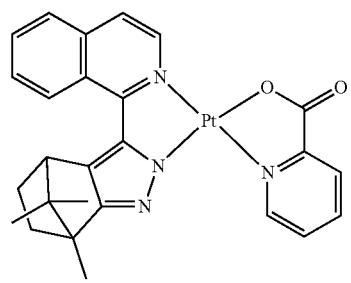
D47

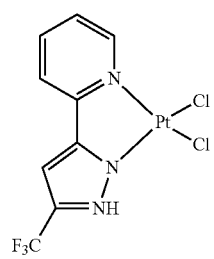
D48

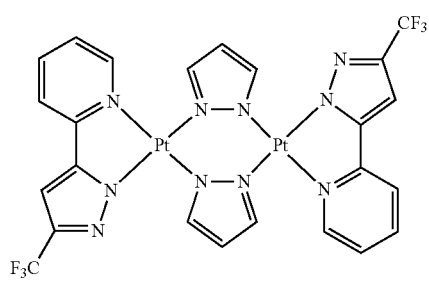
D49

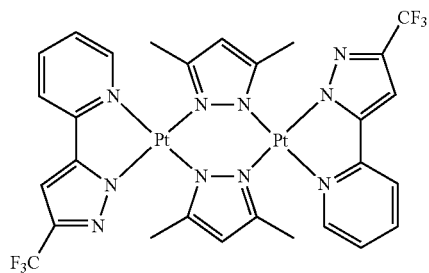
D50

In addition, the dopant used (utilized) in the EML may be an Os-complex, such as those represented by the following chemical structures, without being limited thereto.

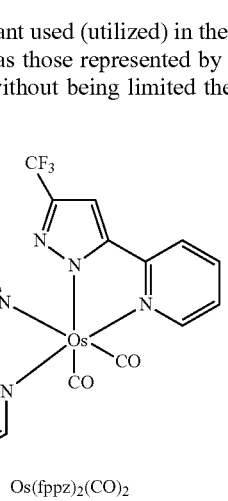
Os(fppz)₂(CO)₂

-continued

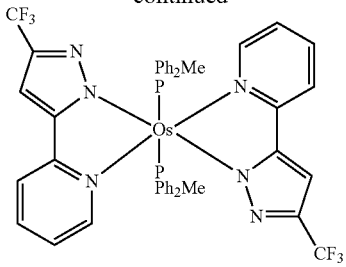
Os(fppz)₂(PPh₂Me)₂

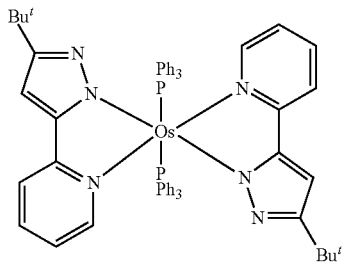
Os(bppz)₂(PPh₃)₂

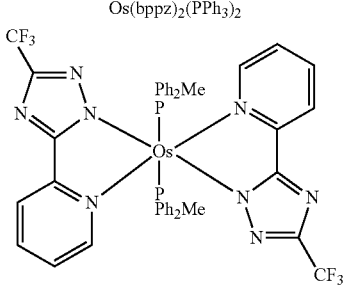
Os(fptz)₂(PPh₂Me)₂

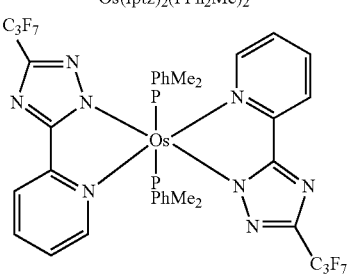
Os(hptz)₂(PPhMe₂)₂

If the EML includes a host and a dopant, the amount of the dopant may be in the range of about 0.01 to about 15 parts by weight based on 100 parts by weight of the host, without being limited thereto.

The thickness of the EML may be in the range of about 100 Å to about 1000 Å, for example, about 200 Å to about 600 Å. In one embodiment, when the thickness of the EML is within this range, the EML has an excellent light emitting ability without a substantial increase in driving voltage.

Then, the ETL may be formed on the EML by vacuum deposition, spin coating, casting, or the like. When the ETL is formed using (utilizing) vacuum deposition or spin coating, the deposition and coating conditions may be similar to those for formation of the HIL, although the deposition and coating conditions may vary according to a compound that is used (utilized) to form the ETL.

The electron transporting material serves to stably transport electrons injected from the electron injecting electrode (cathode), and the compound represented by Formula 1 or Formula 2 according to an embodiment of the present invention or any suitable electron transporting material may be used (utilized) to form the ETL.

Examples of suitable electron transporting materials include quinoline derivatives, such as tris-(8-quinolinorate) aluminum (Alq₃), TAZ, Balq, beryllium bis(benzoquinoli-10-notate) (Balq), ADN, Compound 201, and Compound 202, without being limited thereto.

Compound 201

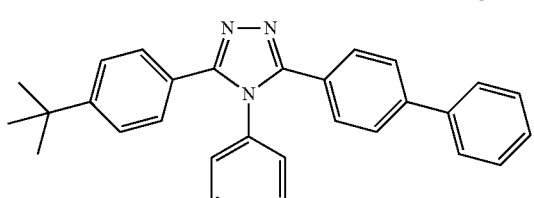

TAZ

Compound 202

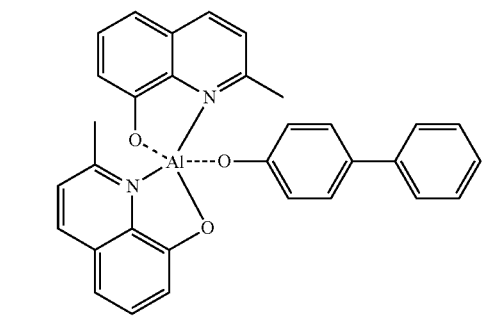

BAlq

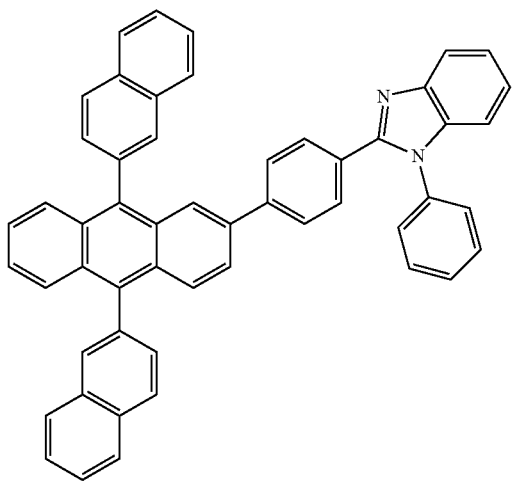

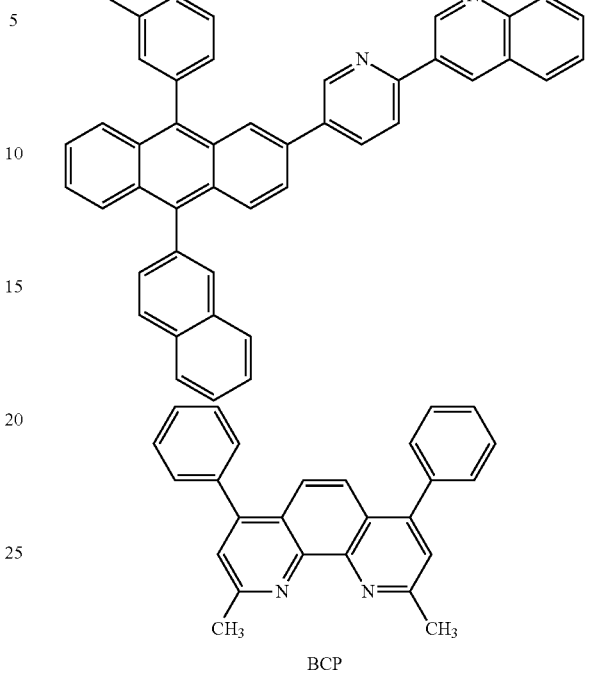

BCP

The thickness of the ETL may be in the range of about 100 Å to about 1,000 Å, for example, about 150 Å to about 500 Å. In one embodiment, when the thickness of the ETL is within the range described above, the ETL has an excellent electron transporting ability without a substantial increase in driving voltage.

Alternatively, the ETL may further include a metal-containing material in addition to suitable electron transporting organic compounds.

The metal-containing material may include a Li complex. Examples of the Li complex include lithium quinolate (LiQ) or Compound 203 below, without being limited thereto.

Compound 203

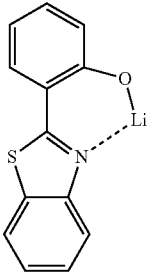

In addition, the EIL may be formed on the ETL using (utilizing) any suitable material that allows electrons to be easily injected from the cathode.

As a material used (utilized) for forming the EIL, the compound represented by Formula 1 or Formula 2 according to an embodiment of the present invention or any suitable material such as LiF, NaCl, CsF, Li₂O, or BaO may be used (utilized). The conditions for deposition of the EIL are similar to those for formation of the HIL, although the deposition conditions may vary according to a material that is used (utilized) to form the EIL.

The thickness of the EIL may be in the range of about 1 to about 100 Å, for example, in the range of about 3 to about 90 Å. In one embodiment, when the thickness of the EIL is within this range, the EIL may have an excellent electron injecting ability without a substantial increase in driving voltage.

A second electrode may be disposed on the organic layer. The second electrode may be a cathode, which is an electron injecting electrode. A metal used (utilized) to form the second electrode may be a low work function metal, an alloy, an electrically conductive compound, or a mixture thereof. For example, the second electrode may be a transmissive electrode formed of lithium (Li), magnesium (Mg), aluminum (Al), Al—Li, calcium (Ca), Mg—In, or Mg—Ag in a thin film. Here, in order to manufacture a top-emission organic light-emitting device, a transmissive electrode formed of ITO or IZO may be used (utilized), and various modifications may be applied thereto.

The organic light-emitting device is described with reference to the drawing, but is not limited thereto.

In addition, when a phosphorescent dopant is used (utilized) to form the EML, an HBL may be formed between the ETL and the EML or between the E-functional layer and the EML by using (utilizing) vacuum deposition, spin coating, casting, LB deposition, or the like, in order to prevent diffusion of triplet excitons or holes into the ETL. When the HBL is formed using (utilizing) vacuum deposition or spin coating, the conditions for deposition and coating may be similar to those for the formation of the HIL, although the conditions for deposition and coating may vary according to the material that is used (utilized) to form the HBL. Any suitable hole blocking material may be used (utilized). Examples of suitable hole blocking materials include an oxadiazole derivative, a triazole derivative, and a phenanthroline derivative. For example, BCP may be used (utilized) as the hole blocking material.

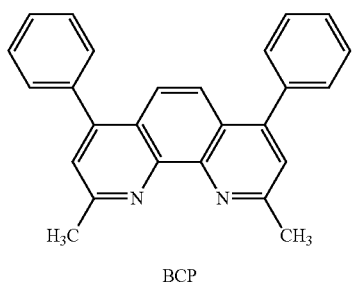 [SMILES: Cc1cc(-c2ccccc2)c2ccc3c(-c4ccccc4)cc(C)nc3c2n1 ; "BCP"]

BCP

The thickness of the HBL may be in a range of about 20 to about 1,000 Å, for example, about 30 to about 300 Å. In one embodiment, when the thickness of the HBL is within this range, the HBL may have an excellent hole blocking ability without a substantial increase in driving voltage.

The organic light-emitting device according to an embodiment of the present invention may be mounted in various kinds of flat panel display apparatus, such as a passive matrix organic light-emitting display apparatus or an active matrix organic light-emitting display apparatus. For example, when the organic light-emitting device is applied to an active matrix organic light-emitting display apparatus, the first electrode disposed on the substrate may function as a pixel electrode, electrically connected to a source electrode or a drain electrode of a thin-film transistor (TFT) thereof.

Moreover, the organic light-emitting device may also be applied to a flat panel display apparatus having a double-sided screen.

Furthermore, the organic layer of the organic light-emitting device may be formed of the compound represented by Formula 1 or Formula 2 by deposition or a wet method of coating a solution of the compound.

Hereinafter, one or more embodiments will be described in more detail with reference to the following synthesis examples and examples. These synthesis examples and examples are not intended to limit the purpose and scope of the one or more embodiments of the present invention.

EXAMPLES

Synthesis of Compound 1

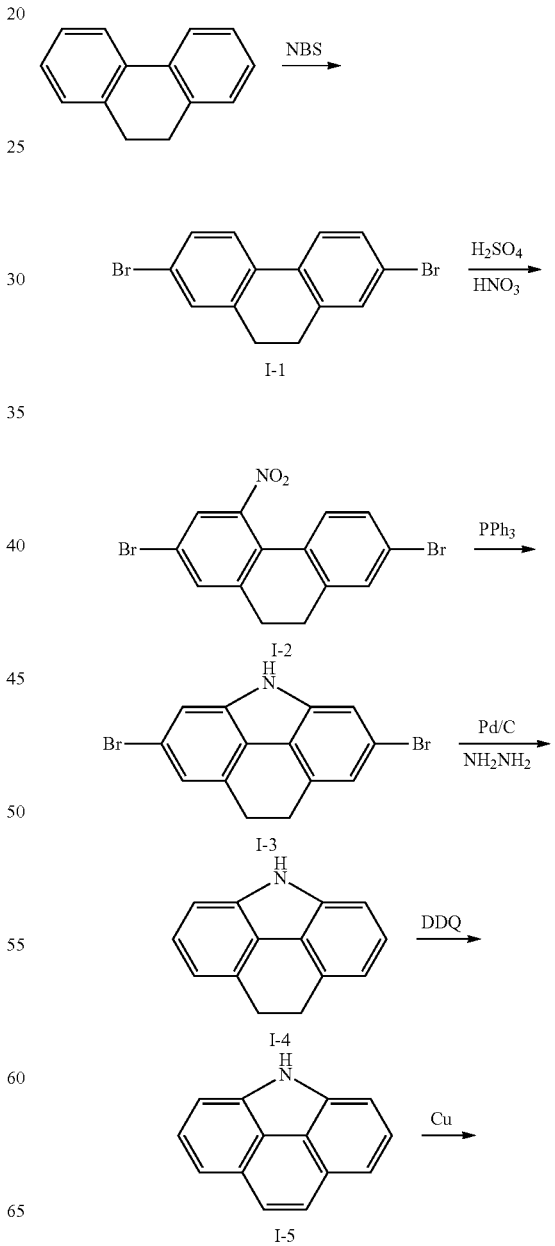

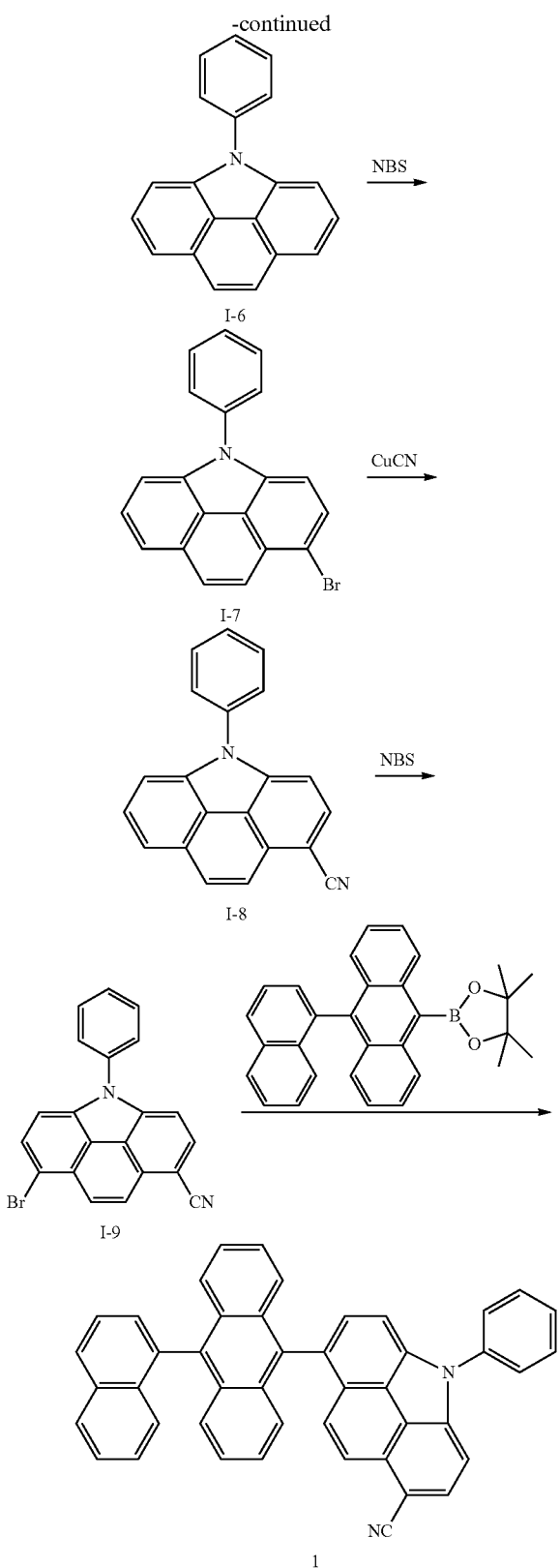

1) Synthesis of Intermediate I-1

10.0 g (55.4 mmol) of 9,10-dihydrophenanthrene, 21.8 g (121.0 mmol) of N-bromosuccinimide, and 0.5 g (2.7 mmol) of p-TsOH were dissolved in 30 mL of acetonitrile, and the reaction mixture was stirred at 50° C. for 12 hours. The reaction mixture was cooled to room temperature, and then stirred for 30 minutes to precipitate the crystals. The crystals collected through reduced pressure filtering were washed with methanol to produce 8.42 g of gray crystals of Intermediate I-1 (yield: 45%). The produced compound was identified using (utilizing) LC-MS. $C_{14}H_{10}Br_2$ M$^+$ 336.

2) Synthesis of Intermediate I-2

5.0 g (15.0 mmol) of Intermediate I-1 was completely dissolved in 50 mL of dichloromethane, and 1.7 g (30.0 mmol) of nitric acid was added thereto at room temperature. Then, 1.5 g (15.0 mmol) of sulfuric acid was slowly added thereto dropwise, and the reaction mixture was stirred at 30° C. for 6 hours. After the reaction was terminated, the reaction mixture was cooled to room temperature. Then, 50 mL of methanol was added thereto, and the reaction mixture was stirred over 2 hours to precipitate the crystals. The crystals collected through reduced pressure filtering were washed with methanol to produce 5.2 g of yellow crystals of Intermediate I-2 (yield: 90%). The produced compound was identified using (utilizing) LC-MS. $C_{14}H_9Br_2NO_2$ M$^+$ 381.9.

3) Synthesis of Intermediate I-3

4.6 g (12.0 mmol) of Intermediate I-2 was dissolved in 30 mL of o-dichlorobenzene, and the reaction mixture was heated to completely dissolve Intermediate I-2. 4.7 g (18.0 mmol) of triphenylphosphine was added thereto, and the reaction mixture was stirred at 180° C. over 3 hours. The reaction mixture was cooled to room temperature, and the solvent was evaporated. The remainder was purified using (utilizing) silica gel column chromatography and washed with methanol to produce 2.9 g of white crystals of Intermediate I-3 (yield: 70%). The produced compound was identified using (utilizing) LC-MS. $C_{14}H_9Br_2N$ M$^+$ 349.9.

4) Synthesis of Intermediate I-4

10 g (28.5 mmol) of Intermediate I-3 and 0.03 g (0.28 mmol) of Pd/C (10%) were dissolved in 100 mL of ethanol at room temperature, and the reaction mixture was heated to 50° C. Then, 5.48 g (171 mmol) of hydrazine was added thereto dropwise, and the reaction mixture was stirred over 24 hours. The reaction mixture was cooled to room temperature and washed with acetone. 100 mL of ice water was added thereto to produce 3.63 g of white crystals of Intermediate I-4 (yield: 66%). The produced compound was identified using (utilizing) LC-MS. $C_{14}H_{11}N$ M$^+$ 194.1.

5) Synthesis of Intermediate I-5

10 g (51.8 mmol) of Intermediate I-4 was dissolved in 100 mL of toluene in an oxygen atmosphere, and 1.57 g (7.6 mmol) of 2,3-dichloro-5,6-dicyano-1,4-benzoquinone and 0.52 g (7.6 mmol) of NaNO$_2$ were added thereto at room temperature. The reaction mixture was stirred at 110° C. for 6 hours. After the reaction was terminated, the reaction mixture was cooled to room temperature, and the solvent was evaporated. The remainder was purified using (utilizing) silica gel column chromatography to produce 9.00 g of Intermediate I-5 (yield: 91%). The produced compound was identified using (utilizing) LC-MS. $C_{14}H_9N$ M$^+$ 192.1.

6) Synthesis of Intermediate I-6

9.0 g (47 mmol) of Intermediate I-5, 7.38 g (47 mmol) of bromobenzene, 1.79 g (28.2 mmol) of copper powder, and 9.74 g (70.5 mmol) of K$_2$CO$_3$ were dissolved in 80 mL of o-dichlorobenzene, and the reaction mixture was stirred at 180° C. over 24 hours. The reaction mixture was cooled to room temperature, 60 mL of water was added thereto, and the reaction mixture was subjected to extraction three times with 50 mL of ethyl acetate. An organic layer was collected and dried using (utilizing) magnesium sulfate to evaporate the solvent. The remainder was purified using (utilizing)

silica gel column chromatography to obtain 9.42 g of Intermediate I-6 (Yield: 75%). The produced compound was identified using (utilizing) LC-MS. $C_{20}H_{13}N$: $M^+$ 267.10.

7) Synthesis of Intermediate I-7

9.36 g (35 mmol) of Intermediate I-1 was completely dissolved in 80 mL of $CH_2Cl_2$, and 6.23 g (35 mmol) of N-bromosuccinimide was added to the reaction mixture. Then, the reaction mixture was stirred at room temperature over 12 hours. 60 mL of water was added thereto, and the reaction mixture was subjected to extraction three times with 50 mL of $CH_2Cl_2$. An organic layer was collected and dried using (utilizing) magnesium sulfate to evaporate the solvent. The remainder was recrystallized with methanol to produce 9.69 g of Intermediate I-7 (Yield: 80%). The produced compound was identified using (utilizing) LC-MS. $C_{20}H_{12}BrN$: $M^+$ 345.0.

8) Synthesis of Intermediate I-8

9.69 g (28 mmol) of Intermediate I-7 and 3.76 g (42 mmol) of CuCN were dissolved in 70 mL of DMF, and the reaction mixture was stirred at 150° C. over 24 hours. The reaction mixture was cooled to room temperature, 60 mL of ammonia water and 60 mL of water were added thereto, and the reaction mixture was subjected to extraction three times with 50 mL of $CH_2Cl_2$. An organic layer was collected and dried using (utilizing) magnesium sulfate to evaporate the solvent. The remainder was then purified using (utilizing) silica gel column chromatography to obtain 6.96 g of Intermediate I-8 (Yield: 85%). The produced compound was identified using (utilizing) LC-MS. $C_{21}H_{12}N_2$: $M^+$ 292.1.

9) Synthesis of Intermediate I-9

6.72 g (23 mmol) of Intermediate I-8 was completely dissolved in 80 mL of $CH_2Cl_2$, and 4.09 g (23 mmol) of N-bromosuccinimide was added to the reaction mixture. Then, the reaction mixture was stirred at room temperature over 8 hours. 60 mL of water was added to the reaction mixture, and the reaction mixture was subjected to extraction three times with 50 mL of $CH_2Cl_2$. An organic layer was collected and dried using (utilizing) magnesium sulfate to evaporate the solvent. The remainder was recrystallized with methanol to produce 7.43 g of Intermediate I-9 (Yield: 87%). The produced compound was identified using (utilizing) LC-MS. $C_{21}H_{12}BrN_2$: $M^+$ 370.0.

10) Synthesis of Compound 1

5.57 g (15 mmol) of Intermediate I-9, 6.46 g (15 mmol) of 4,4,5,5-tetramethyl-2-(10-naphthalene-1-yl-anthracene-9-yl)-[1,3,2]dioxaborolane, 0.87 g (0.75 mmol) of $Pd(PPh_3)_4$, and 6.22 g (45 mmol) of $K_2CO_3$ were dissolved in 60 mL of THF and 30 mL of $H_2O$, and the reaction mixture was stirred at 80° C. over 12 hours. The reaction mixture was cooled to room temperature, and the reaction mixture was subjected to extraction three times with 30 mL of water and 30 mL of ethyl acetate. An organic layer was collected and dried using (utilizing) magnesium sulfate to evaporate the solvent. The remainder was then purified using (utilizing) silica gel column chromatography to obtain 6.24 g of Compound 1 (Yield: 70%). The produced compound was identified using (utilizing) MS/FAB and $^1H$ NMR. $C_{45}H_{26}N_2$ cal. 594.21, found 594.20.

Synthesis of Compound 5

6.08 g of Compound 5 was produced with a yield of 68% in the same manner as in the synthesis of Compound 1, except that 3-bromopyridine was used (utilized) instead of bromobenzene in the synthesis of Intermediate I-6. The produced compound was identified using (utilizing) MS/FAB and $^1H$ NMR. $C_{44}H_{25}N_3$ cal. 595.20, found 595.21.

Synthesis of Compound 15

7.42 g of Compound 15 was produced with a yield of 66% in the same manner as in the synthesis of Compound 1, except that 2-chloro-4,6-diphenyl-[1,3,5]triazine was used (utilized) instead of bromobenzene in the synthesis of Intermediate I-6. The produced compound was identified using (utilizing) MS/FAB and $^1H$ NMR. $C_{54}H_{31}N_5$ cal. 749.26, found 749.27.

Synthesis of Compound 21

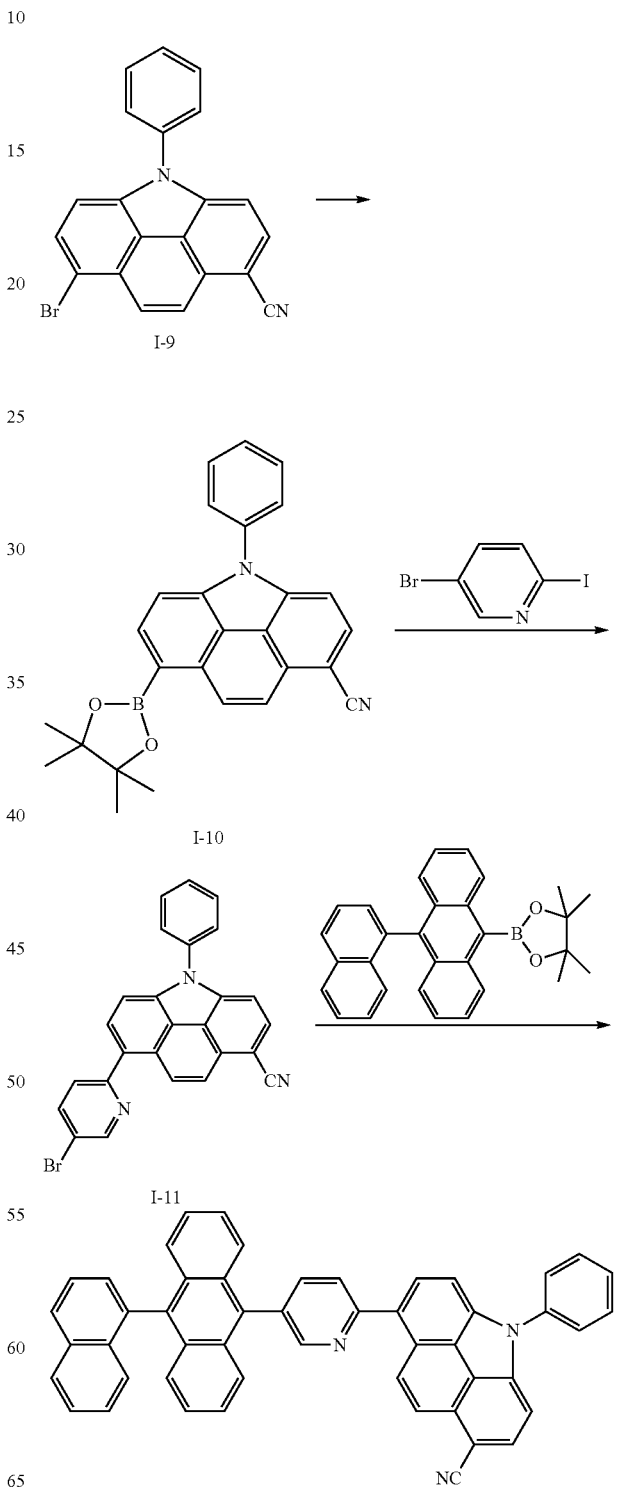

1) Synthesis of Intermediate I-10

7.43 g (20.0 mmol) of Intermediate I-9, 0.81 g (1.0 mmol) of Pd(dppf)$_2$Cl$_2$, and 5.89 g (60.0 mmol) of KOAc were dissolved in 100 mL of DMSO, and the reaction mixture was stirred at 150° C. over 24 hours. The reaction mixture was cooled to room temperature, 100 mL of water was added thereto, and the reaction mixture was subjected to extraction three times with 50 mL of CH$_2$Cl$_2$. An organic layer was collected and dried using (utilizing) magnesium sulfate to evaporate the solvent. The remainder was purified using (utilizing) silica gel column chromatography to obtain 5.69 g of Intermediate I-10 (Yield: 68%). The produced compound was identified using (utilizing) LC-MS. C$_{27}$H$_{23}$BN$_2$O$_2$: M$^+$ 418.2.

2) Synthesis of Intermediate I-11

5.69 g (13.6 mmol) of Intermediate I-10, 3.86 g (13.6 mmol) of 5-bromo-2-iodo-pyridine, 0.79 g (0.68 mmol) of Pd(PPh$_3$)$_4$, and 5.64 g (40.8 mmol) of K$_2$CO$_3$ were dissolved in 60 mL of THF and 30 mL of H$_2$O, and the reaction mixture was stirred at 80° C. over 12 hours. The reaction mixture was cooled to room temperature, and the reaction mixture was subjected to extraction three times with 30 mL of water and 30 mL of ethyl acetate. An organic layer was collected and dried using (utilizing) magnesium sulfate to evaporate the solvent. The remainder was purified using (utilizing) silica gel column chromatography to obtain 4.39 g of Intermediate I-11 (Yield: 72%). The produced compound was identified using (utilizing) LC-MS. C$_{26}$H$_{14}$BrN$_3$: M$^+$ 447.0.

3) Synthesis of Compound 21

4.60 g of Compound 21 was produced with a yield of 70% in the same manner as in the synthesis of Compound 1, except that Intermediate I-11 was used (utilized) instead of Intermediate I-9 in the synthesis of Compound 1. The produced compound was identified using (utilizing) MS/FAB and $^1$H NMR. C$_{50}$H$_{29}$N$_3$ cal. 671.24, found 671.22.

Synthesis of Compound 26

7.55 g of Compound 26 was produced with a yield of 75% in the same manner as in the synthesis of Compound 1, except that 4,4,5,5-tetramethyl-2-[10-(4-phenyl-naphthalene-1-yl)-anthracene-9-yl]-[1,3,2]dioxaborolane was used (utilized) instead of 4,4,5,5-tetramethyl-2-(10-naphthalene-1-yl-anthracene-9-yl)-[1,3,2]diooxaborolane in the synthesis of Compound 1. The produced compound was identified using (utilizing) MS/FAB and $^1$H NMR. C$_{51}$H$_{30}$N$_2$ cal. 670.24, found 670.25.

Synthesis of Compound 43

8.30 g of Compound 43 was produced with a yield of 67% in the same manner as in the synthesis of Compound 1, except that 2,4-diphenyl-6-{4-[10-(4,4,5,5-tetramethyl-[1,3,2]-dioxyborolane-2-yl)-anthracene-9-yl]-naphthalene-1-yl}-[1,3,5]-triazine was used (utilized) instead of 4,4,5,5-tetramethyl-2-(10-naphthalene-1-yl-anthracene-9-yl)[1,3,2]dioxaborolane in the synthesis of Compound 1. The produced compound was identified using (utilizing) MS/FAB and $^1$H NMR. C$_{60}$H$_{35}$N$_5$ cal. 825.29, found 825.30.

Synthesis of Compound 45

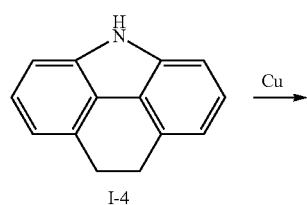

I-4

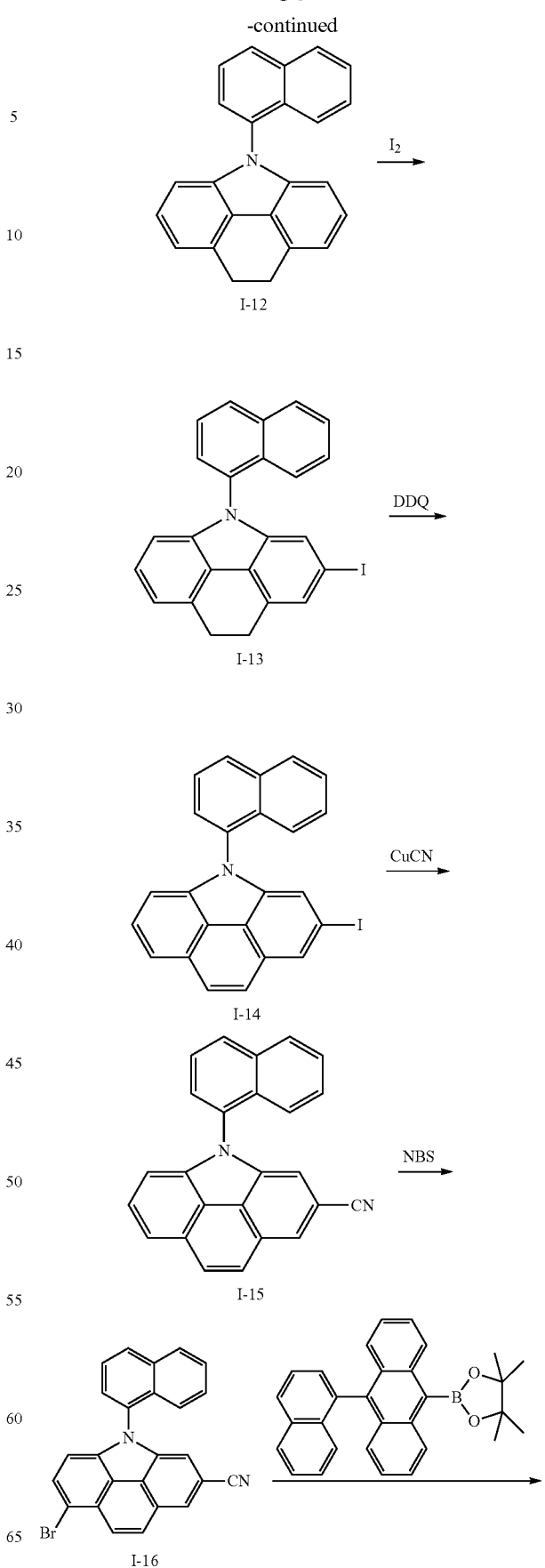

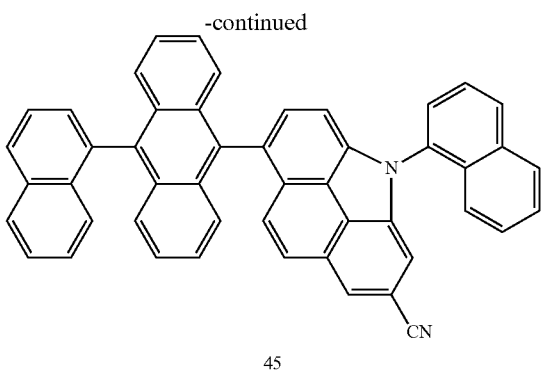

45

1) Synthesis of Intermediate I-12

10.0 g (51.5 mmol) of Intermediate I-4, 10.7 g (51.5 mmol) of bromonaphthalene, 1.96 g (30.9 mmol) of copper powder, and 10.7 g (77.3 mmol) of $K_2CO_3$ were dissolved in 80 mL of o-dichlorobenzene, and the reaction mixture was stirred at 180° C. over 24 hours. The reaction mixture was cooled to room temperature, 60 mL of water was added thereto, and the reaction mixture was subjected to extraction three times with 50 mL of ethyl acetate. An organic layer was collected and dried using (utilizing) magnesium sulfate to evaporate the solvent. The remainder was purified using (utilizing) silica gel column chromatography to obtain 12.0 g of Intermediate I-12 (Yield: 73%). The produced compound was identified using (utilizing) LC-MS. $C_{224}H_{17}N$: $M^+$ 319.1.

2) Synthesis of Intermediate I-13

12.0 g (37.6 mmol) of Intermediate I-12 was completely dissolved in 100 mL of $CH_2Cl_2$, and 3.63 g (14.3 mmol) of $I_2$ and 2.41 g (11.28 mmol) of $KIO_3$ were added thereto in divided amounts of ⅕. The reaction mixture was stirred over 6 hours and washed with methanol to produce 9.21 g of Intermediate I-13 (yield: 55%). The produced compound was identified using (utilizing) LC-MS. $C_{24}H_{16}IN$: $M^+$ 445.0.

3) Synthesis of Intermediate I-14

8.25 g of Intermediate I-14 was produced with a yield of 90% in the same manner as in the synthesis of Intermediate I-5, except that Intermediate I-13 was used (utilized) instead of Intermediate I-4 in the synthesis of Intermediate I-5. The produced compound was identified using (utilizing) LC-MS. $C_{24}H_{14}IN$: $M^+$ 443.0.

4) Synthesis of Intermediate I-15

5.22 g of Intermediate I-15 was produced with a yield of 82% in the same manner as in the synthesis of Intermediate I-8, except that Intermediate I-14 was used (utilized) instead of Intermediate I-7 in the synthesis of Intermediate I-8. The produced compound was identified using (utilizing) LC-MS. $C_{25}H_{14}N_2$: $M^+$ 342.1.

5) Synthesis of Intermediate I-16

5.46 g of Intermediate I-16 was produced with a yield of 85% in the same manner as in the synthesis of Intermediate I-9, except that Intermediate I-15 was used (utilized) instead of Intermediate I-8 in the synthesis of Intermediate I-9. The produced compound was identified using (utilizing) LC-MS. $C_{25}H_{13}BrN_2$: $M^+$ 420.0.

6) Synthesis of Compound 45

5.18 g of Compound 45 was produced with a yield of 62% in the same manner as in the synthesis of Compound 1, except that Intermediate I-16 was used (utilized) instead of Intermediate I-9 in the synthesis of Compound 1. The produced compound was identified using (utilizing) MS/FAB and $^1$H NMR. $C_{49}H_{28}N_2$ cal. 644.23, found 644.25.

Synthesis of Compound 55

4.79 g of Compound 55 was produced with a yield of 67% in the same manner as in the synthesis of Compound 45, except that 3-bromopyridine was used (utilized) instead of bromonaphthalene in the synthesis of Intermediate I-12. The produced compound was identified using (utilizing) MS/FAB and $^1$H NMR. $C_{44}H_{25}N_3$ cal. 595.20, found 595.21.

Synthesis of Compound 62

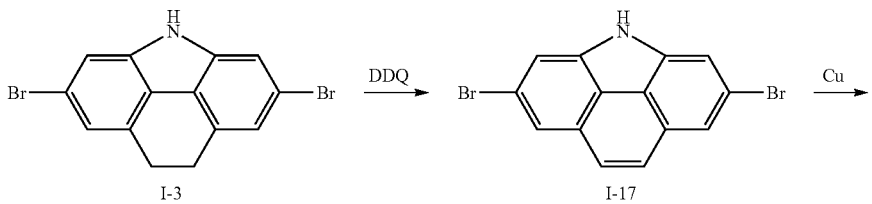

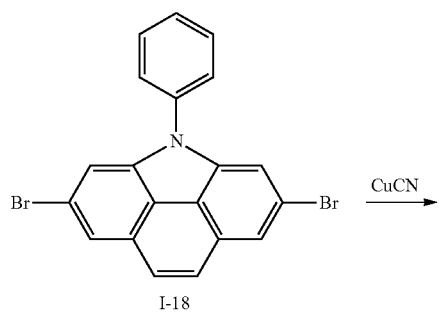

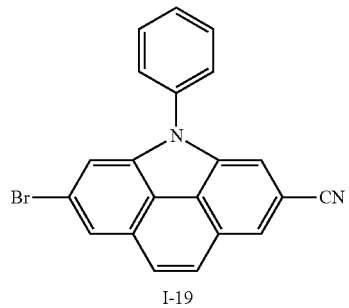

I-19

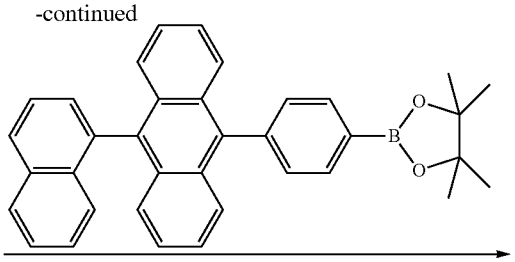

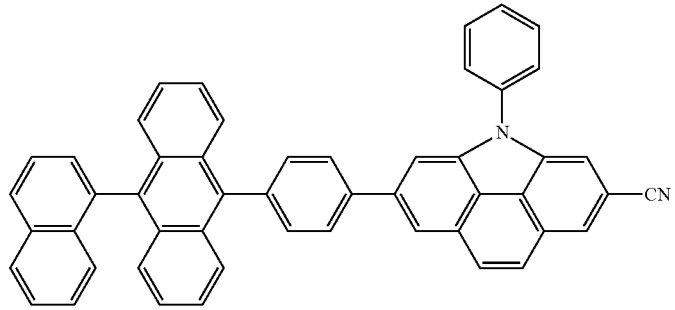

62

1) Synthesis of Intermediate I-17

12.1 g of Intermediate I-17 was produced with a yield of 87% in the same manner as in the synthesis of Intermediate I-5, except that Intermediate I-3 was used (utilized) instead of Intermediate I-4 in the synthesis of Intermediate I-5. The produced compound was identified using (utilizing) LC-MS. $C_{14}H_7Br_2N$: $M^+$ 346.9.

2) Synthesis of Intermediate I-18

10.0 g of Intermediate I-18 was produced with a yield of 68% in the same manner as in the synthesis of Intermediate I-6, except that Intermediate I-17 was used (utilized) instead of Intermediate I-5 in the synthesis of Intermediate I-6. The produced compound was identified using (utilizing) LC-MS. $C_{20}H_{11}Br_2N$: $M^+$ 422.9.

3) Synthesis of Intermediate I-19

10.0 9 (23.7 mmol) of Intermediate I-18 and 2.12 g (23.7 mmol) of CuCN were dissolved in 70 mL of DMF, and the reaction mixture was stirred at 150° C. over 24 hours. The reaction mixture was cooled to room temperature, 60 mL of ammonia water and 60 mL of water were added thereto, and the reaction mixture was subjected to extraction three times with 50 mL of $CH_2Cl_2$. An organic layer was collected and dried using (utilizing) magnesium sulfate to evaporate the solvent. The remainder was purified using (utilizing) silica gel column chromatography to obtain 2.82 g of Intermediate I-19 (Yield: 32%). The produced compound was identified using (utilizing) LC-MS. $C_{21}H_{11}BrN_2$: $M^+$ 370.0.

4) Synthesis of Compound 62

3.86 g of Compound 62 was produced with a yield of 76% in the same manner as in the synthesis of Compound 1, except that Intermediate I-19 was used (utilized) instead of Intermediate I-9, and 4,4,5,5-tetramethyl-2-[4-(10-naphthalene-1-yl-anthracene-9-yl)-phenyl]-[1,3,2]-dioxyborolane was used (utilized) instead of 4,4,5,5-tetramethyl-2-(10-naphthalene-1-yl-anthracene-9-yl)-[1,3,2]dioxaborolane in the synthesis of Compound 1. The produced compound was identified using (utilizing) MS/FAB and $^1H$ NMR. $C_{51}H_{30}N_2$ cal. 670.24, found 670.25.

Synthesis of Compound 65

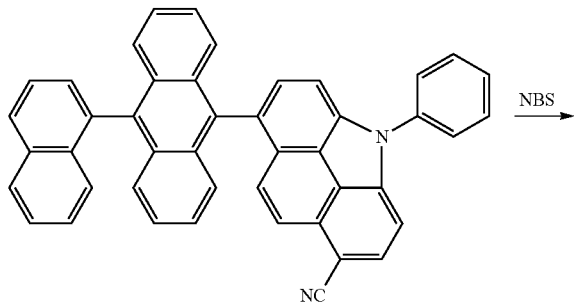

1

-continued

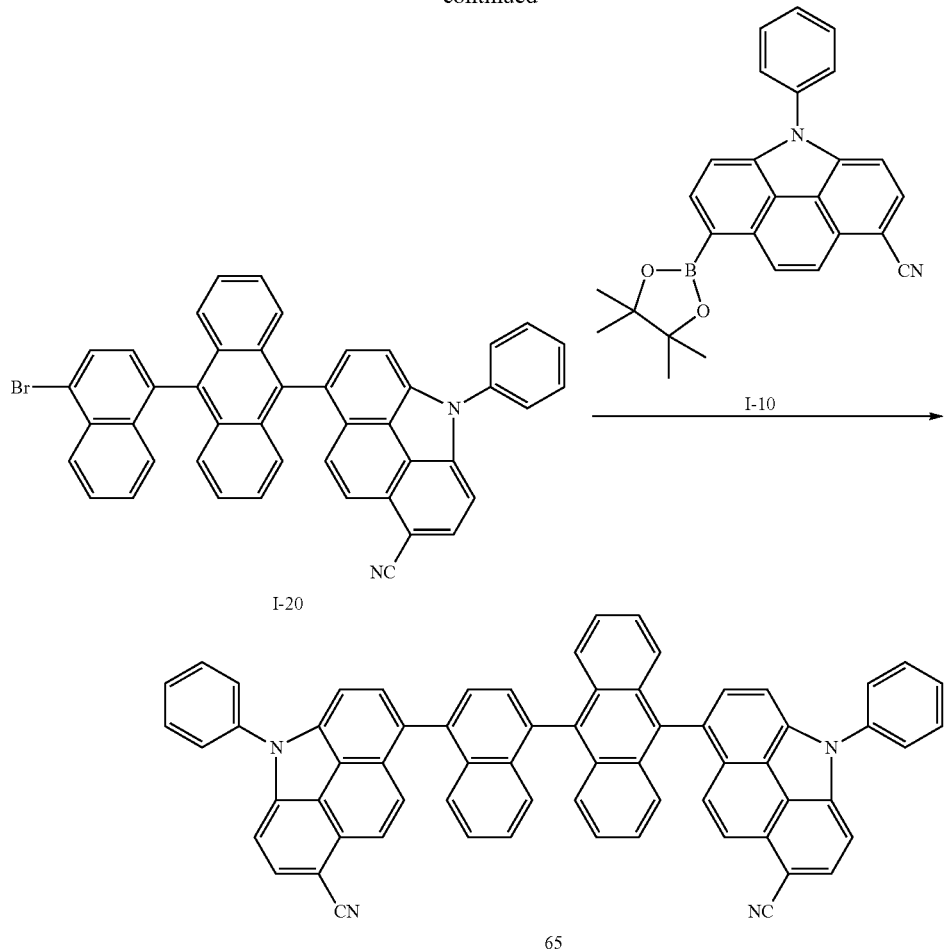

1) Synthesis of Intermediate I-20

5.95 g (10.0 mmol) of Compound 1 was completely dissolved in 80 mL of $CH_2Cl_2$, and 4.15 g (10.0 mmol) of N-bromosuccinimide was added thereto. Then, the reaction mixture was stirred at room temperature over 12 hours. 60 mL of water was added to the reaction mixture, and the reaction mixture was subjected to extraction three times with 50 mL of $CH_2Cl_2$. An organic layer was collected and dried using (utilizing) magnesium sulfate to evaporate the solvent. The remainder was recrystallized with methanol to produce 5.52 g of Intermediate I-20 (Yield: 82%). The produced compound was identified using (utilizing) LC-MS. $C_{45}H_{25}BrIN_2$: $M^+$ 672.1.

2) Synthesis of Compound 65

5.59 g of Compound 65 was produced with a yield of 77% in the same manner as in the synthesis of Compound 1, except that Intermediate I-20 was used (utilized) instead of Intermediate I-9, and Intermediate I-10 was used (utilized) instead of 4,4,5,5-tetramethyl-2-(10-naphthalene-1-yl-anthracene-9-yl)-[1,3,2]dioxaborolane in the synthesis of Compound 1. The produced compound was identified using (utilizing) MS/FAB and $^1$H NMR. $C_{66}H_{36}N_4$ cal. 884.29, found 884.30.

Synthesis of Compound 75

3.99 g of Compound 75 was produced with a yield of 62% in the same manner as in the synthesis of Compound 1, except that 9-bromophenanthrene was used (utilized) instead of bromophenyl in the synthesis of Intermediate I-6, and 2-[1,1']binaphthalenyl-4-yl-4,4,5,5-tetramethyl-[1,3,2]dioxyborolane was used (utilized) instead of 4,4,5,5-tetramethyl-2-(2-naphthalene-1-yl-anthracene-9-yl)-[1,3,2]diooxaborolane in the synthesis of Compound 1. The produced compound was identified using (utilizing) MS/FAB and $^1$H NMR. $C_{49}H_{28}N_2$ cal. 644.23, found 644.25.

Synthesis of Compound 91

3.66 g of Compound 91 was produced with a yield of 67% in the same manner as in the synthesis of Compound 62, except that 3-bromopyridine was used (utilized) instead of bromophenyl in the synthesis of Intermediate I-18, and 2-[1,1']binaphthalenyl-4-yl-4,4,5,5-tetramethyl-[1,3,2]dioxyborolane was used (utilized) instead of 4,4,5,5-tetramethyl-2-(2-naphthalene-1-yl-anthracene-9-yl)-[1,3,2]diooxaborolane in the synthesis of Compound 62. The produced compound was identified using (utilizing) MS/FAB and $^1$H NMR. $C_{40}H_{23}N_3$ cal. 545.19, found 545.20.

Compounds were further synthesized in the same manner as the aforementioned synthesis methods using (utilizing) appropriate intermediate materials, and $^1$H NMR and MS/FAB results of the synthesized compounds are shown in Table 1 below.

Compounds other than those listed in Table 1 may also be easily synthesized by one of ordinary skill in the art with reference to the synthesis methods and the raw materials as described above.

TABLE 1

| Compound | $^1$H NMR (CDCl$_3$, 400 MHz) | MS/FAB found | MS/FAB calc. |
|---|---|---|---|
| 1 | δ = 8.07 (d, 1H), 7.99 (d, 1H), 7.95 (d, 1H), 7.84-7.79 (m, 5H), 7.72-7.69 (m, 2H), 7.56-7.49 (m, 5H), 7.46-7.43 (m, 2H), 7.40-7.35 (m, 3H), 7.34 (s, 2H), 7.31-7.29 (m, 3H), 7.16-7.12 (m, 1H) | 594.20 | 594.21 |
| 5 | δ = 8.63 (dd, 1H), 8.50 (dd, 1H), 8.22 (d, 1H), 8.00 (d, 1H), 7.98 (d, 1H), 7.85-7.79 (m, 6H), 7.72-.7.68 (m, 2H), 7.62 (d, 1H), 7.54-7.45 (m, 3H), 7.41-7.38 (m, 1H), 7.35-7.29 (m, 6H), 7.18-7.14 (m, 1H) | 595.21 | 595.20 |
| 15 | δ = 8.78-8.75 (m, 4H), 8.53 (d, 1H), 8.39 (d, 1H), 8.09 (dd, 2H), 7.87-7.80 (m, 6H), 7.73-7.64 (m, 6H), 7.54-7.51 (m, 2H), 7.45-7.38 (m, 3H), 7.35-7.29 (m, 5H), 7.15-7.12 (m, 1H) | 749.27 | 749.26 |
| 21 | δ = 9.25 (d, 1H), 8.23 (dd, 2H), 8.09 (t, 2H), 7.94-7.82 (m, 7H), 7.72-7.69 (m, 2H), 7.55-7.50 (m, 6H), 7.43-7.28 (m, 8H), 7.16-7.12 (m, 1H) | 671.22 | 671.24 |
| 26 | δ = 8.08 (d, 1H), 8.04-8.02 (m, 2H), 7.99 (d, 1H), 7.95 (d, 1H), 7.92 (d, 1H), 7.84-7.79 (m, 5H), 7.71-7.67 (m, 3H), 7.58-7.43 (m, 7H), 7.40-7.29 (m, 8H), 7.18-7.13 (m, 1H) | 670.25 | 670.24 |
| 28 | δ = 8.11 (d, 1H), 8.06 (d, 1H), 8.04-7.99 (m, 3H), 7.93 (d, 1H), 7.91 (d, 1H), 7.86-7.77 (m, 5H), 7.73 (d, 1H), 7.71-7.65 (m, 5H), 7.59-7.53 (m, 2H), 7.50-7.44 (m, 3H), 7.41-7.31 (m, 7H), 7.12-7.08 (m, 2H) | 720.27 | 720.26 |
| 31 | δ = 8.60 (dd, 1H), 8.06 (d, 1H), 8.04-8.02 (m, 2H), 7.98 (d, 1H), 7.96-7.85 (m, 4H), 7.83-7.77 (m, 5H), 7.72-7.68 (m, 3H), 7.54 (d, 1H), 7.49-7.45 (m, 4H), 7.41-7.29 (m, 7H), 7.16-7.12 (m, 2H) | 721.23 | 721.25 |
| 36 | δ = 8.96 (d, 1H), 8.60 (dd, 2H), 8.07 (d, 1H), 8.00 (d, 1H), 7.95 (d, 1H), 7.84-7.70 (m, 7H), 7.55-7.48 (m, 5H), 7.43-7.27 (m, 9H), 7.20-7.17 (m, 1H), 7.13-7.10 (m, 1H) | 671.25 | 671.24 |
| 43 | δ = 8.93 (dd, 1H), 8.83-8.81 (m, 4H), 8.57 (d, 1H), 8.07 (d, 1H), 8.00-7.94 (m, 3H), 7.83-7.76 (m, 4H), 7.70-7.67 (m, 1H), 7.63-7.48 (m, 10H), 7.45-7.31 (m, 9H), 7.19-7.16 (m, 1H) | 825.30 | 825.29 |
| 45 | δ = 8.07 (dd, 1H), 8.01-7.98 (m, 2H), 7.93 (d, 1H), 7.86-7.80 (m, 7H), 7.74-7.65 (m, 4H), 7.60-7.45 (m, 6H), 7.37-7.30 (m, 6H), 7.15-7.10 (m, 1H) | 644.25 | 644.23 |
| 55 | δ = 8.62 (dd, 1H), 8.49 (dd, 1H), 8.29 (d, 1H), 8.22 (d, 1H), 8.00-7.97 (m, 3H), 7.87 (dd, 1H), 7.83-7.78 (m, 4H), 7.72-7.69 (m, 2H), 7.58-7.28 (m, 10H), 7.16-7.12 (m, 1H) | 595.21 | 595.20 |
| 62 | δ = 8.07 (d, 1H), 8.03-8.01 (m, 2H), 7.97 (d, 1H), 7.93 (d, 1H), 7.91 (d, 1H), 7.83-7.77 (m, 5H), 7.70-7.65 (m, 3H), 7.58-7.44 (m, 7H), 7.39-7.31 (m, 8H), 7.17-7.13 (m, 1H) | 670.25 | 670.24 |
| 65 | δ = 8.07 (d, 2H), 8.00-7.91 (m, 6H), 7.84-7.79 (m, 4H), 7.70-7.66 (m, 2H), 7.56-7.48 (m, 10H), 7.43-7.31 (m, 10H), 7.15-7.12 (m, 1H), 7.09-7.06 (m, 1H) | 884.30 | 884.29 |
| 75 | δ = 8.66-8.63 (m, 1H), 8.27-8.25 (m, 1H), 8.18-8.14 (m, 2H), 8.03 (d, 1H), 7.98 (d, 1H), 7.82-7.76 (m, 2H), 7.70-7.53 (m, 11H), 7.50-7.43 (m, 3H), 7.36 (d, 1H), 7.29-7.20 (m, 2H), 7.15-7.10 (m, 3H) | 644.25 | 644.23 |
| 85 | δ = 8.08-8.06 (m, 1H), 8.01 (dd, 1H), 7.98 (d, 1H), 7.95 (d, 1H), 7.85-7.76 (m, 3H), 7.73-7.40 (m, 14H), 7.29-7.20 (m, 2H), 7.17-7.13 (m, 3H) | 594.20 | 594.21 |
| 91 | δ = 8.73 (d, 1H), 8.49 (dd, 1H), 8.30-8.25 (m, 1H), 8.17 (d, 1H), 8.08 (d, 1H), 8.01 (d, 1H), 7.98-7.94 (m, 2H), 7.81 (d, 1H), 7.76 (d, 1H), 7.63-7.58 (m, 4H), 7.53-7.50 (m, 1H), 7.45-7.40 (m, 4H), 7.29-7.25 (m, 1H), 7.12-7.05 (m, 3H) | 545.20 | 545.19 |

Example 1

A Corning 15 Ω/cm² (1200 Å) ITO glass substrate was cut to a size of 50 mm×50 mm×0.7 mm, sonicated using (utilizing) isopropyl alcohol and pure water for five minutes each, and then cleaned by irradiation of UV rays for 30 minutes and exposure to ozone. Then, the resulting glass substrate, as an anode, was disposed in a vacuum deposition apparatus.

Then, 2-TNATA, which is a suitable hole injecting material, was vacuum deposited on the glass substrate to form an HIL having a thickness of 600 Å, and then 4,4'-bis[N-(1-naphthyl)-N-phenylamino]biphenyl (NPB), as a hole transporting compound, was vacuum deposited on the HIL to form an HTL having a thickness of 300 Å.

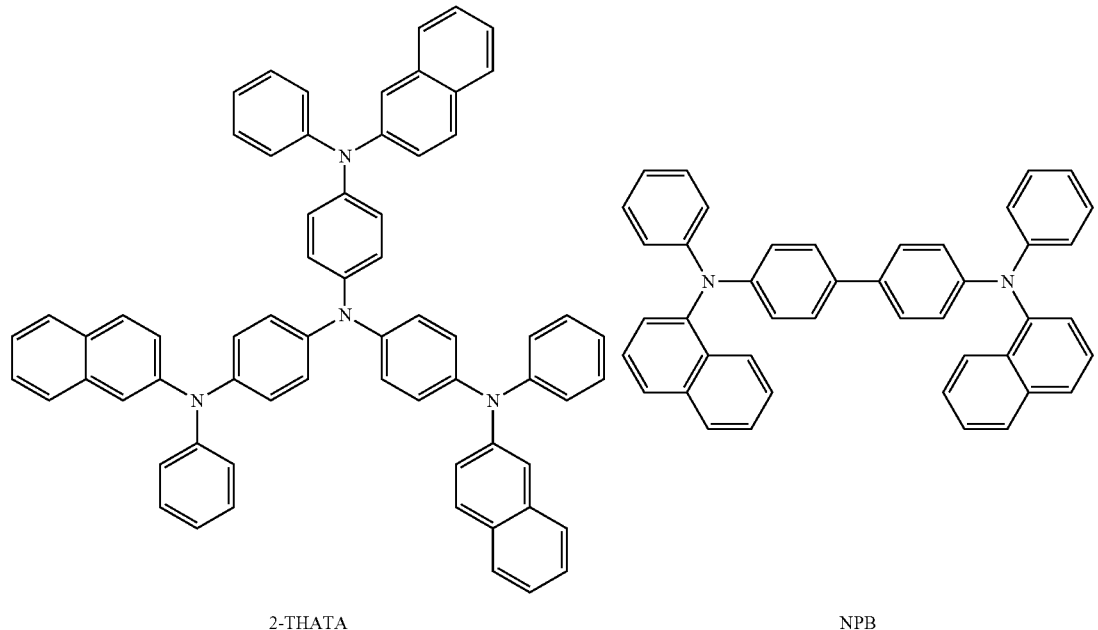

2-THATA                                                    NPB

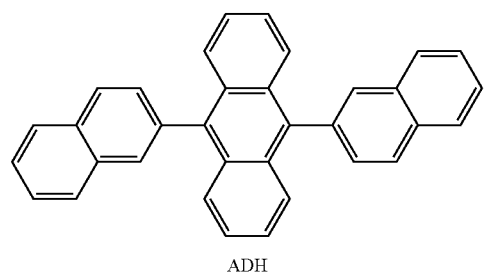

ADH

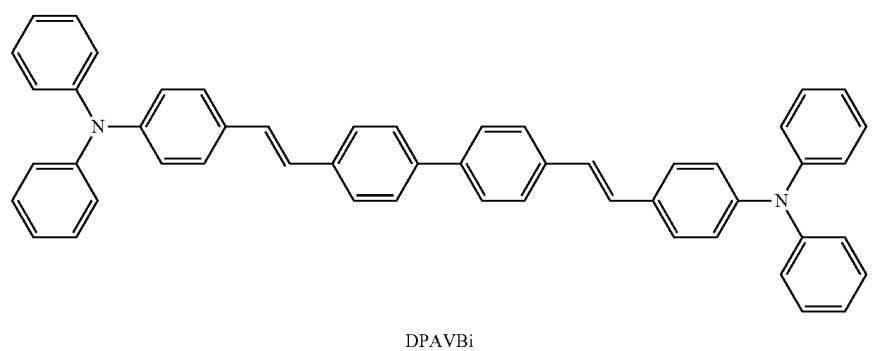

DPAVBi 9,10-di-naphthalene-2-yl-anthracene (ADN), as a suitable blue fluorescent host, and 4,4'-bis[2-(4-(N,N-diphenylamino)phenyl)vinyl]biphenyl (DPAVBi), as a suitable blue fluorescent dopant, were co-deposited at a weight ratio of 98:2 on the HTL to form an EML having a thickness of 300 Å.

Then, Compound 1 according to an embodiment of the present invention was deposited on the EML to form an ETL having a thickness of 300 Å, and LiF, which is halogenated alkali metal, was deposited on the ETL to form an EIL having a thickness of 10 Å. Then, Al was deposited on the EIL to a thickness of 3000 Å (cathode), thereby forming a LiF/Al electrode. As a result, the manufacture of an organic light-emitting device was completed.

Example 2

An organic light-emitting device was manufactured in the same manner as in Example 1, except that Compound 5 was used (utilized) instead of Compound 1 to form the ETL.

Example 3

An organic light-emitting device was manufactured in the same manner as in Example 1, except that Compound 15 was used (utilized) instead of Compound 1 to form the ETL.

Example 4

An organic light-emitting device was manufactured in the same manner as in Example 1, except that Compound 21 was used (utilized) instead of Compound 1 to form the ETL.

Example 5

An organic light-emitting device was manufactured in the same manner as in Example 1, except that Compound 26 was used (utilized) instead of Compound 1 to form the ETL.

Example 6

An organic light-emitting device was manufactured in the same manner as in Example 1, except that Compound 43 was used (utilized) instead of Compound 1 to form the ETL.

Example 7

An organic light-emitting device was manufactured in the same manner as in Example 1, except that Compound 45 was used (utilized) instead of Compound 1 to form the ETL.

Example 8

An organic light-emitting device was manufactured in the same manner as in Example 1, except that Compound 55 was used (utilized) instead of Compound 1 to form the ETL.

Example 9

An organic light-emitting device was manufactured in the same manner as in Example 1, except that Compound 62 was used (utilized) instead of Compound 1 to form the ETL.

Example 10

An organic light-emitting device was manufactured in the same manner as in Example 1, except that Compound 65 was used (utilized) instead of Compound 1 to form the ETL.

Example 11

An organic light-emitting device was manufactured in the same manner as in Example 1, except that Compound 75 was used (utilized) instead of Compound 1 to form the ETL.

Example 12

An organic light-emitting device was manufactured in the same manner as in Example 1, except that Compound 91 was used (utilized) instead of Compound 1 to form the ETL.

Comparative Example 1

An organic light-emitting device was manufactured in the same manner as in Example 1, except that Compound 200, as a suitable electron transporting material, was used (utilized) instead of Compound 1 to form the ETL.

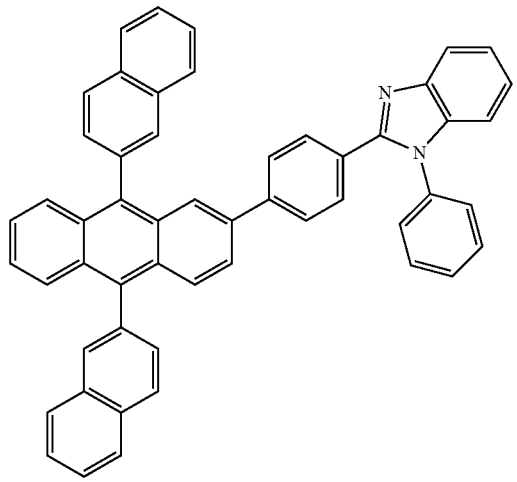

Comparative Example 2

An organic light-emitting device was manufactured in the same manner as in Example 1, except that Compound 201, as a suitable electron transporting material, was used (utilized) instead of Compound 1 to form the ETL.

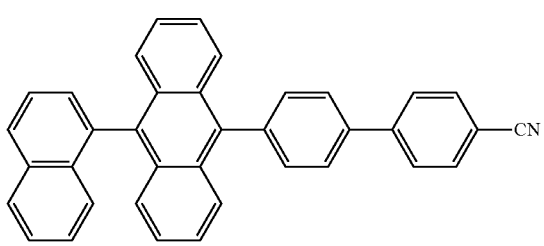

Comparative Example 3

An organic light-emitting device was manufactured in the same manner as in Example 1, except that Compound 202, as a suitable electron transporting material, was used (utilized) instead of Compound 1 to form the ETL.

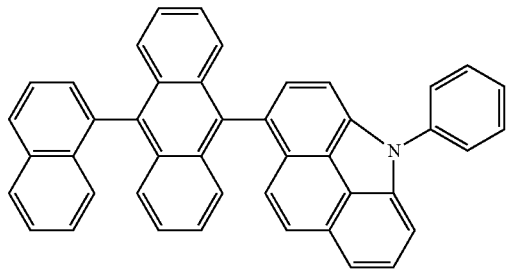

Characteristics of the organic light-emitting devices according to the examples and comparative examples are shown in Table 2 below.

TABLE 2

| | Electron transporting material | Driving voltage (V) | Current density (mA/cm$^2$) | Brightness (Cd/A) | Efficiency (Cd/A) | Color | Half-lifespan (hr @100 mA/cm$^2$) |
|---|---|---|---|---|---|---|---|
| Example 1 | Compound 1 | 4.60 | 50 | 3,980 | 8.12 | blue | 670 hr |
| Example 2 | Compound 5 | 4.82 | 50 | 3,650 | 7.85 | blue | 603 hr |
| Example 3 | Compound 15 | 5.15 | 50 | 3,275 | 6.68 | blue | 537 hr |
| Example 4 | Compound 21 | 4.67 | 50 | 3,520 | 7.36 | blue | 602 hr |
| Example 5 | Compound 26 | 4.93 | 50 | 3,865 | 7.97 | blue | 639 hr |
| Example 6 | Compound 43 | 4.85 | 50 | 3,705 | 7.41 | blue | 694 hr |
| Example 7 | Compound 45 | 5.06 | 50 | 3,810 | 8.05 | blue | 582 hr |
| Example 8 | Compound 55 | 5.25 | 50 | 3,600 | 7.17 | blue | 615 hr |
| Example 9 | Compound 62 | 5.18 | 50 | 3,385 | 7.53 | blue | 627 hr |
| Example 10 | Compound 65 | 5.39 | 50 | 3,210 | 7.02 | blue | 592 hr |
| Example 11 | Compound 75 | 5.50 | 50 | 3,080 | 6.53 | blue | 576 hr |
| Example 12 | Compound 91 | 5.06 | 50 | 3,380 | 7.34 | blue | 615 hr |
| Comparative Example 1 | Compound 200 | 5.25 | 50 | 2,865 | 5.13 | blue | 337 hr |
| Comparative Example 2 | Compound 201 | 4.73 | 50 | 3,325 | 6.25 | blue | 482 hr |
| Comparative Example 3 | Compound 202 | 5.58 | 50 | 3,180 | 6.72 | blue | 318 hr |

The organic light-emitting devices according to embodiments of the present invention exhibited lower driving voltages and higher efficiency than the organic light-emitting devices according to the comparative examples.

As described above, according to the one or more of the above embodiments of the present invention, the compound represented by Formula 1 or 2 may be efficiently used (utilized) as an electron injecting material or an electron transporting material, and organic light-emitting devices including the compound of Formula 1 or 2 may have high efficiency, low driving voltage, high brightness, and long lifespan.

It should be understood that the example embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims, and equivalents thereof.

What is claimed is:

1. A compound represented by Formula 1 or 2 below:

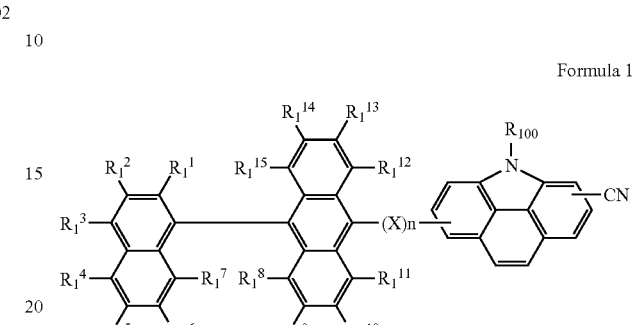

Formula 1

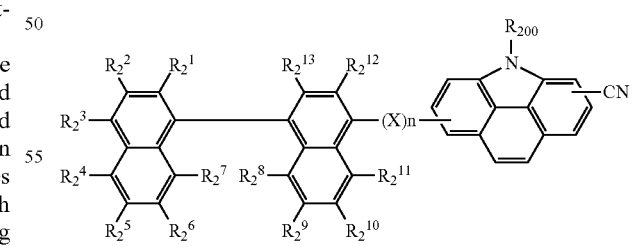

Formula 2 wherein $R_1^1$-$R_1^{15}$, $R_2^1$-$R_2^{13}$, $R_{100}$ and $R_{200}$ are each independently a hydrogen atom, a deuterium atom, a halogen atom, a nitro group, a cyano group, a substituted or unsubstituted $C_1$-$C_{60}$ alkyl group, a substituted or unsubstituted $C_1$-$C_{60}$ alkenyl group, a substituted or unsubstituted $C_3$-$C_{20}$ cycloalkyl group, a substituted or unsubstituted $C_6$-$C_{60}$ aryl group, a substituted or unsubstituted $C_2$-$C_{60}$ heteroaryl group, or a substituted or unsubstituted $C_6$-$C_{60}$ condensed polycyclic group;

X is a bivalent linking group selected from the group consisting of a substituted or unsubstituted $C_6$-$C_{40}$ arylene group, a substituted or unsubstituted $C_2$-$C_{60}$ heteroarylene group, and a substituted or unsubstituted $C_6$-$C_{60}$ condensed polycyclic group; and n is an integer from 0 to 5.

2. The compound of claim 1, wherein $R_1^1$, $R_1^2$, and $R_1^4$-$R_1^{15}$ of Formula 1 and $R_2^1$, $R_2^2$, and $R_2^4$-$R_2^{13}$ of Formula 2 are each independently a hydrogen atom or a deuterium atom.

3. The compound of claim 1, wherein $R_{100}$ of Formula 1 and $R_{200}$ of Formula 2 are each independently a substituted or unsubstituted $C_6$-$C_{60}$ aryl group or a substituted or unsubstituted $C_2$-$C_{60}$ heteroaryl group.

4. The compound of claim 1, wherein $R_{100}$ of Formula 1 and $R_{200}$ of Formula 2 are each independently represented by Formulae 2a to 2g below:

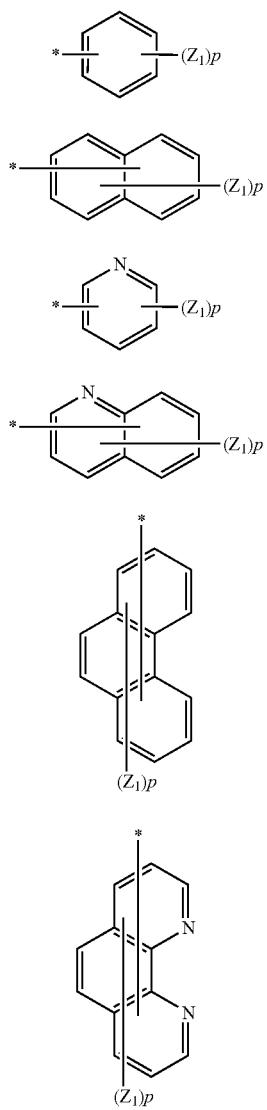

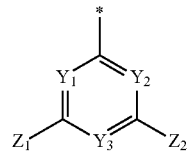

wherein $Z_1$ and $Z_2$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen atom, a cyano group, a nitro group, a hydroxyl group, or a carboxyl group, wherein when there are a plurality of $Z_1$s, they may be the same or different;

$Y_1$ to $Y_3$ are each independently CH or N;

p is an integer from 1 to 5 in Formula 2a, an integer from 1 to 7 in Formulae 2b and 2f, an integer from 1 to 4 in Formula 2c, an integer from 1 to 6 in Formula 2d, and an integer from 1 to 7 in Formula 2e; and \* is a binding site.

5. The compound of claim 1, wherein X of Formula 1 is represented by one of Formulae 3a to 3c below:

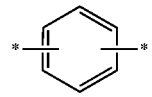

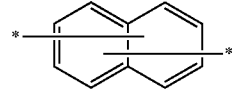

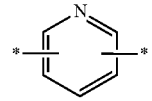

wherein \* is a binding site.

6. The compound of claim 1, wherein $R_1^3$ of Formula 1 is —CN or is represented by one of Formulae 4a to 4e:

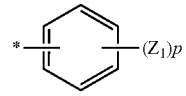

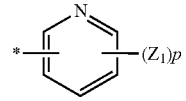

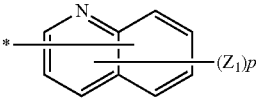

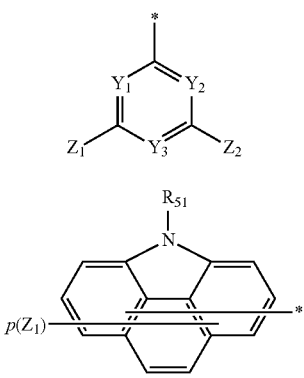

4d

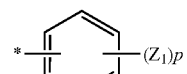

5a

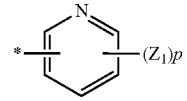

5b

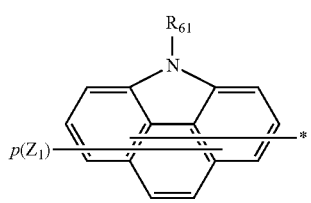

5c

4e wherein $Z_1$, $Z_2$, and $R_{51}$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen atom, a cyano group, a nitro group, a hydroxyl group, or a carboxyl group, wherein when there are a plurality of $Z_1$s, they may be the same or different;

$Y_1$ to $Y_3$ are each independently CH or N;

p is an integer from 1 to 5 in Formula 4a, an integer from 1 to 4 in Formula 4b, an integer from 1 to 6 in Formula 4c, and an integer from 1 to 7 in Formula 4e; and

* is a binding site.

7. The compound of claim 1, wherein $R_2^3$ of Formula 2 is —CN or is represented by one of Formulae 5a to 5c:

wherein $Z_1$, and $R_{61}$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen atom, a cyano group, a nitro group, a hydroxyl group, or a carboxyl group, wherein when there are a plurality of $Z_1$s, they may be the same or different;

p is an integer from 1 to 5 in Formula 5a, an integer from 1 to 4 in Formula 5b, and an integer from 1 to 7 in Formula 5c; and

* is a binding site.

8. The compound of claim 1, wherein n is an integer from 0 to 2.

9. The compound of claim 1, wherein the compound of Formula 1 is any one of the compounds below:

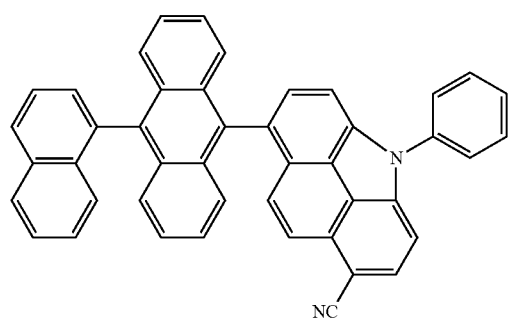

1

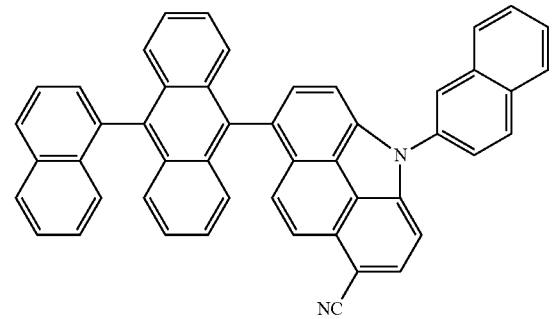

2

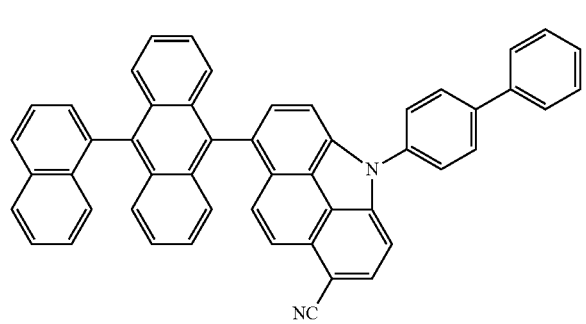

3

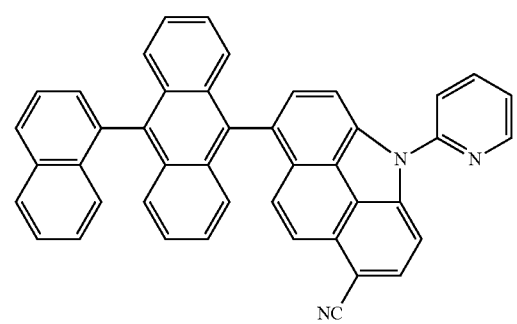

4

103
5
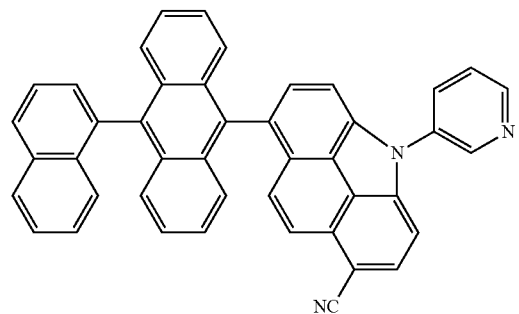
104
6
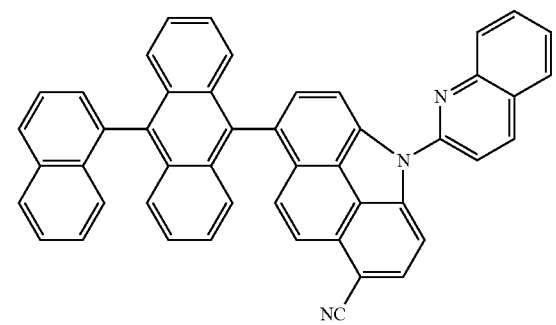
-continued
7
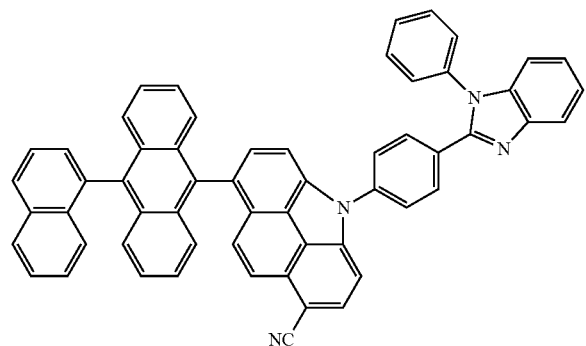
8
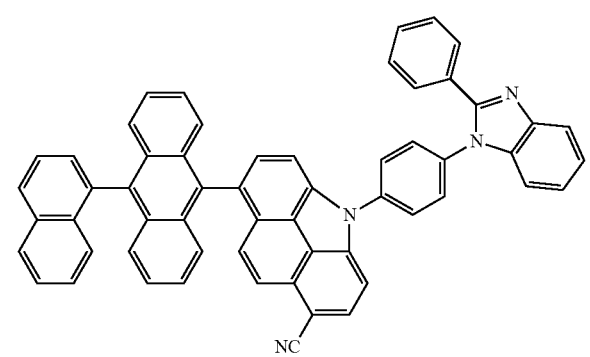
9
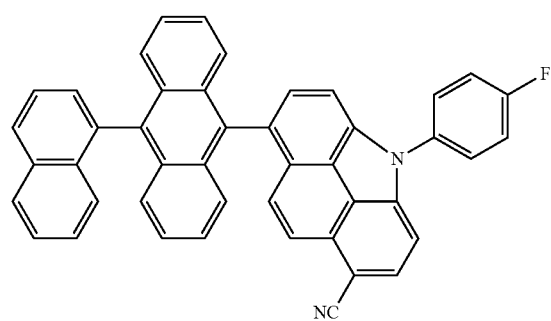
10
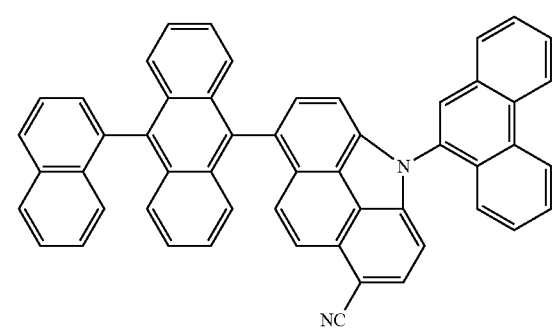
11
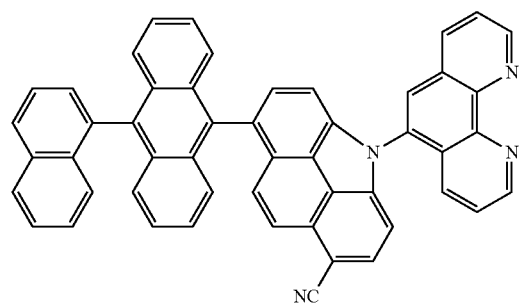
12
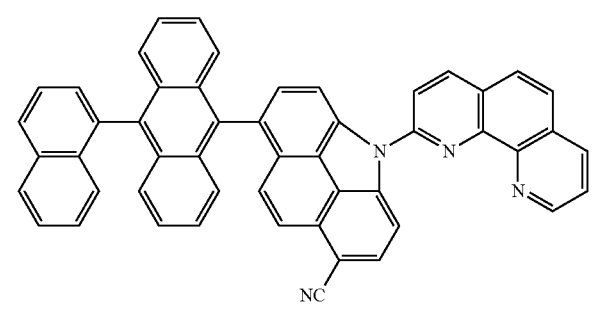

-continued
13
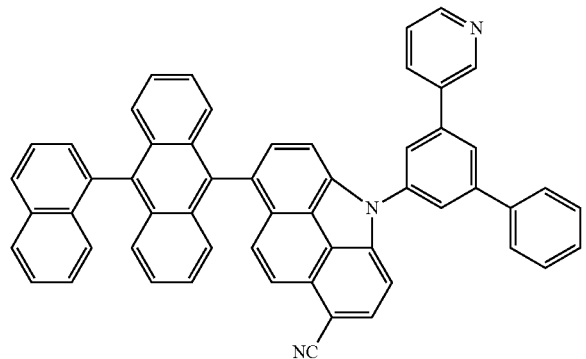
14
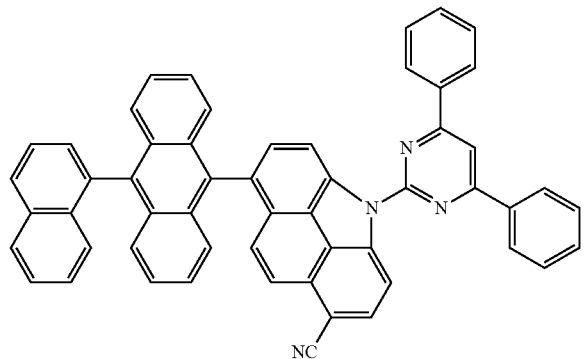
15
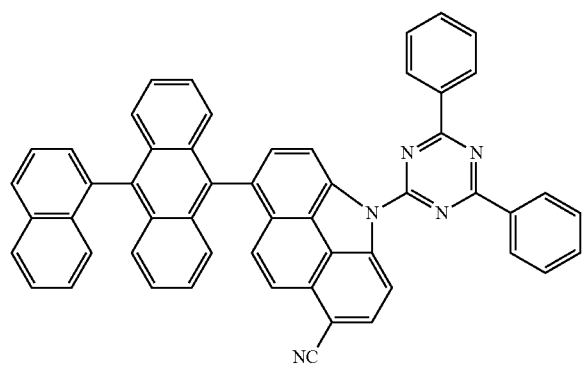
16
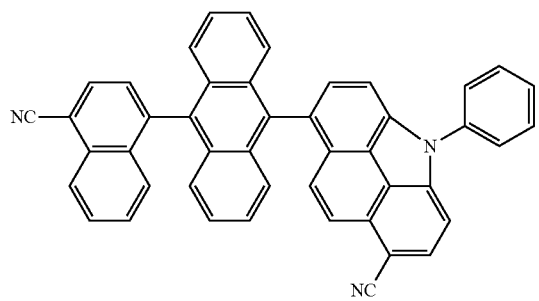
17
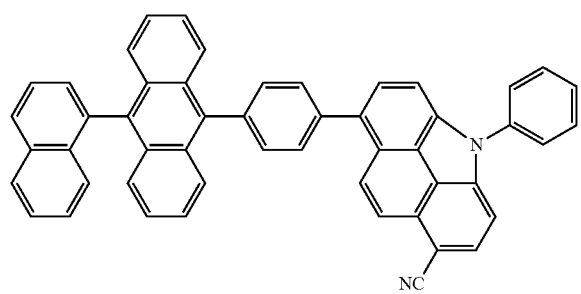
18
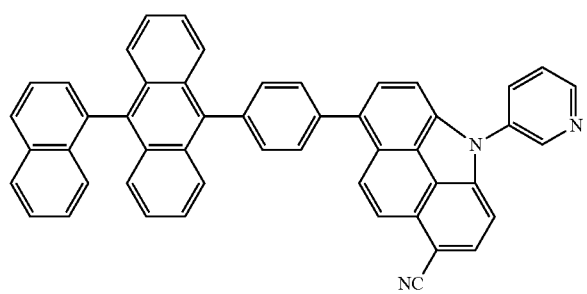
19
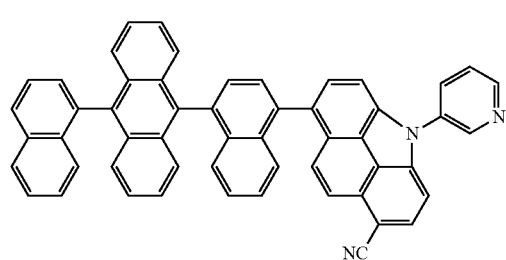
20
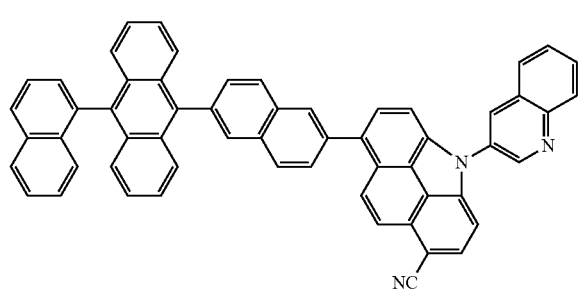
21
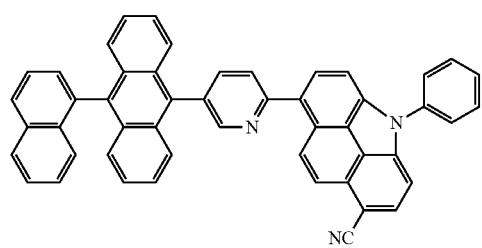
22
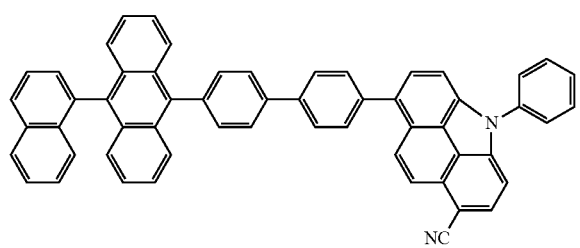

-continued
23
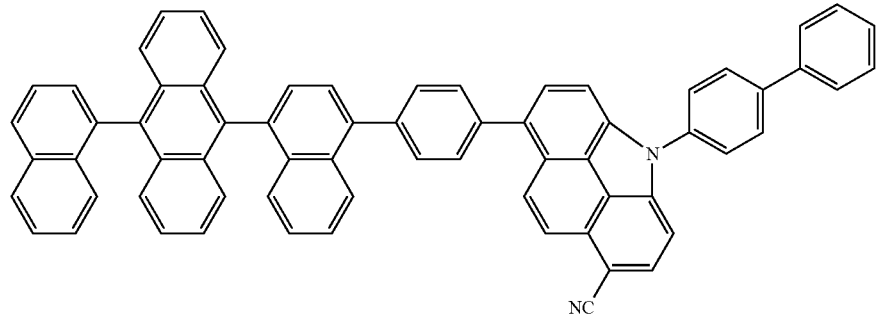
24
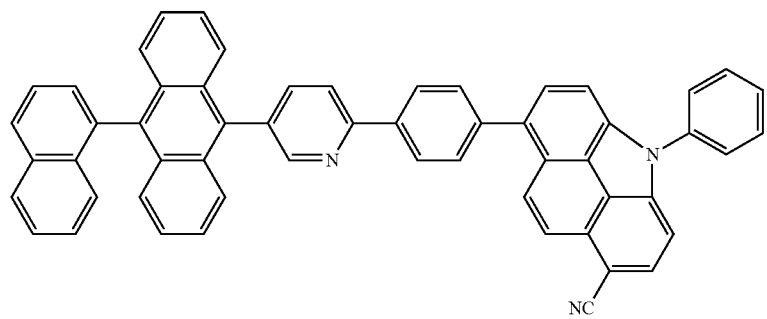
25
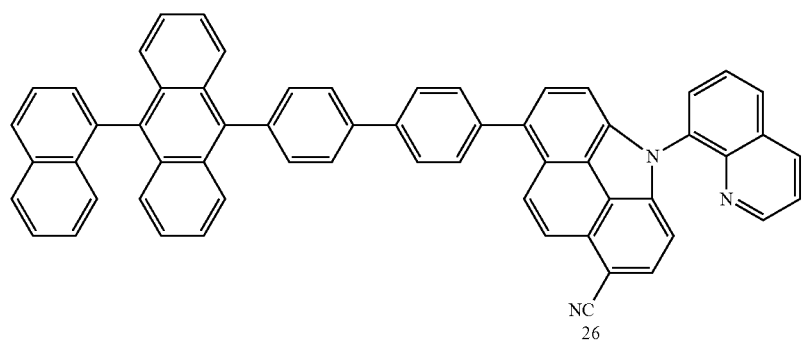
26 27
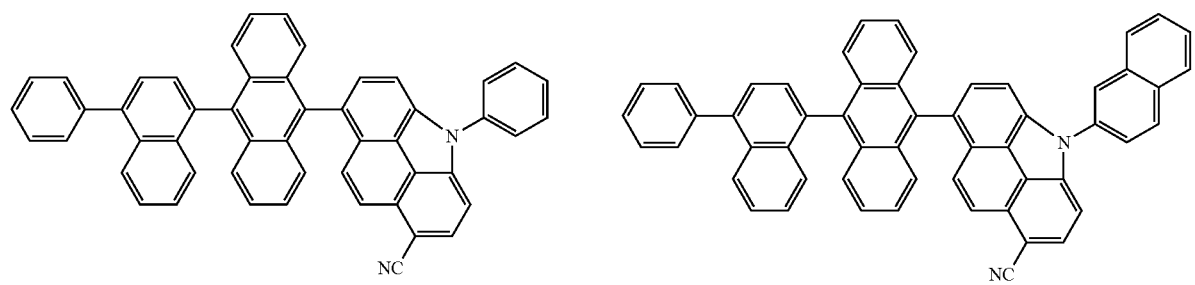
28 29
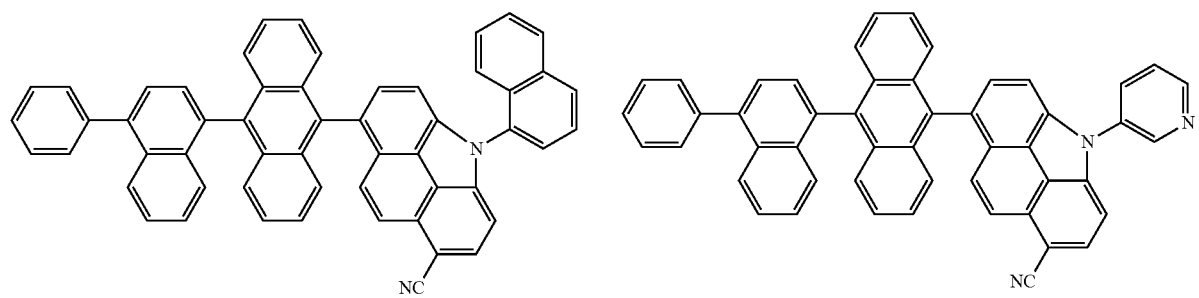

-continued
30
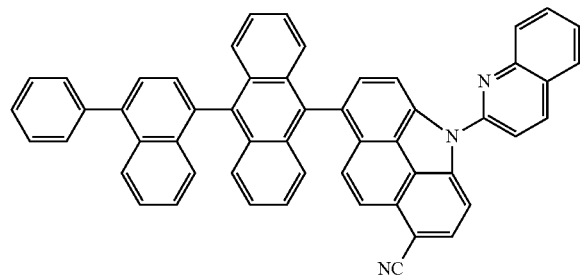
31
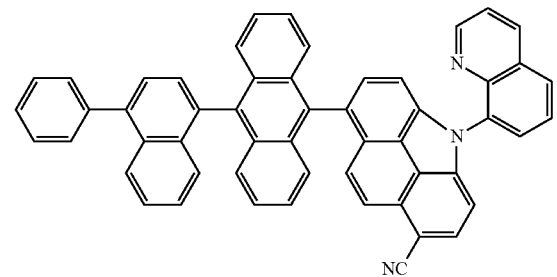
32
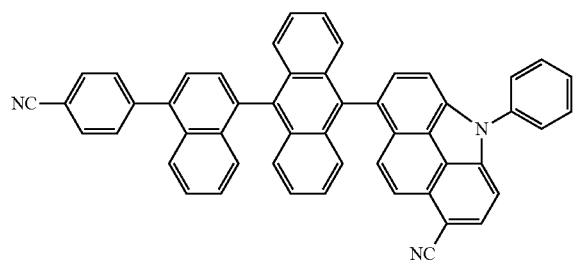
33
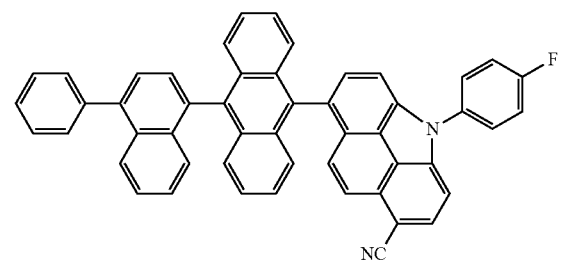
34
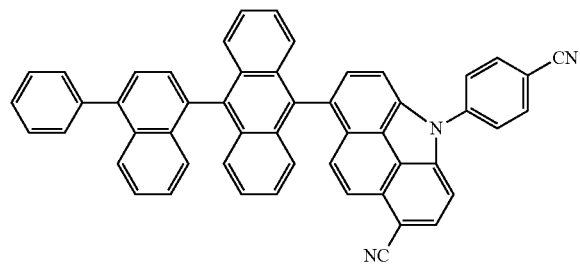
35
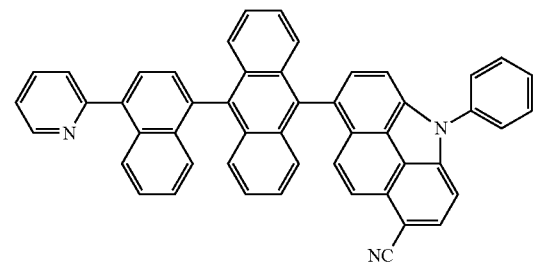
36
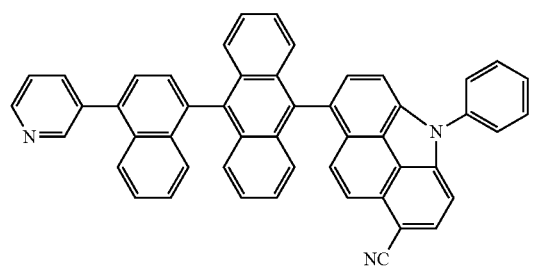
37
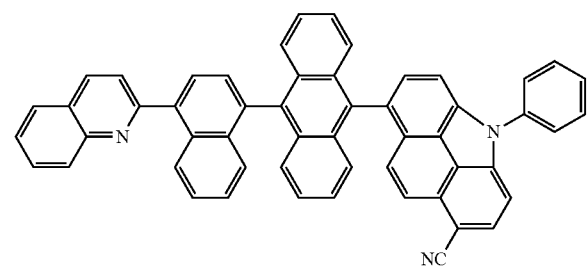
38
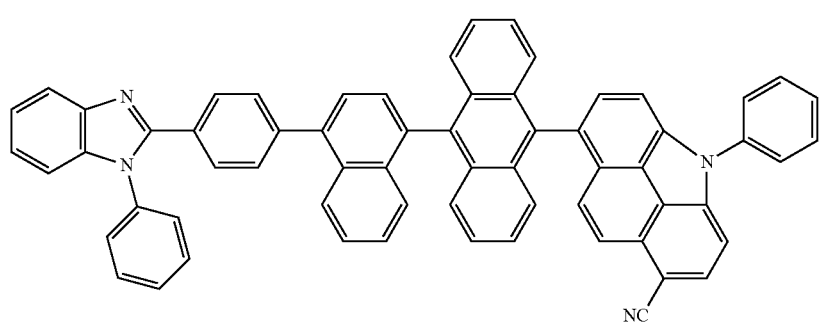

-continued
39
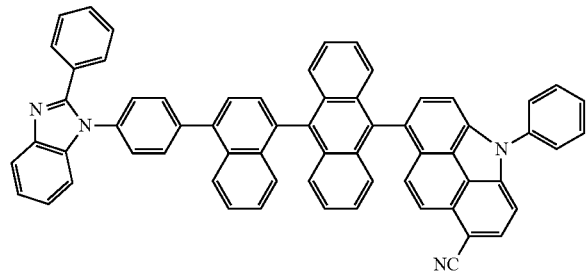
40
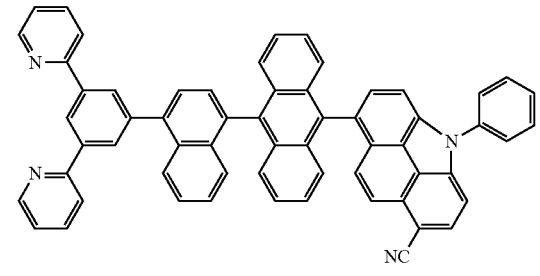
41
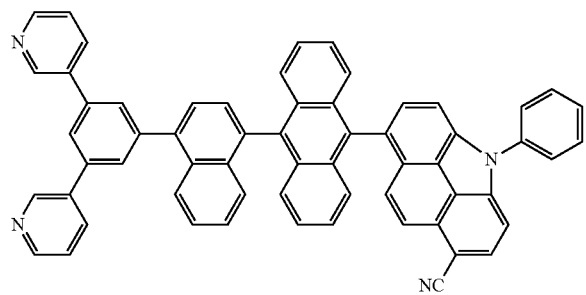
42
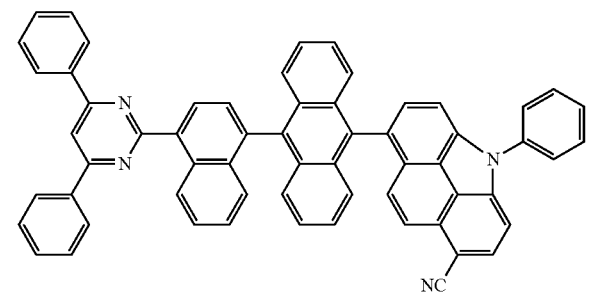
43
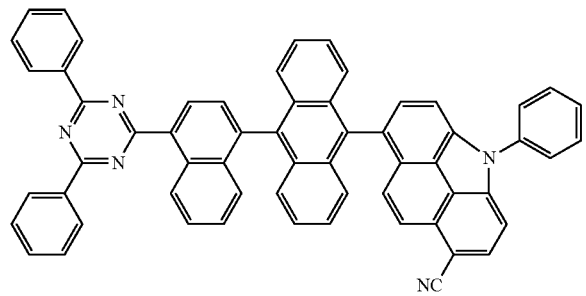
44
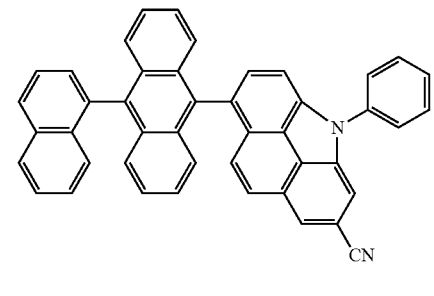
45
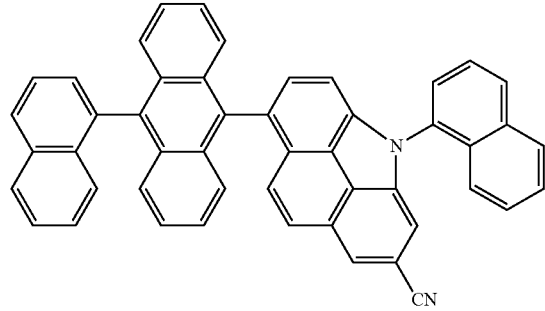
46
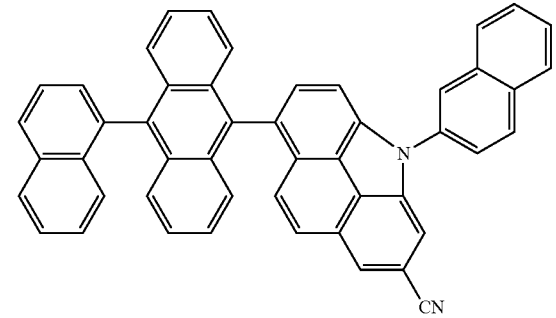
47
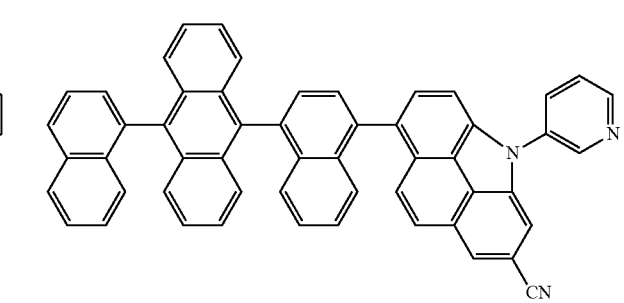
48
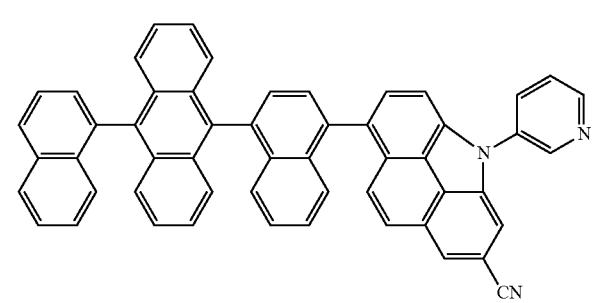

-continued
49
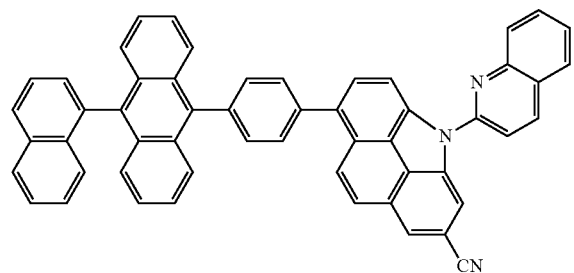
50
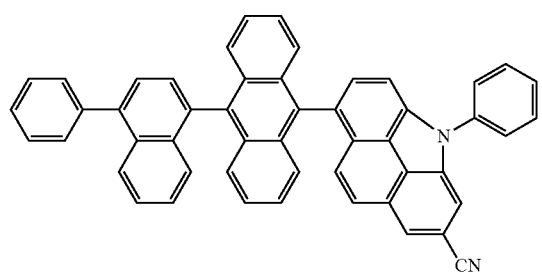
51
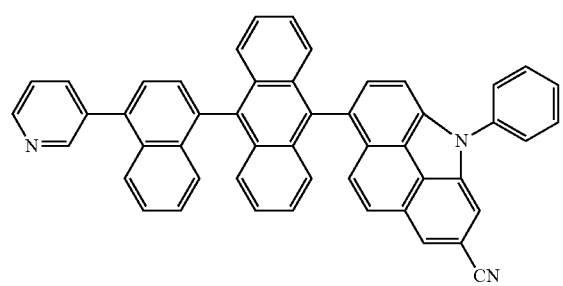
52
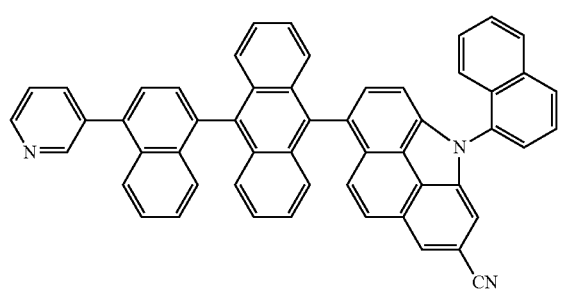
53
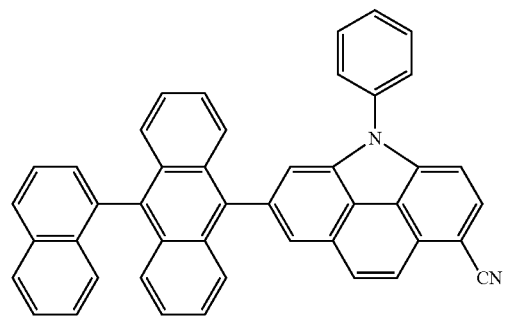
54
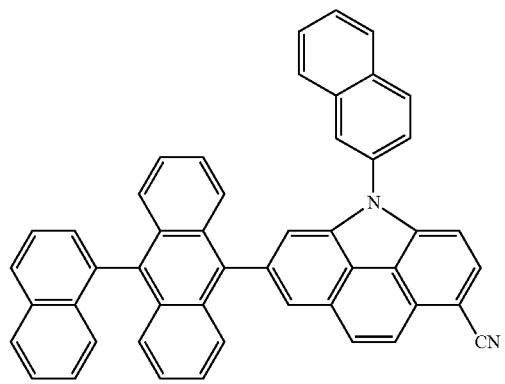
55
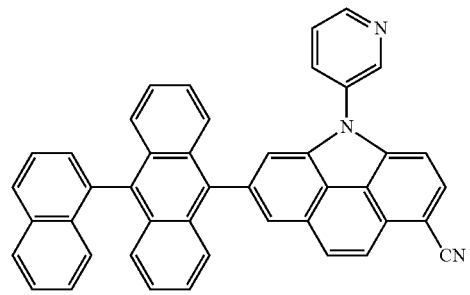
56
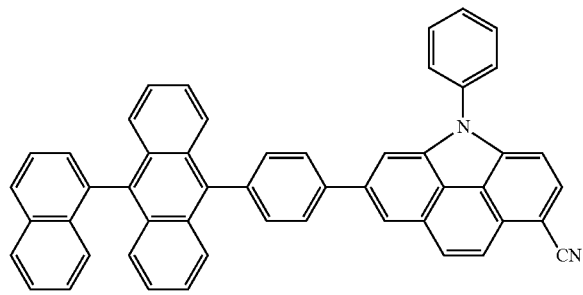
57
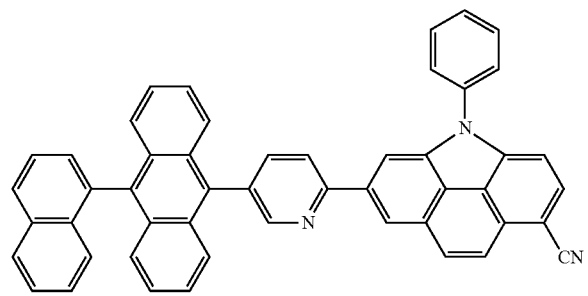
58
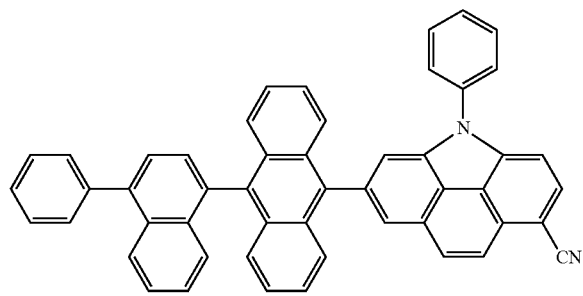

-continued
59
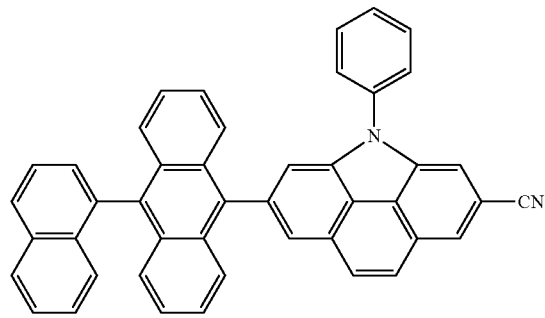
60
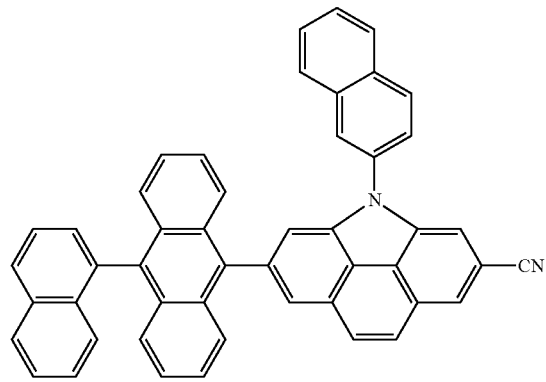
61
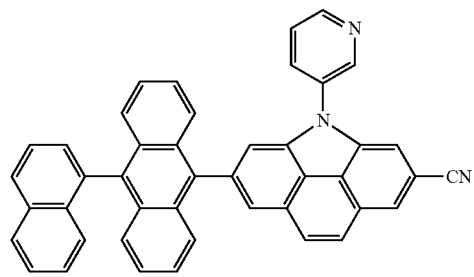
62
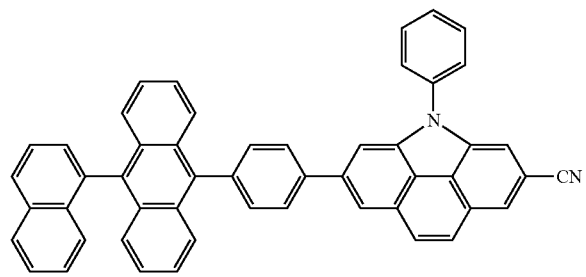
63
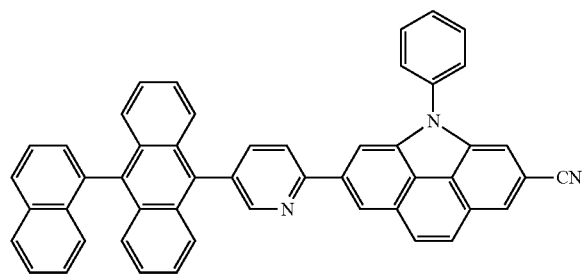
64
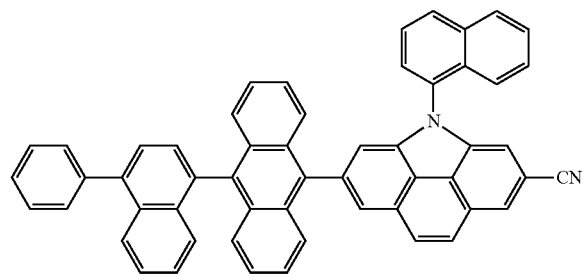
65
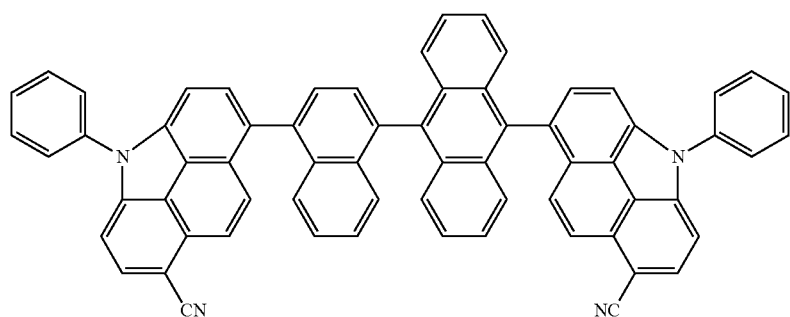
66
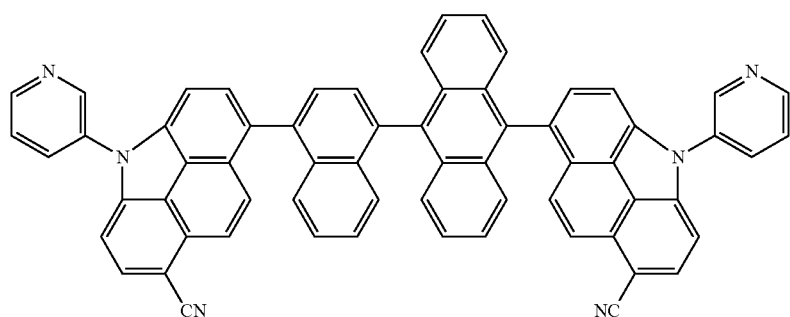

67
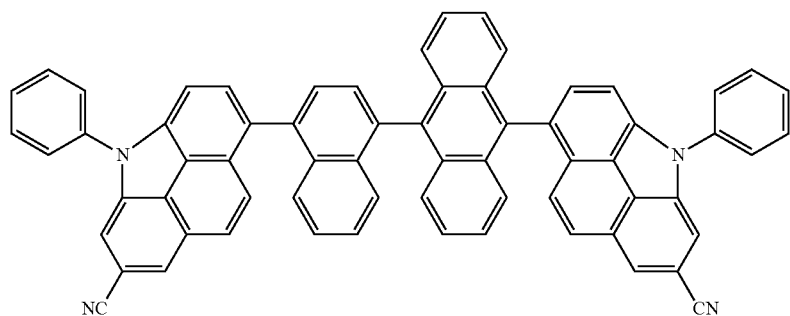
68
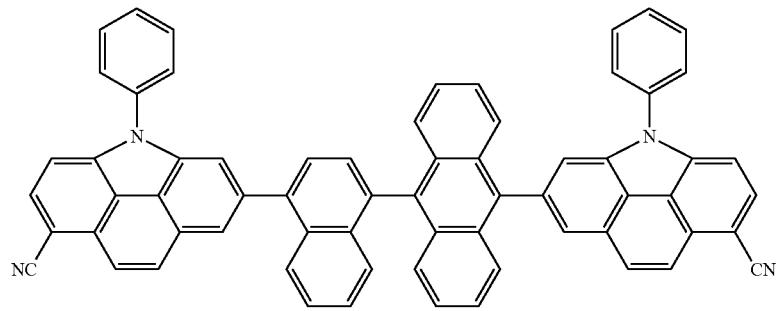
69
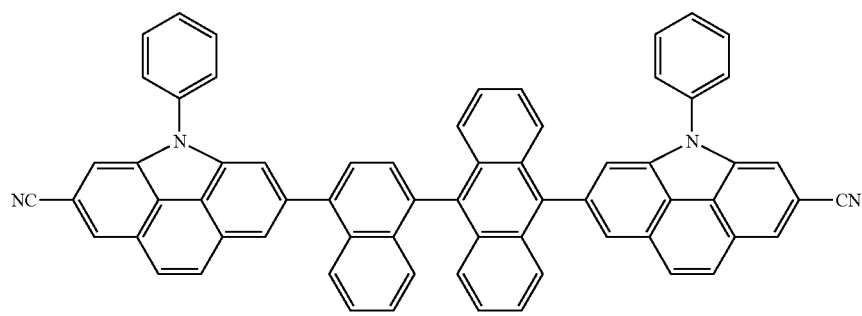
70
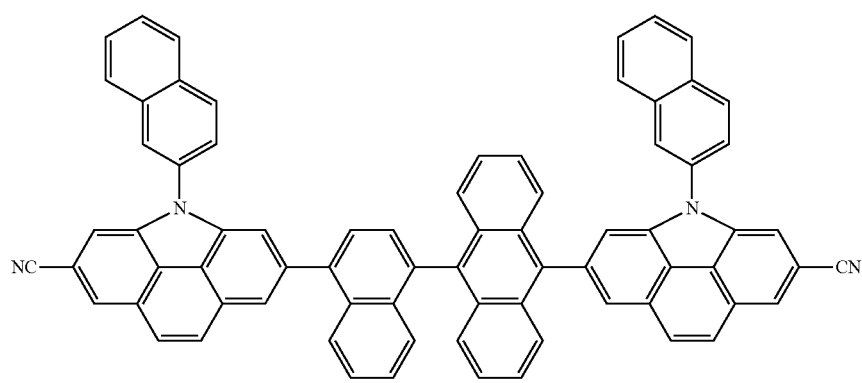
71
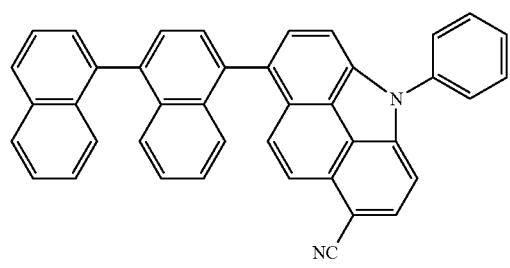
72
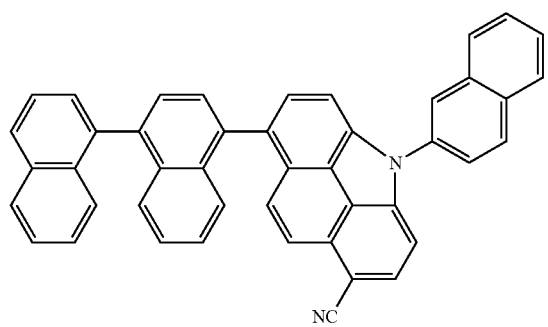

-continued
73
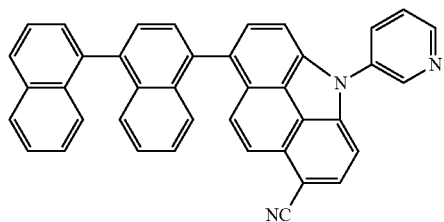
74
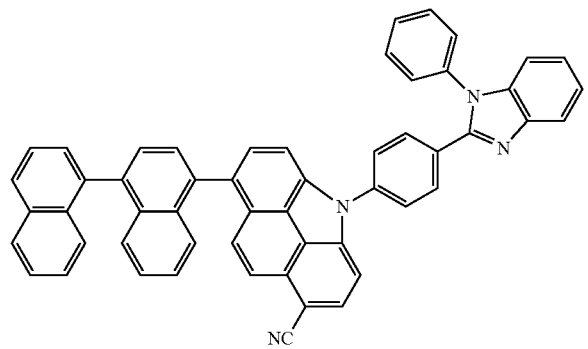
75
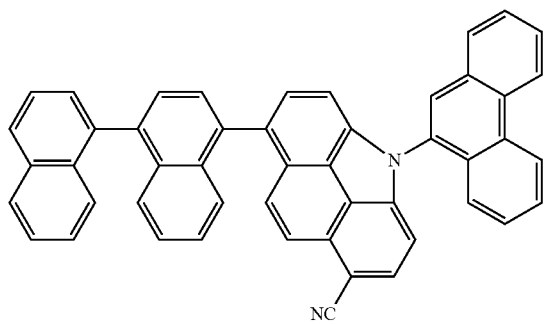
76
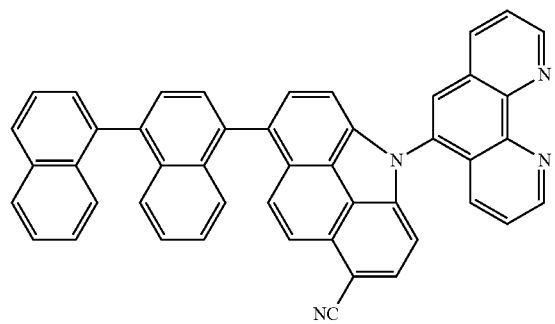
77
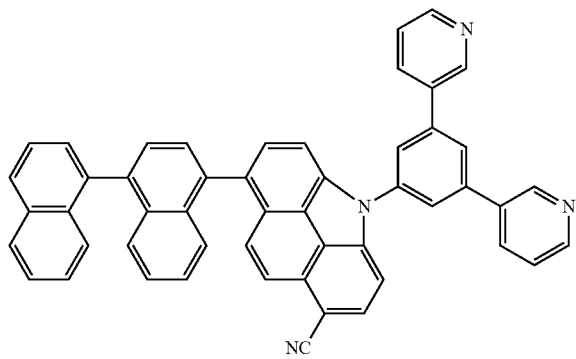
78
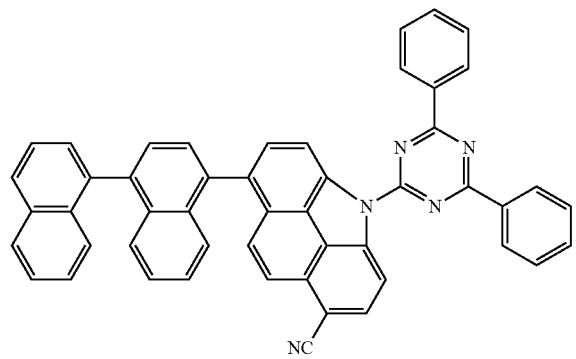
79
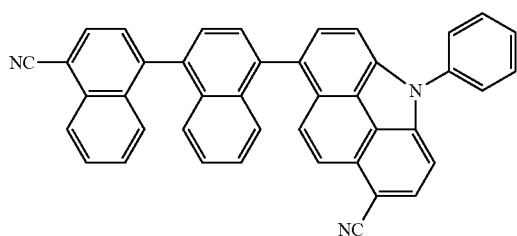
80
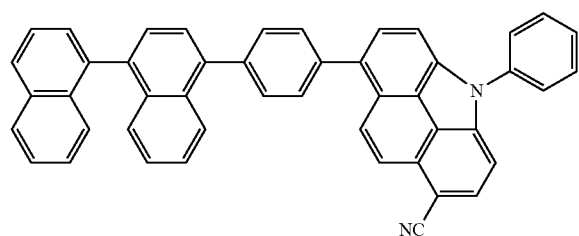
81
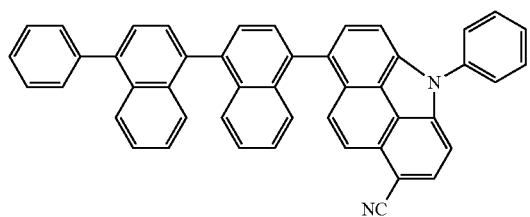
82
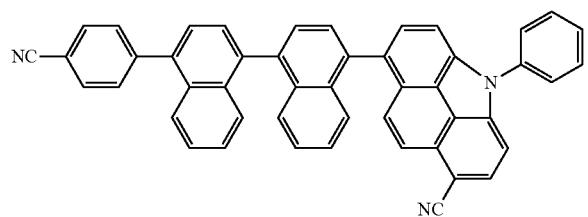

-continued
83
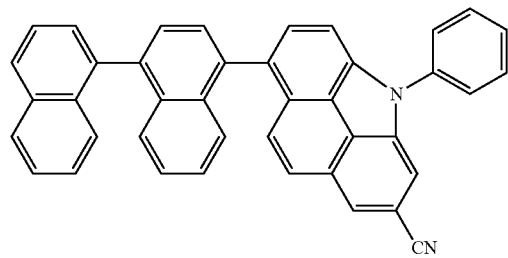
84
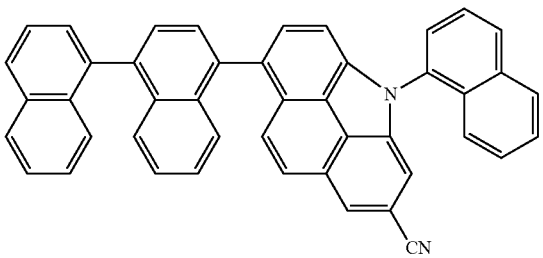
85
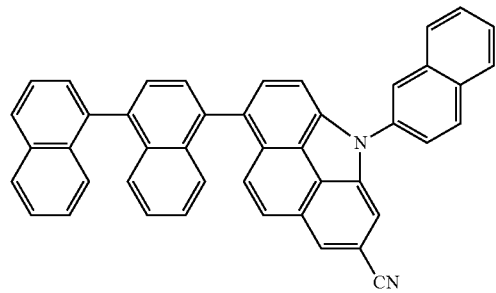
86
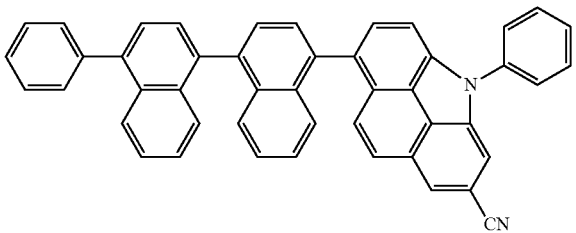
87
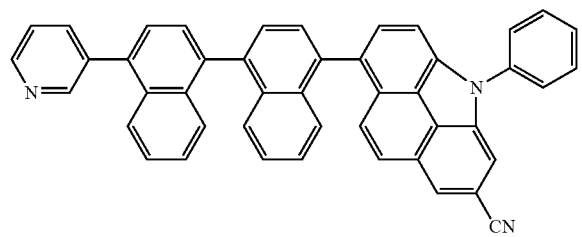
88
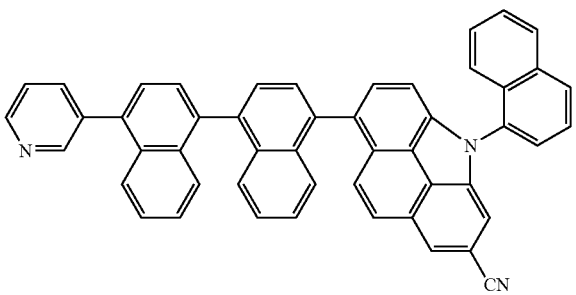
89
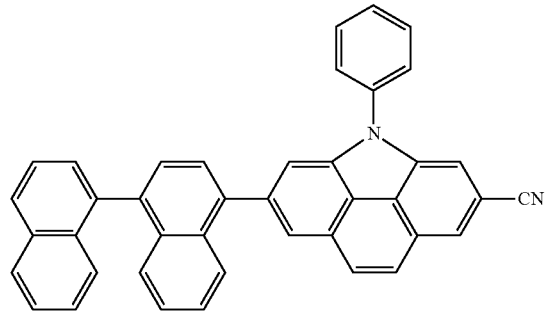
90
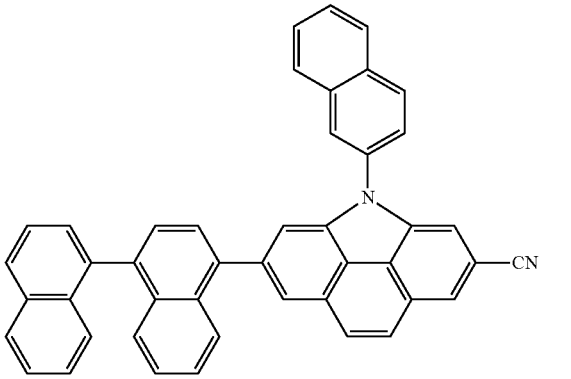
91
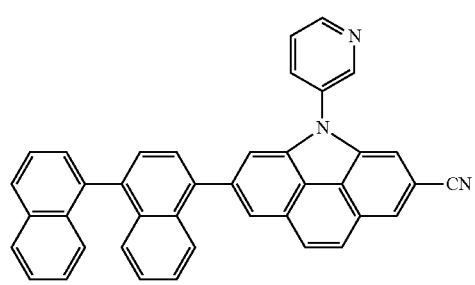
92
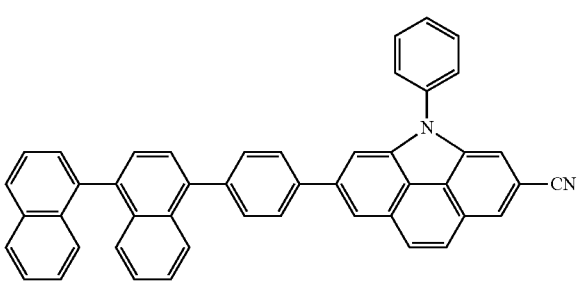

-continued

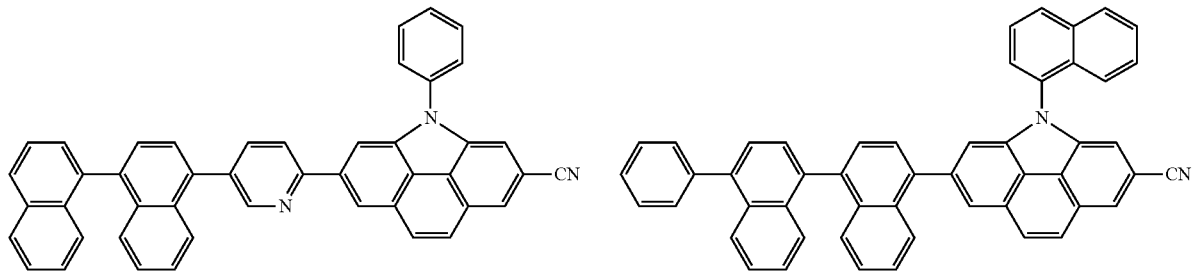

93

94

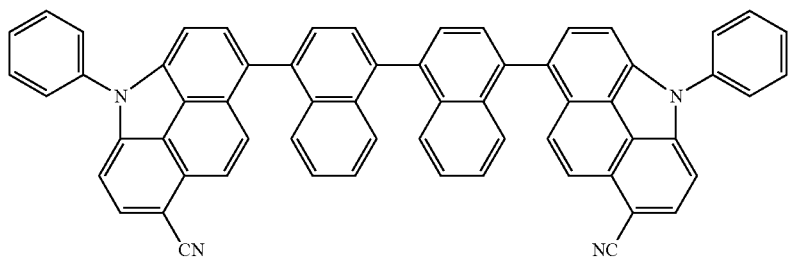

95

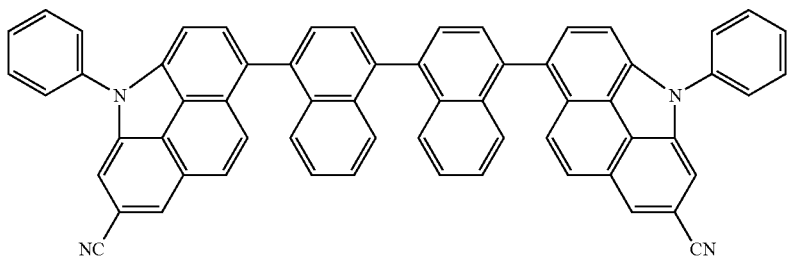

96

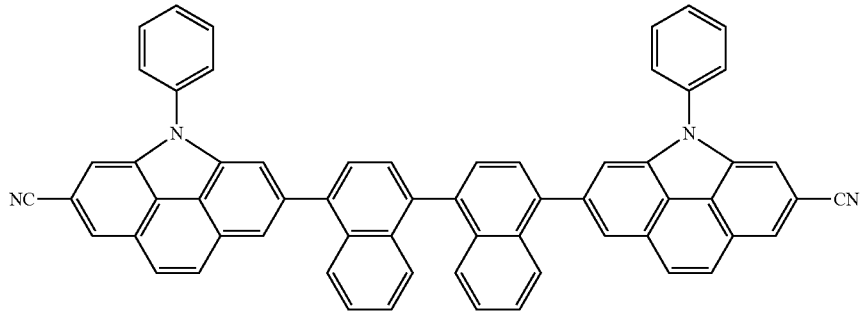

97

10. An organic light-emitting device comprising:
a first electrode;
a second electrode; and
an organic layer between the first electrode and the second electrode,
wherein the organic layer comprises the compound of claim 1.

11. The organic light-emitting device of claim 10, wherein the organic layer is an electron transport layer or an electron injection layer.

12. The organic light-emitting device of claim 10, wherein the organic layer comprises an emission layer, and at least one selected from an electron injection layer, an electron transport layer, a functional layer having both electron injecting and electron transporting capabilities, a hole injection layer, a hole transport layer, and a functional layer having both hole injecting and hole transporting capabilities, wherein the emission layer comprises an anthracene-based compound, an arylamine-based compound, or a styryl-based compound.

13. The organic light-emitting device of claim 10, wherein the organic layer comprises an emission layer comprising a red emission layer, a green emission layer, a blue emission layer or a white emission layer; and at least one selected from an electron injection layer, an electron transport layer, a functional layer having both electron injecting and electron transporting capabilities, a hole injection layer, a hole transport layer, and a functional layer having both hole injecting and hole transporting capabilities,
wherein the red emission layer, the green emission layer, the blue emission layer, or the white emission layer of the emission layer comprises a phosphorescent compound.

14. The organic light-emitting device of claim 13, wherein the organic layer comprises the hole injection layer, the hole transport layer, or the functional layer having both hole injecting and hole transporting capabilities, and the hole injection layer, the hole transport layer, or the functional layer having both hole injecting and hole transporting capabilities comprises a charge-generating material.

15. The organic light-emitting device of claim 14, wherein the charge-generating material is a p-dopant.

16. The organic light-emitting device of claim 15, wherein the p-dopant is a quinone derivative, a metal oxide, or a cyano group-containing compound.

17. The organic light-emitting device of claim 10, wherein the organic layer comprises an electron transport layer comprising the compound and a metal complex.

18. The organic light-emitting device of claim 17, wherein the metal complex is a Li complex.

19. The organic light-emitting device of claim 10, wherein the organic layer is formed by utilizing the compound by a wet process.

20. A flat panel display apparatus comprising:
a thin-film transistor comprising a source electrode and a drain electrode;
the organic light-emitting device of claim 10, wherein the first electrode of the organic light-emitting device is electrically connected to the source electrode or the drain electrode of the thin-film transistor.

* * * * *